United States Patent [19]

Ashton et al.

[11] Patent Number: 5,336,778
[45] Date of Patent: Aug. 9, 1994

[54] SUBSTITUTED TRIAZOLES AS ANGIOTENSIN II ANTAGONISTS

[75] Inventors: Wallace T. Ashton, Clark; Christine L. Cantone, Hazlet; Linda L. Chang, Wayne; Malcolm Maccoss, Freehold; Prasun K. Chakravarty, Edison; William J. Greenlee, Teaneck; Arthur A. Patchett; Thomas F. Walsh, both of Westfield, all of N.J.

[73] Assignee: Merck & Co., Inc., Rahway, N.J.

[21] Appl. No.: 902,353

[22] Filed: Jun. 22, 1992

Related U.S. Application Data

[60] Division of Ser. No. 503,352, Apr. 2, 1990, abandoned, which is a continuation-in-part of Ser. No. 382,138, Jul. 19, 1989, abandoned.

[51] Int. Cl.$^5$ .................. A61K 31/41; A61K 31/505; C07D 257/00; C07D 249/00
[52] U.S. Cl. ..................... 548/250; 544/337; 548/112; 548/251; 548/262.2; 548/262.8; 548/263.2; 548/264.2; 548/264.4
[58] Field of Search ............. 548/112, 251, 263.6, 548/263.8, 264.2, 264.4, 262.2, 262.8, 263.2; 544/331; 514/275, 383, 384, 275.38

[56] References Cited

U.S. PATENT DOCUMENTS

| | | | |
|---|---|---|---|
| 4,207,324 | 6/1980 | Matsumura et al. | 514/397 |
| 4,340,598 | 7/1982 | Furukawa et al. | 424/273 |
| 4,576,958 | 3/1986 | Wexler | 514/400 |
| 4,582,847 | 4/1986 | Furukawa et al. | 514/400 |
| 5,015,651 | 5/1991 | Carini et al. | 514/381 |
| 5,093,346 | 3/1992 | Carini et al. | 548/262.2 |
| 5,098,920 | 3/1992 | Reitz | 548/262.2 |
| 5,140,036 | 8/1992 | Reitz | 548/262.2 |
| 5,187,179 | 2/1993 | Ashton | 548/262.2 |
| 5,217,985 | 6/1993 | Reitz et al. | 548/262.2 |

FOREIGN PATENT DOCUMENTS

| | | |
|---|---|---|
| 028034 | 5/1981 | European Pat. Off. . |
| 253310 | 1/1988 | European Pat. Off. . |
| 323737 | 7/1989 | European Pat. Off. . |
| 343841 | 7/1989 | European Pat. Off. . |

OTHER PUBLICATIONS

Berger, Medicinal Chemistry, 2nd Edition, 1960 pp. 566, 568, 580, 600 and 601.

*Primary Examiner*—Cecilia Tsang
*Attorney, Agent, or Firm*—Robert J. North; Melvin Winokur

[57] ABSTRACT

Novel substituted triazoles of the formula (I), which are useful as angiotensin II antagonists, are disclosed.

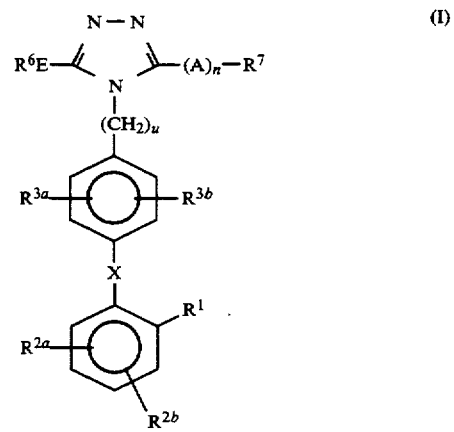

6 Claims, No Drawings

SUBSTITUTED TRIAZOLES AS ANGIOTENSIN II ANTAGONISTS

INTRODUCTION OF THE INVENTION

This is a division of application Ser. No. 07/503,352, filed Apr. 2, 1990, now abandoned which is a continuation-in-part of copending application Ser. No. 382,138 filed Jul. 19, 1989 now abandoned.

This invention relates to novel substituted triazole compounds which are useful as angiotensin II antagonists in the treatment of elevated blood pressure and congestlye heart failure. Thus, the substituted triazole compounds of the invention are useful as antihypertensives.

BACKGROUND OF THE INVENTION

Renin-angiotensin system (RAS) plays a central role in the regulation of normal blood pressure and seems to be critically involved in hypertension development and maintenance as well congestive heart failure. Angiotensin II (A II) an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is by angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp, Hypertens. A*4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847 and 4,880,804; in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1-7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]pyridine-6-carboxylic acid and analogs thereof as antihypertensive agents, specifically $Ca^{2+}$ channel blockers.

DETAILED DESCRIPTION OF THE INVENTION

This invention relates to novel substituted triazole compounds and derivatives thereof which are useful as angiotensin II antagonists and as antihypertensives, in the treatment of congestive heart failure and in the treatment of elevated intraocular pressure. The compounds of this invention have the general formula (I):

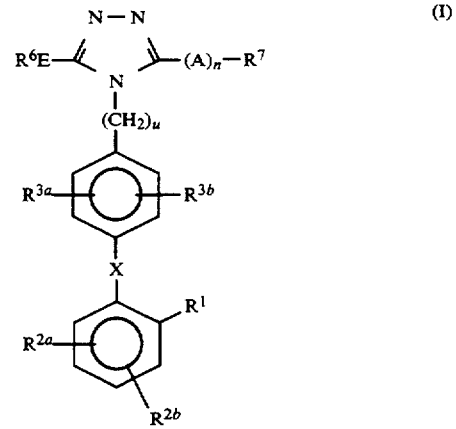

wherein:
$R^1$ is
(a) $-CO_2R^4$,
(b) $-SO_3R^5$,
(c) $-NHSO_2CF_3$,
(d) $-PO(OR^5)_2$,
(e) $-SO_2-NH-R^9$,
(f) $-SO_2NH$-heteroaryl as defined below,
(g) $-CH_2 SO_2NH$-heteroaryl as defined below,
(h) $-SO_2NH-CO-R^{23}$,
(i) $-CH_2SO_2NH-CO-R^{23}$,
(j) $-CONH-SO_2R^{23}$,
(k) $-CH_2CONH-SO_2R^{23}$,
(l) $-NHSO_2NHCO-R^{23}$,
(m) $-NHCONHSO_2R^{23}$,
(n) $-CONHOR^5$,

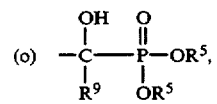

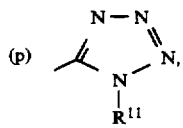

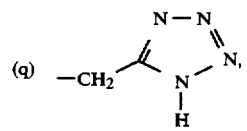

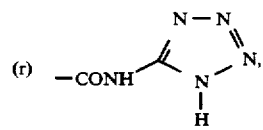

(a) $-CONHNHSO_2CF_3$,

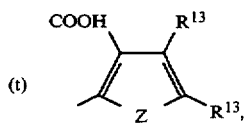

-continued

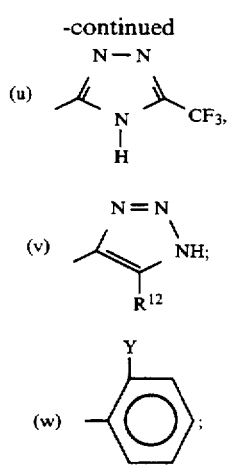

wherein: heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, —$C_1$-$C_4$-alkyl, —$C_1$-$C_4$-alkoxy, —$CF_3$, halo (Cl, Br, F, I), —$NO_2$, —$CO_2H$, —$CO_2$—$C_1$-$C_4$-alkyl, —$NH_2$, —NH($C_1$-$C_4$-alkyl) and —N($C_1$-$C_4$-alkyl)$_2$;

Y is
(1) —$CO_2R^4$,
(2) —$SO_3R^5$,
(3) —$NHSO_2CF_3$,
(4) —$PO(OR^5)_2$,
(5) —$SO_2$1'NH—$R^9$, or
(6) 1H-tetrazol-5-yl:

$R^{2a}$ and $R^{2b}$ are each independently:
(a) hydrogen,
(b) halogen (Cl, Br, I, F),
(c) —$NO_2$,
(d) $NH_2$,
(e) $C_1$-$C_4$-alkylamino,
(f) —$SO_2NHR^9$,
(g) $CF_3$,
(h) $C_1$-$C_4$-alkyl,
(i) $C_1$-$C_4$-alkoxy; or
(j) $R^{2a}$ and $R^{2b}$ on adjacent carbons are bonded together to form a phenyl ring;

$R^{3a}$ is
(a) H,
(b) halo (Cl, Br, I, F),
(c) $C_1$-$C_6$-alkyl,
(d) $C_1$-$C_6$-alkoxy,
(e) $C_1$-$C_6$-alkoxy-$C_1$-$C_4$-alkyl;

$R^{3b}$ is
(a) H,
(b) halo (Cl, Br, I, F),
(c) $NO_2$,
(d) $C_1$-$C_6$-alkyl,
(e) $C_1$-$C_5$-alkylcarbonyloxy,
(f) $C_3$-$C_6$-cycloalkyl,
(g) $C_1$-$C_6$-alkoxy,
(h) —$NHSO_2R^4$,
(i) hydroxy-$C_1$-$C_4$-alkyl,
(j) aryl-$C_1$-$C_4$-alkyl,
(k) $C_1$-$C_4$-alkylthio,
(l) $C_1$-$C_4$-alkylsulfinyl,
(m) $C_1$-$C_4$-alkylsulfonyl,
(n) $NH_2$,
(o) $C_1$-$C_4$-alkylamino,
(p) $C_1$-$C_4$-dialkylamino
(q) $CF_3$
(r) —$SO_2$—$NHR^9$,
(s) aryl;
(t) furyl; or
(u) $R^{3a}$ and $R^{3b}$ on adjacent carbons are bonded together to form a phenyl ring;

wherein aryl is phenyl or naphthyl optionally substituted with one or two substituents selected from the group consisting of halo (Cl, Br, I, F), $C_1$-$C_4$-alkyl, $C_1$-$C_4$-alkoxy, $NO_2$, $CF_3$, $C_1$-$C_4$-alkylthio, OH or $NH_2$;

$R^4$ is H, straight chain or branched $C_1$-$C_6$-alkyl, benzyl or phenyl;

$R^5$ is H,

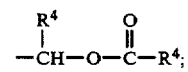

E is a single bond, —$NR^{13}(CH_2)_s$—, —$S(O)_x(CH_2)_s$— where x is 0 to 2 and s is 0 to 5, —CH(OH)—, —$O(CH_2)_s$—, —CO—;

$R^6$ is
(a) aryl as defined above optionally substituted with 1 or 2 substituents selected from the group consisting of halo (Cl, Br, I, F), —O—$C_1$-$C_4$-alkyl, $C_1$-$C_4$-alkyl, —$NO_2$, —$CF_3$, —$SO_2NR^9R^{10}$, —S—$C_1$-$C_4$-alkyl, —OH, —$NH_2$, $C_3$-$C_7$-cycloalkyl, $C_2$-$C_{10}$-alkenyl;
(b) straight chain or branched $C_1$-$C_6$-alkyl, $C_2$-$C_6$-alkenyl or $C_2$-$C_6$-alkynyl each of which can be optionally substituted with a substituent selected from the group consisting of aryl as defined above, $C_3$-$C_7$-cycloalkyl, halo (Cl, Br, I, F), —OH, —O—$C_1$-$C_4$-alkyl, —$NH_2$, —NH($C_1$-$C_4$-alkyl), —N($C_1$-$C_4$-alkyl)$_2$, —NH—$SO_2R^4$, —$COOR^4$, —$SO_2NHR^9$, —S—$C_1$-$C_4$-alkyl; or
(c) an unsubstituted, monosubstituted or disubstituted aromatic 5 or 6 membered ring which can contain one or two members selected from the group consisting of N, O, S, and wherein the substituents are members selected from the group consisting of —OH, —SH, $C_1$-$C_4$-alkyl, $C_1$-$C_4$-alkyloxy, —$CF_3$, halo (Cl, Br, I, F), or $NO_2$;
(d) mono-, di-, tri- or polyfluoro-$C_1$-$C_5$-alkyl;
(e) $C_3$-$C_7$-cycloalkyl optionally substituted with one or more substituents selected from the group consisting of $C_1$-$C_4$-alkyl, —O—$C_1$-$C_4$-alkyl, —S—$C_1$-$C_4$-alkyl, —OH, perfluoro-$C_1$-$C_4$-alkyl, or halo (Cl, Br, F, I);
(f) $C_3$-$C_7$-cycloalkyl-$C_1$-$C_3$-alkyl wherein the cycloalkyl is substituted as in (e) above, A is $S(O)_p$, —O— or NH wherein p is 0 to 2;

$R^7$ is
(a) $C_1$-$C_{10}$-alkyl;
(b) substituted $C_1$-$C_{10}$ alkyl in which one or more substituent(s) is selected from
(1) halogen,
(2) hydroxy,
(3) $C_1$-$C_{10}$-alkoxy,
(4) $C_1$-$C_5$-alkoxycarbonyl,
(5) $C_1$-$C_4$-alkylcarbonyloxy,
(6) $C_3$-$C_8$-cycloalkyl, (7) aryl,
(8) substituted aryl in which the substituents are V and W,
(9) $C_1$-$C_{10}$-alkyl-S(O)$_p$,
(10) $C_3$-$C_8$-cycloalkyl-S(O)$_p$,
(11) phenyl-S(O)$_p$,
(12) substituted phenyl-S(O)$_p$ in which the substituents are V and W,
(13) oxo,
(14) carboxy,
(15) NR$^9$R$^{10}$,
(16) $C_1$-$C_8$-alkylaminocarbonyl;
(17) di($C_1$-$C_5$-alkyl)aminocarbonyl;
(18) cyano;
(c) perfluoro-$C_1$-$C_4$-alkyl,
(d) $C_2$-$C_{10}$-alkenyl,
(e) $C_2$-$C_{10}$-alkynyl,
(f) $C_3$-$C_8$-cycloalkyl,
(g) substituted $C_3$-$C_8$-cycloalkyl in which one or more substituent(s) is selected from the group:
(1) halogen (I, Br, Cl, F),
(2) hydroxy,
(3) $C_1$-$C_{10}$-alkoxy,
(4) $C_1$-$C_5$-alkoxycarbonyl,
(5) $C_1$-$C_4$-alkylcarbonyloxy,
(6) $C_3$-$C_8$-cycloalkyl,
(7) aryl,
(8) substituted aryl in which the substituents are V and W,
(9) $C_1$-$C_{10}$-alkyl-S(O)$_p$ in which p is 0 to 2,
(10) $C_3$-$C_8$-Cycloalkyl-S(O)$_p$,
(11) phenyl-S(O)$_p$,
(12) substituted phenyl-S(O)$_p$ in which the substituents are V and W,
(13) oxo,
(14) carboxy,
(15) NR$^9$R$^{10}$,
(16) $C_1$-$C_5$-alkylaminocarbonyl;
(17) di($C_1$-$C_5$-alkyl)aminocarbonyl;
(18) cyano,
(19) $C_1$-$C_4$-alkylcarbonyl,
(h) aryl,
(i) substituted aryl in which the substituents are V and W,
(j) aryl-(CH$_2$)$_r$—(B)$_b$-(CH$_2$)$_t$—
(k) substituted aryl-(CH$_2$)$_r$—(B)$_b$—(CH$_2$)$_t$— in which the aryl group is substituted with V and W;
(l) a heterocyclic ring of 5 to 6 atoms containing one or two heteroatoms selected from:

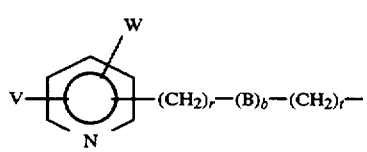

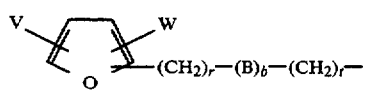

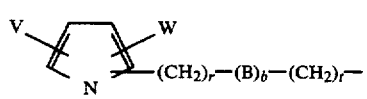

with the proviso that when E is a single bond and n is O, then R$^7$ is:
(a) substituted $C_1$-$C_{10}$-alkyl in which one or more substituent(s) is selected from:
(1) $C_3$-$C_8$-cycloalkyl,
(2) aryl as defined above,
(3) substituted aryl as defined above in which the substituents are V and W,
(4) $C_3$-$C_8$-cycloalkyl-S(O)$_p$ where p is 0 to 2,
(5) phenyl-S(O)$_p$ where p is 0 to 2,
(6) substituted phenyl-S(O)$_p$ where p is 0 to 2 and the substituents are V and W;
(b) CF$_3$;
(c) $C_3$-$C_8$-cycloalkyl;
(d) substituted $C_3$-$C_8$-cycloalkyl in which the substituent is selected from;
(1) $C_1$-$C_5$-alkyl,
(2) $C_1$-$C_5$-alkoxy;
(e) aryl as defined above;
(f) substituted aryl as defined above in which the substituents are V and W;
(g) aryl-(CH$_2$)$_r$—(B)$_b$—(CH$_2$)$_t$— in which b is 0 when B is —C(O)—;
(h) substituted aryl-(CH$_2$)$_r$—(B)$_b$—(CH$_2$)$_t$— in which b is 0 when B is —C(O)— and the aryl group is substituted with V and W;
(i) a heterocyclic ring of 5 to 6 atoms containing one or two heteroatoms, said heterocyclic ring being selected from:

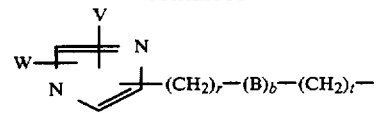

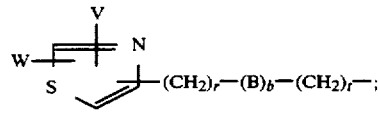

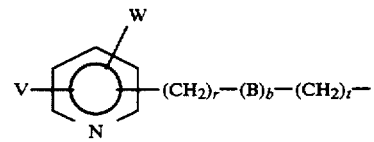

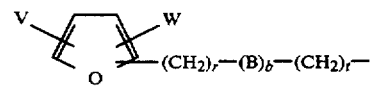

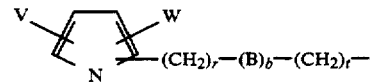

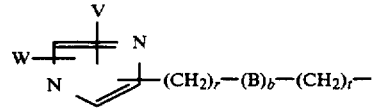

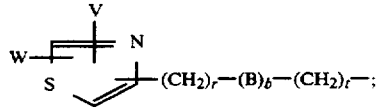

n is 0 or 1;

B is —C(O)—, —S—, —O—, —NR⁴, —NR⁴C(O)—, or —C(O)NR⁴;
b is 0 or 1;
r and t are 0 to 2;
u is 1 or 2;
p is 0 to 2;
V and W are each independently selected from:
(a) H,
(b) $C_1$-$C_5$-alkoxy,
(c) $C_1$-$C_5$-alkyl,
(d) hydroxy,
(e) $C_1$-$C_5$-alkyl-S(O)$_p$,
(f) —CN,
(g) —NO₂,
(h) —NR⁹R¹⁰,
(i) $C_1$-$C_4$-alkyl-CONR⁹R¹⁰,
(j) —CO₂R⁹,
(k) $C_1$-$C_5$-alkyl-carbonyl,
(l) trifluoromethyl,
(m) halogen,
(n) hydroxy-$C_1$-$C_4$-alkyl—,
(o) $C_1$-$C_4$-alkyl-CO₂R⁹,
(p) —1H-tetrazol-5-yl,
(q) —NH-SO₂CF₃;
(r) aryl as defined above,
(s) —OCONR⁹R¹⁰,
(t) —NR⁴CO₂$R^9$,
(u) —NR⁴CONR⁹R¹⁰,
(v) —NR⁴CON(CH₂CH₂)₂Q where Q is O,S-(O)$_p$ or NR⁹,
(w) —OCON(CH₂CH₂)₂Q where Q is as defined above,
(x) —CONR⁹R¹⁰;
R⁹ H, $C_1$-$C_5$-alkyl, phenyl or benzyl;
R¹⁰ H, $C_1$-$C_4$-alkyl;
or R⁹ and R¹⁰ together may be —(CH₂)$_m$— where m is 3-6;
R¹¹ is H, $C_1$-$C_6$-alkyl, $C_2$-$C_4$-alkenyl, $C_1$-$C_4$-alkoxy-$C_1$-$C_4$-alkyl, or —CH₂-$C_6$H₄R²⁰;
R¹² is —CN, —NO₂ or —CO₂R⁴;
R¹³ is H, $C_1$-$C_4$-acyl, $C_1$-$C_6$-alkyl, allyl, $C_3$-$C_6$-cycloalkyl, phenyl or benzyl;
R¹⁴ is H, $C_1$-$C_8$-alkyl, $C_1$-$C_8$-perfluoroalkyl, $C_3$-$C_6$-cycloalkyl, phenyl or benzyl;
R¹⁵ is H, $C_1$-$C_6$-alkyl, hydroxy;
R¹⁶ is H, $C_1$-$C_6$-alkyl, $C_3$-$C_6$-cycloalkyl, phenyl or benzyl;
R¹⁷ is —NR⁹R¹⁰, —OR¹⁰, —NHCONH₂, —NHCSNH₂,

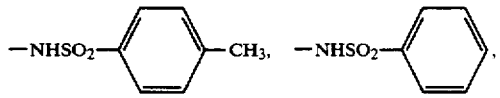

—NHSO₂CF₃;
R¹⁸ and R¹⁹ are independently $C_1$-$C_4$-alkyl or taken together are —(CH₂)$_q$— where q is 2 or 3;
R²⁰ is H, —NO₂, —NH₂, —OH or —OCH₃;
R²¹ is $C_1$-$C_5$-alkyl or CF₃;
R²³ is
(a) aryl as defined above,
(b) heteroaryl as defined above,
(c) $C_3$-$C_7$-cycloalkyl,
(d) $C_1$-$C_4$-alkyl optionally substituted with a substituent selected from the group consisting of aryl as defined above, heteroaryl as defined above, —OH, —SH, $C_1$-$C_4$-alkyl, —O($C_1$-$C_4$-alkyl), —S($C_1$-$C_4$-alkyl), —CF₃, halo ($C_1$, I), —NO₂, —CO₂H, —CO₂-$C_1$-$C_4$-alkyl, —NH₂, —NH($C_1$-$C_4$-alkyl), —N($C_1$-$C_4$-alkyl)2, —N(CH₂CH₂)₂L where L is a single bond, CH₂, O, S(O)p or NR⁹, —PO₃H, —PO(OH)(O—$C_1$-$C_4$-alkyl);

X is
(a) a carbon-carbon single bond,
(b) —CO—,
(c) —O—,
(d) —S—,

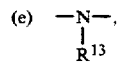

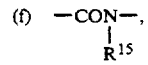

(h) —OCH₂—,
(i) —CH₂O—
—SCH₂—,
—CH₂S—,
(l) —NHC(R⁹)(R¹⁰)—,
(m) —NR⁹SO₂—,
(n) —SO₂NR⁹—,
(o) —C(R⁹)>(R¹⁰)NH—,
(p) —CH=CH—,
(q) —CF=CF—,
(r) —CH=CF—,
(s) —CF=CH—,
(t) —CH₂CH₂—,
(u) —CF₂CF₂—,
(v) 1,1 and 1,2-disubstituted cyclopropyl,

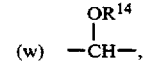

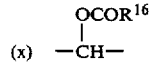

or

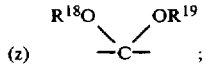

Z is O, NR¹³ or S; and,
the pharmaceutically acceptable salts thereof.
One embodiment of the compounds of Formula (I) are those compounds wherein:
R¹ is
(a) —COOH,

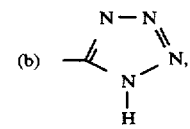

(c) —NH—SO$_2$CF$_3$,
(d) —CONHSO$_2$R$^{23}$,
(e) —SO$_2$NHCOR$^{23}$,
(f) SO$_2$NH-heteroaryl;

R$^{2a}$ is H;
R$^{2b}$ is H, F, Cl, CF$_3$ or C$_1$-C$_4$-alkyl;
R$^{3a}$ is H;
R$^{3b}$ is H, F, Cl, CF$_3$, C$_1$-C$_4$-alkyl, C$_5$-C$_6$-cycloalkyl, —COOCH$_3$, —COOC$_2$H$_5$, —SO$_2$—CH$_3$, NH$_2$, —N(C$_1$-C$_4$-alkyl)2 or —NH—SO$_2$CH$_3$;
E is a single bond, —O— or —S—;
R$^6$ is
 (a) C$_1$-C$_6$-alkyl optionally substituted with a substituent selected from the group consisting of C$_1$, CF$_3$, OH, —O—CH$_3$, —OC$_2$H$_5$, —S—CH$_3$, —S—C$_2$H$_5$ or phenyl;
 (b) C$_2$-C$_6$-alkenyl or C$_2$-C$_6$-alkynyl;
 (c) aryl as defined above optionally substituted with a substituent selected from the group consisting of halo (Cl, F, Br, I), —CF$_3$, —NO$_2$, —OH, —NH$_2$, —S—CH$_3$, —S—C$_2$H$_5$, —SO$_2$NH$_2$ —O—CH$_3$; or,
 (d) a heteroaryl which is a member selected from the group consisting of 2-pyridyl, 4-pyridyl, 2-pyrimidyl, 4-pyrimidyl, imidazoyl, thiazolyl, thienyl, or furyl;
 (e) perfluoro-C$_1$-C$_4$-alkyl selected from CF$_3$, CF$_3$CF$_2$, CF$_3$CF$_2$CF$_2$, CF$_3$CF$_2$CF$_2$CF$_2$;
 (f) C$_3$-C$_7$-cycloalkyl optionally substituted with a substituent selected from the group consisting of C$_1$, CF$_3$, OH, —O—H$_3$, —O—C$_2$H$_5$, —S—CH$_3$, —S—C$_2$H$_5$, CH$_3$, CH$_2$CH$_3$, CF$_2$CF$_3$, (CF$_2$)2CF$_3$ or phenyl;

R$^7$ is
 (a) C$_1$-C$_{10}$-alkyl,
 (b) substituted C$_1$-C$_{10}$-alkyl in which one or two substituents are selected from:
  (1) hydroxy,
  (2) C$_1$-C$_5$-alkoxy,
  (3) C$_1$-C$_5$-alkoxycarbonyl,
  C$_1$-C$_4$-alkylcarbonyloxy,
  (5) C$_3$-C$_8$-cycloalkyl,
  (6) phenyl,
  (7) substituted phenyl in which the substituents are V and W,
  (8) C$_1$-C$_5$-alkyl-S(O)$_p$,
  (9) phenyl-S(O)$_p$,
  (10) substituted phenyl-S(O)$_p$ in which the substituents are V and W,
  (11) oxo,
  (12) carboxy,
   (13) C$_1$-C$_5$-alkylaminocarbonyl,
   (14) di(C$_1$-C$_5$-alkyl)aminocarbonyl;
 (c) CF$_3$,
 (d) aryl,
 (e) substituted aryl in which the substituents are V and W,
 (f) aryl—(CH$_2$)$_r$—(B)$_b$—(CH$_2$)$_r$—,
 (g) substituted aryl-(CH$_2$)$_r$—(B)$_b$—(CH$_2$)$_r$—,
 (h) a heterocyclic ring of 5 to 6 atoms containing one or two heteroatoms selected from:

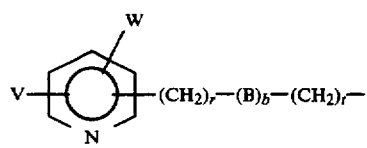

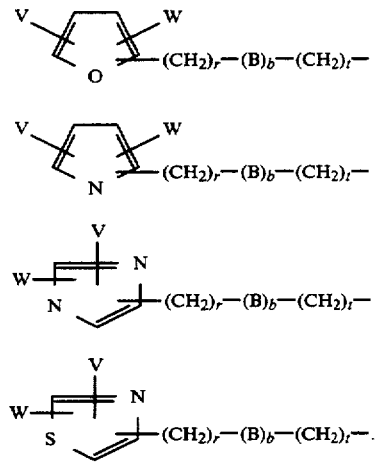

A is —S—, —S(O)— or —O—;
V and W are independently selected from:
 (a) hydrogen,
 (b) C$_1$-C$_5$-alkoxy,
 (c) C$_1$-C$_5$-alkyl,
 (d) hydroxy,
 (e) NR$^9$R$^{10}$,
 (f) CO$_2$R$^9$
 (g) trifluoromethyl,
 (h) halogen,
 (i) hydroxy-C$_1$-C$_4$-alkyl,
 (j) -1H-tetrazol-5-yl,
 (k) —NH—SO$_2$CF$_3$,
 (l) —CN,
 (m) —NO$_2$,
 (n) C$_1$-C$_5$-alkyl—S(O)$_p$,
 (o) C$_1$-C$_4$-alkyl—CONR$^9$R$^{10}$,
 (p) C$_1$-C$_5$-alkylcarbonyl,
 (q) —CONR$^9$R$^{10}$,
u is 1;
X is:
 (a) carbon-carbon single bond,
 (b) —C(O)—,
 (c) —NR$^{15}$C(O)—.

In one class of this embodiment are those compounds of formula (I) wherein:
E is a single bond or —S—;
R$^{2a}$, R$^{2b}$ R$^{3a}$ and R$^{3b}$ are each H;
R$^6$ is C$_1$-C$_6$-alkyl.

Illustrating this class are those compounds of formula (I) wherein:
R$^7$ is:
 (a) C$_1$-C$_{10}$-alkyl,
 (b) substituted C$_1$-C$_{10}$-alkyl in which one or two substituents are selected from:
  (1) hydroxy,
  (2) C$_1$C$_5$-alkoxy,
  (3) C$_1$-C$_5$-alkoxycarbonyl,
  (4) phenyl,
  (5) carboxy,
  (6) C$_1$-C$_5$-alkylaminocarbonyl;
 (c) CF$_3$;
 (d) phenyl;
 (e) phenyl substituted with V and W;
 (f) phenyl-(CH$_2$)$_r$-(B)$_b$-(CH$_2$)$_r$—;
 (g) phenyl-(CH$_2$)$_r$-(B)$_b$-(CH$_2$)$_r$— in which the phenyl is substituted with V and W;

(h) a heterocyclic moiety selected from:

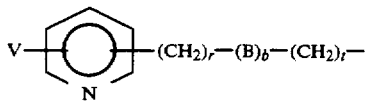

or

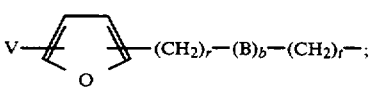

V and W are selected from:
(a) hydrogen,
(b) $C_1$–$C_5$-alkyl,
(c) $C_1$–$C_5$-alkoxy,
(d) $CO_2R^9$,
(e) halogen,
(f) hydroxy-$C_1$–$C_4$-alkyl,
(g) —1H-tetrazol-5-yl,
(h) —NH—$SO_2CF_3$;
(i) —CN,
(j) —$NO_2$;

X is —$NR^{15}C(O)$— or a carbon-carbon single bond.
Exemplifying this class are the following compounds:
(1) 3-n-Butyl-5-(carbomethoxymethylthio)-4-[4-(2-carboxybenzamido)benzyl]-4H-1,2,4-triazole;
(2) 3-n-Butyl-4-[4-(2-carboxybenzamido)benzyl]-5-[(N-methylcarbamoyl)methylthio]-4gH-1,2,4-triazole;
(3) 3-n-Butyl-4-[4-(2-carboxybenzamido)benzyl]-5-(2-hydroxyethylthio)-4H-1,2,4-triazole;
(4) 3-Benzylthio-5-n-butyl-4-[4-(2-carboxybenzamido)-benzyl]-4H-1,2,4-triazole;
(5) 3-n-Butyl-4-[4-(2-carboxybenzamido)benzyl]-5-phenylthio-4H-1,2,4-triazole;
(6) 4-[4-(2-Carboxybenzamido)benzyl]-3-ethylthio-5-trifluoromethyl-4H-1,2,4-triazole;
(7) 4-[4-(2-Carboxybenzamido)benzyl]-3-ethylthio-5-methoxymethyl-4H-1,2,4-triazole;
(8) 4-[4-(2-Carboxybenzamido)benzyl]-3-ethylthio-5-phenyl-4H-1,2,4-triazole;
(9) 3-n-Butyl-4-[4-(2-carboxybenzamido)benzyl]-5-(2-furyl)-4H-1,2,4-triazole;
(10) 3-n-Butyl-4-[4-(2-carboxybenzamido)benzyl]-5-(4-pyridyl)-4H-1,2,4-triazole;
(11) 3-n-Butyl-4-[4-(2-carboxybenzamido)benzyl]-5-(carboxymethylthio)-4H-1,2,4-triazole;
(12) 3-n-Butyl-5-[2-(carbomethoxy)benzylthio]-4-[4-(2-carboxybenzamido)benzyl]-4H-1,2,4-triazole;
(13) 3-n-Butyl-4-[4-(2-carboxybenzamido)benzyl]-5-(2-carboxybenzylthio)-4H-1,2,4-triazole;
(14) 3-n-Butyl-5-(carbomethoxymethylthio)-4-[(2'-carboxybiphenyl-4-yl)methyl]-4H-1,2,4-triazole;
(15) 3-n-Butyl-5-(4-chlorobenzylthio)-4-[(2'-(1H-tetrazol-5-yl)biphenyl-4-yl)methyl]-4H-1,2,4-triazole;
(16) 3-n-Butyl-5-(4-chlorobenzylsulfinyl)-4-[(2'-(1H-tetrazol-5-yl)biphenyl-4-yl)methyl]-4H-1,2,4-triazole;
(17) 3-n-Butyl-5-(4-chlorobenzylsulfonyl)-4-[(2'-(1H-tetrazol-5-yl)biphenyl-4-yl)methyl]-4H-1,2,4-triazole;
(18) 3-n-Butyl-5-(4-nitrobenzylthio)-4-[(2'-(1H-tetrazol-5-yl)biphenyl-4-yl)methyl]-4H-1,2,4-triazole;
(19) 3-n-Butyl-5-(4-nitrobenzylsulfinyl)-4-[(2'-(1H-tetrazol-5-yl)biphenyl-4-yl)methyl]-4H-1,2,4-triazole;
(20) 3-n-Butyl-5-(cyclohexylmethylthio)-4-[(2'-(1Htetrazol-5-yl)biphenyl-4-yl)methyl]-4H-1,2,4-triazole;
(21) 3-n-Butyl-5-(4-chlorobenzylthio)-4-[4-(2-(1e,uns/H/ -tetrazol-5-yl)benzamido)benzyl]-4H-1,2,4-triazole;
(22) 3-n-Butyl-5-(4-chlorobenzylsulfinyl)-4-[(2-(1H-tetrazol-5-yl)benzamido)benzyl]-4H-1,2,4-triazole;
(23) 3-n-Butyl-5-methylthio-4-[(2'-(1H-tetrazol-5-yl)biphenyl-4-yl)methyl]-4H-1,2,4-triazole;
(24) 3-n-Butyl-5-methylsulfonyl-4-[(2'-(1H-tetrazol-5-yl)biphenyl-4-yl)methyl]-4H-1,2,4-triazole;
(25) 3-Benzyloxy-5-n-butyl-4-[(2'-(1H-tetrazol-5-yl)biphenyl-4-yl)methyl]-4H-1,2,4-triazole;
(26) 3-(N-Benzyl—N-methylcarbamoyl)-5-n-butyl-4-[(2'-(1H-tetrazol-5-yl)biphenyl-4-yl)methyl]-4H-1,2,4-triazole;
(27) 4-[4-(2-Carboxybenzamido)benzyl]-3-(n-propylthio)-5-trifluoromethyl-4H-1,2,4-triazole;
(28) 4-[4-(2-Carboxybenzamido)benzyl]-5-phenyl-3-n-propylthio-4H-1,2,4-triazole;
(29) 3-n-Butyl-4-[4-(2-carboxybenzamido)benzyl]-5-phenyl-4H-1,2,4-triazole;
(30) 3-n-Butyl-4-[4-(2-carboxybenzamido)benzyl]-5-(3-pyridyl)-4H-1,2,4-triazole;
(31) (±)-3-n-Butyl-5-[(1-carbomethoxy-1-propyl)-thio]-4-[4-(2-carboxybenzamido)benzyl]-4H-1,2,4-triazole;
(32) 3-n-Butyl-4-[4-(2-carboxybenzamido)benzyl]-5-(phenacylthio)-4H-1,2,4-triazole;
(33) 3-Benzylthio-4-[4-(2-carboxy-benzamido)benzyl]-5-n-propyl-4H-1,2,4-triazole;
(34) 3-n-Butyl-a-[4-(2-carboxybenzamido)benzyl]-5-(3-methylbenzylthio)-4H-1,2,4-triazole;
(35) 3-n-Butyl-4-[4-(2-carboxybenzamido)benzyl]-5-(2-methylbenzylthio )-4H-1,2,4-triazole;
(36) 3-n-Butyl-4-[4-(2-carboxybenzamido)benzyl]-5-(4-methylbenzylthio)-4H-1,2,4-triazole;
(37) 3-n-Butyl-4-[4-(2-carboxybenzamido)benzyl]-5-(2-chlorobenzylthio)-4H-1,2,4-triazole;
(38) 3-n-Butyl-4-[4-(2-carboxybenzamido)benzyl]-5-(3-chlorobenzylthio )-4H-1,2,4-triazole;
(39) 3-n-Butyl-4-[4-(2-carboxybenzamido)benzyl]-5-(4-chlorobenzylthio)-4H-1,2,4-triazole;
(40) 3-n-Butyl-4-[4-(2-carboxybenzamido)benzyl]-5-(3-methoxybenzylthio)-4H-1,2,4-triazole;
(41) 3-n-Butyl-4-[4-(2-carboxybenzamido)benzyl]-5-(phenethylthio)-4H-1,2,4-triazole;
(42) 3-Benzyl-4-[4-(2-carboxybenzamido)benzyl]-5-ethylthio-4H-1,2,4-triazole;
(43) 3-Benzyl-4-[4-(2-carboxybenzamido)benzyl]-5-(n-propylthio)-4H-1,2,4-triazole;
(44) (±)-3-n-Butyl-5-[α-(carbomethoxy)benzylthio]-4-[4-(2-carboxybenzamido)benzyl]-4H-1,2,4-triazole;
(45) (±)-3-n-Butyl-4-[4-(2-carboxybenzamido)benzyl]-(α-carboxybenzylthio)-4H-1,2,4-triazole;
(46) 3-n-Butyl-4-[4-(2-carboxybenzamido)benzyl]-5-(2-cyanobenzylthio)-4H-1,2,4-triazole;
(47) 3-n-Butyl-4-[4-(2-carboxybenzamido)benzyl]-5-[4-(trifluoromethyl)benzylthio]-4H-1,2,4-triazole;
(48) 4-[4-(2-Carboxybenzamido)benzyl]-3-(2-phenylethyl)-5-n-propylthio-4H-1,2,4-triazole;
(49) 4-[4-(2-Carboxybenzamido)benzyl]-3-(3-phenylpropyl)-5-n-propylthio-4H-1,2,4-triazole;

(50) 4-[4-(2-Carboxybenzamido)benzyl]-3-phenylthiomethyl-5-n-propylthio-4H-1,2,4-triazole;
(51) 3-n-Butyl-4-[4-(2-carboxybenzamido)benzyl]-5-(4-methoxybenzylthio)-4H-1,2,4-triazole;
(52) 3-n-Butyl-4-[4-(2-carboxybenzamido)benzyl]-5-(2-napthylmethylthio)-4H-1,2,4-triazole;
(53) 3-n-Butyl-5-[3-(carbomethoxy)benzylthio]-4-[4-(2-carboxybenzamido)benzyl]-4H-1,2,4-triazole;
(54) 3-n-Butyl-4-[4-(2-carboxybenzamido)benzyl]-5-(3-carboxybenzylthio)-4H-1,2,4-triazole;
(55) 3-Benzylthio-5-n-butyl-4-[(2'-carboxybiphenyl-4-yl)methyl]-4H-1,2,4-triazole;
(56) 3-n-Butyl-4-[(2'-carboxybiphenyl-4-yl)-methyl]-5-(4-nitrobenzylthio)-4H-1,2,4-triazole;
(57) 3-n-Butyl-4-[(2'-carboxybiphenyl-4-yl)-methyl]-5-(4-methoxybenzylthio)-4H-1,2,4-triazole;
(58) 3-n-Butyl-4-[(2'-carboxybiphenyl-4-yl)-methyl]-5-(4-chlorobenzylthio )-4H-1,2,4-triazole;
(59) 3-n-Butyl-4-[(2'-carboxybiphenyl-4-yl)-methyl]-5-(2-methylbenzylthio)-4H-1,2,4-triazole;
(60) 3-n-Butyl-4-[(2'-carboxybiphenyl-4-yl)-methyl]-5-(3-methylbenzylthio)-4H-1,2,4-triazole;
(61) 3-n-Butyl-4-[(2'-carboxybiphenyl-4-yl)-methyl]-5-(4-methylbenzylthio)-4H-1,2,4-triazole;
(62) 3-n-Butyl-5-[2-(carbomethoxy)benzylthio]-4-[(2'-carboxybiphenyl-4-yl)methyl]-4H-1,2,4-triazole;
(63) 3-n-Butyl-5-[3-(carbomethoxy)benzylthio]-4-[(2'-carboxybiphenyl-4-yl)methyl]-4H-1,2,4-triazole;
(64) 3-n-Butyl-5-[4-(carbomethoxy)benzylthio]-4-[(2'-carboxybiphenyl-4-yl)methyl]-4H-1,2,4-triazole;
(65) 3-n-Butyl-5-[α-(carbomethoxy)benzylthio]-4-[(2'-carboxybiphenyl-4-yl)methyl]-4H-1,2,4-triazole;
(66) 3-n-Butyl-5-(2-carboxybenzylthio)-4-[(2'-carboxybiphenyl-4-yl)methyl]-4H-1,2,4-triazole;
(67) 3-n-Butyl-5-(3-carboxybenzylthio)-4-[(2'-carboxybiphenyl-4-yl)methyl]-4H-1,2,4-triazole;
(68) 3-n-Butyl-5-(4-carboxybenzylthio)-4-[(2'-carboxybiphenyl-4-yl)methyl]-4H-1,2,4-triazole;
(69) 3-n-Butyl-5-(α-carboxybenzylthio)-4-[(2'-carboxybiphenyl-4-yl)methyl]-4H-1,2,4-triazole;
(70) 3-n-Butyl-4-[(2'-carboxybiphenyl-4-yl)-methyl]-5-[2-(hydroxymethyl)benzylthio]-4H-1,2,4-triazole;
(71) 3-n-Butyl-4-[(2'-carboxybiphenyl-4-yl)-methyl]-5-[3-(hydroxymethyl)benzylthio]-4H-1,2,4-triazole;
(72) 3-n-Butyl-4-[(2'-carboxybiphenyl-4-yl)methyl]-5-[4-(hydroxymethyl)benzylthio]-4H-1,2,4-triazole;
(73) 3-n-Butyl-4-[(2'-carboxybiphenyl-4-yl)-methyl]-5-[α-(hydroxymethyl)benzylthio]-4H-1,2,4-triazole;
(74) 3-n-Butyl-4-[(2'-carboxybiphenyl-4-yl)methyl]-5-(cyclohexylmethylthio)-4H-1,2,4-triazole;
(75) 3-n-Butyl-4-[(2'-carboxybiphenyl-4-yl)methyl]-5-(4-nitrobenzylsulfinyl)-4H-1,2,4-triazole;
(76) 3-n-Butyl-4-[(2'-carboxybiphenyl-4-yl)methyl]-5-(4-chlorobenzylsulfinyl)-4H-1,2,4-triazole;
(77) 3-Benzylthio-5-n-butyl-4-[[2'-(1H-tetrazol-5-yl)biphenyl-4-yl]methyl]-4H-1,2,4-triazole;
(78) 3-n-Butyl-5-phenylthio-4-[[2'-(1H-tetrazol-5-yl)biphenyl-4-yl]methyl]-4H-1,2,4-triazole;
(79) 3-n-Butyl-5-phenethylthio-4-[[2'-(1H-tetrazol-5-yl)biphenyl-4-yl]methyl]-4H-1,2,4-triazole;
(80) 3-(4-Chlorobenzylthio)-5-n-propyl-4-[[2'-(1H-tetrazol-5-yl)biphenyl-4-yl]methyl]-4H-1,2,4-triazole;
(81) 3-(4-Chlorobenzylthio)-5-n-pentyl-4-[[2'-(1H-tetrazol-5-yl)biphenyl-4-yl]methyl]-4H-1,2,4-triazole;
(82) 3-n-Butyl-5-(2-chlorobenzylthio)-4-[[2'-(1H-tetrazol-5-yl)biphenyl-4-yl]methyl]-4H-1,2,4-triazole;
(83) 3-n-Butyl-5-(2-nitrobenzylthio)-4-[[2'-(1H-tetrazol-5-yl)biphenyl-4-yl]methyl]-4H-1,2,4-triazole;
(84) 3-n-Butyl-5-(3-methoxybenzylthio)-4-[[2'-(1H-tetrazol-5-yl)biphenyl-4-yl]methyl]-4H-1,2,4-triazole;
(85) 3-n-Butyl-5-(4-methoxybenzylthio)-4-[[2'-(1H-tetrazol-5-yl)biphenyl-4-yl]methyl]-4H-1,2,4-triazole;
(86) 3-n-Butyl-5-[2-(carbomethoxy)benzylthio]-4-[[2'-(1H-tetrazol-5-yl)biphenyl-4-yl]methyl]-4H-1,2,4-triazole;
(87) 3-n-Butyl-5-(2-carboxybenzylthio)-4-[[2'-(1H-tetrazol-5-yl)biphenyl-4-yl]methyl]-4H-1,2,4-triazole;
(88) 3-n-Butyl-5-[2-(hydroxymethyl)benzylthio]-4-[[2'-(1H-tetrazol-5-yl)biphenyl-4-yl]methyl]-4H-1,2,4-triazole;
(89) 3-n-Butyl-5-isobutylthio-4-[[2'-(1H-tetrazol-5-yl)biphenyl-4-yl]methyl]-4H-1,2,4-triazole;
(90) 3-n-Butyl- 5-(4-methoxybenzylsulfinyl)-4-[[2'-(1H-tetrazol-5-yl)biphenyl-4-yl]methyl]-4H-1,2,4-triazole;
(91) 3-n-Butyl-5-methylsulfinyl-4-[[2'-(1H-tetrazol-5-yl)biphenyl-4-yl]methyl]-4H-1,2,4-triazole;
(92) 3-n-Butyl-5-(N-methyl-N-phenylcarbamoyl)-4-[[2'-(1H-tetrazol-5-yl)biphenyl-4-yl]methyl]-4H-1,2,4-triazole;
(93) 3-n-Butyl-5-(4-methoxybenzylthio)-4-[4-[2-(1H-tetrazol-5-yl)benzamido]benzyl]-4H-1,2,4-triazole;
(94) 3-n-Butyl-5-(4-methoxybenzylsulfinyl)-4-[4-[2-(1H-tetrazol-5-yl)benzamido]benzyl]-4H-1,2,4-triazole;
(95) 3-n-Butyl-5-(4-methylbenzylthio)-4-[4-[2-(1H-tetrazol-5-yl)benzamido]benzyl]-4H-1,2,4-triazole;
(96) 3-Benzylthio-5-n-butyl-4-[4-[2-(1H-tetrazol-5-yl)benzamido]benzyl]-4H-1,2,4-triazole;
(97) 3-n-Butyl-5-[2-(carbomethoxybenzylthio]-4-[4-[2-(1HH-tetrazol-5-yl)benzamido]benzyl]-4H-1,2,4-triazole;
(98) 3-n-Butyl-5-(2-carboxybenzylthio)-4-[4-[2-(1H-tetrazol-5-yl)benzamido]benzyl]-4H-1,2,4-triazole;
(99) 3-n-Butyl-5-[2-(hydroxymethyl)benzylthio]-4-[4-[2-(1H-tetrazol-5-yl)benzamido]benzyl]-4H-1,2,4-triazole;
(100) 3-n-Butyl-5-[3-(carbomethoxy)benzylthio]-4-[4-[2-(1H-tetrazol-5-yl)benzamido]benzyl]-4H-1,2,4-triazole;
(101) 3-n-Butyl-5-(3-carboxybenzylthio)-4-[4-[2-(1H-tetrazol-5-yl)benzamido]benzyl]-4H-1,2,4-triazole;
(102) 3-n-Butyl-5-[3-(hydroxymethyl)benzylthio]-4-[4-[2-(1H-tetrazol-5-yl)benzamido]benzyl]-4H-1,2,4-triazole;
(103) 3-n-Butyl-5-[4-(carbomethoxy)benzylthio]-4-[4-[2-(1H-tetrazol-5-yl)benzamido]benzyl]-4H-1,2,4-triazole;
(104) 3-n-Butyl-5-(4-carboxybenzylthio )-4-[4-[2-(1H-tetrazol-5-yl)benzamido]benzyl]-4H-1,2,4-triazole;
(105) 3-n-Butyl-5-[4-(hydroxymethyl)benzylthio]-4-[4-[2-(1H-tetrazol-5-yl)benzamido]benzyl ]-4H-1,2,4-triazole;
(106) 3-n-Butyl-5- [α-(carbomethoxy)benzylthio]-4-[4-[2-(1H-tetrazol-5-yl)benzamido]benzyl]-4H-1,2,4-triazole;

(107) 3-n-Butyl-5-(α-carboxybenzylthio)-4-[4-[2-(1H-tetrazol -5-yl ) benzamido]benzyl]-4H-1,2,4-triazole;

(108) 3-n-Butyl-5-[α-(hydroxymethyl)benzylthio]-4-[4-[2-(1H-tetrazol-5-yl)benzamido]benzyl]-4H-1,2,4-triazole;

(109) 3-n-Butyl-4-[[2'-[N-(methanesulfonyl)carbamoyl]biphenyl -4-yl]methyl]-5-(4-nitrobenzylthio)-4H-1,2,4-triazole;

(110) 4-[[2'-[N-(Benzenesulfonyl)carbamoyl]biphenyl-4-yl]methyl]-3-n-butyl-5-(4-nitrobenzylsulfinyl)-4H-1,2,4-triazole;

(111) 3-n-Butyl-4-[[2'-[N-(dimethylsulfamoyl)carbamoyl]biphenyl-4-yl]methyl]-5-(4-methoxybenzylthio)-4H-1,2,4-triazole;

(112) 4-[[2'-(N-Acetylsulfamoyl)biphenyl-4-yl]methyl]-3-n-butyl-5-(4-nitrobenzylthio)-4H-1,2,4-triazole;

(113) 4-[[2'-(N-Benzoylsulfamoyl)biphenyl-4-yl]methyl]-3-n-butyl-5-(4-chlorobenzylsulfinyl)-4H-1,2,4-triazole;

(114) 3-n-Butyl-4-[[2'-[N-(dimethylcarbamoyl)sulfamoyl]biphenyl-4-yl]methyl]-5-(4-methoxybenzylthio)-4H-1,2,4-triazole; and, (115) 3-n-Butyl-5-(4-nitrobenzylthio)-4-[[2'-[N-(2-pyrimidyl)sulfamoyl]biphenyl-4-yl]methyl]-4H-1,2,4-triazole.

The compounds of Formula I can be prepared by a variety of methods typified by those described below. General synthetic methods for 3,4,5-trisubstituted 1,2,4-triazoles are discussed in books or review articles such
   (1) C. Temple and J. A. Montgomery, "Triazoles: 1,2,4" (Vol. 37 of "The Chemistry of Heterocyclic Compounds", A. Weissberger and E. G. Taylor, eds.), Wiley-Interscience, New York, 1981.
   (2) J. B. Polya, in "Comprehensive Heterocyclic Chemistry. The Structure, Reactions, Synthesis and Uses of Heterocyclic Compounds", A. R. Katritzky and C. W. Rees, eds., Vol. 5, Pergamon Press, Oxford, 1984, pp. 733–790.
   (3) J. H. Boyer, in "Heterocyclic Compounds", R. C. Elderfield, ed., Vol. 7, John Wiley & Sons, New York, 1961, pp. 384–461.

In general, the compounds of Formula I are constructed in such a way that $N^1$ and $N^2$ of the triazole ring are derived from hydrazine or a hydrazine derivative, while $N^4$ of the triazole and the 4-(arylmethyl) substituent are derived directly or indirectly from a suitably substituted benzylamine.

Although the reaction schemes described below are reasonably general, it will be understood by those skilled in the art of organic synthesis that one or more functional groups present in a given compound of formula I may render the molecule incompatible with a particular synthetic sequence. In such a case an alternative route, an altered order of steps, or a strategy of protection and deprotection may be employed. In all cases the particular reaction conditions, including reagents, solvent, temperature, and time, should be chosen so that they are consistent with the nature of the functionality present in the molecule.

The Reaction Schemes below have been generalized for simplicity. It is to be understood that the "ARCH$_2$" substituent present at $N^4$ of the triazole derivatives or in their precursors is any substituted arylmethyl moiety consistent with the definition of the $N^4$ substituent in Formula I or which may be transformed to such a grouping either before or after the assembly of the triazole ring system. Such transformations may involve protection and/or deprotection, formation of the "X" linkage between the two aromatic rings as shown in formula I, or other modifications. It is also to be understood that in most of the Reaction Schemes, the "ARCH$_2$" (Ar=aryl) substituent may be replaced by the homologous "Ar(CH$_2$)$_2$" group as consistent with the definition of Formula I.

It is further to be understood that in the generalized schemes below that unless specified further in the text, the groups R and R' represent functionalized or unfunctionalized alkyl, aryl, heteroaryl, aralkyl, and the like, while At' represents a functionalized or unfunctionalized aryl or heteroaryl group. The moiety R'X represents an alkylating agent in which R' is typically a functionalized or unfunctionalized alkyl or aralkyl group, while X is a leaving group such as chloro, bromo, iodo, methanesulfonate, or p-toluenesulfonate.

SCHEME 1

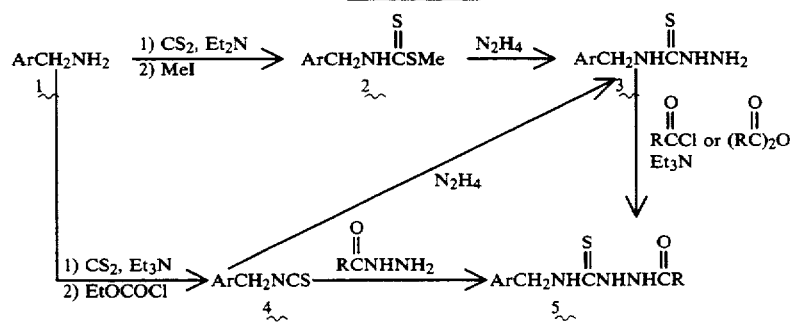

SCHEME 1
-continued

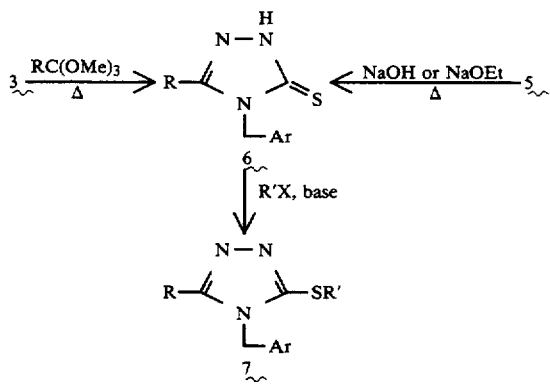

Scheme 1 outlines some of the most widely applicable routes to compounds of formula I in which either the 3- or 5-substituted is substituted thio. Thus an appropriate benzylamine 1 may be converted to dithiocarbamate ester 2 in a one-pot two-step sequence involving treatment with carbon disulfide in the presence of a base such as triethylamine followed by alkylation with methyl iodide. Treatment of 2 with hydrazine (preferably in excess) affords the 4-substituted thiosemicarbazide 3. This is also readily obtained upon reaction of hydrazine with the isothiocyanate 4, which in turn is prepared from amine 1 [for example, via an intermediate carbethoxy dithiocarbamate (J. E. Hodgkins and M. G. Ettlinger, *J. Org. Chem.*, 21, 404 (1956)) or by one of the other methods known in the literature]. The acylthiosemicarbazide 5 may be prepared either by reaction of 3 with the appropriate acid chloride or anhydride or by addition of an acid hydrazide (readily obtained from the corresponding ester) to the isothiocyanate 4. As described in G. F. Duffin, J. D. Kendall, and H. R. J. Waddington, *J. Chem. Soc.*, 3799 (1959), S. M. El-Khawass and N. S. Habib, *J. Heterocyclic Chem.*, 26, 177 (1989), and numerous other papers, acylthiosemicarbazides related to 5 can by cyclized in the presence of hydroxide or alkoxide to the mercaptotriazoles (best represented as triazolinethiones) corresponding to 6. Compounds of type 6 can also be prepared by direct reaction of the thiosemicarbazide derivative 3 with an appropriate acid derivative. For example, reaction of 3 with a trimethyl orthoester at elevated temperature in a suitable solvent (such as 2-methoxyethanol at reflux) yields 6. Similar syntheses of mercaptotriazoles have been reported by G. A. Reynolds and J. A. Van Allan, *J. Org. Chem.*, 24, 1478 (1959). Other acid derivatives such as esters [in the presence of alkoxide: M. Pesson, G. Polmanss, and S. Dupin, Compt. Rend., 24.8, 1677 (1959)]and selenoesters [V. I. Cohen, *J. Heterocyclic Chem.*, 15,237, (1978)]have also been reported to react with 4-substituted thiosemicarbazides to give mercaptotriazoles analogous to 6. In certain instances the carboxylic acid itself may be used. Thus, 4-substituted thiosemicarbazides have been reacted with trifluoroacetic acid at elevated temperature to give mercaptotriazoles analogous to 6 (R=$CF_3$) [T. Cebalo, U.S. Pat. No. 3,625,951 (1971) and E. I. Aoyagi, U.S. Pat. No. 4,477,459 (1984)].

The S-alkylated mercaptotriazoles of structure 7 are obtained by treatment of the triazolinethione 6 with an appropriate alkylating agent R' X in which R' is functionalized or unfunctionalized alkyl, aralkyl, heterocyclyl, or the like, and X is a leaving group such as chloro, bromo, iodo, methanesulfonate, or p-toluenesulfonate. This alkylation is conducted in any of a variety of solvents (including methanol, ethanol, 2-methoxyethanol, tetrahydrofuran, N,N-dimethylformamide, dichloromethane and water, depending on the properties of the particular substituents) in the presence of a base (such as a trialkylamine, alkoxide, or hydroxide). Triazolinethiones (mercaptotriazoles) are known to give the S-alkylated derivatives predominantly if not exclusively under basic conditions (see, for examples, C. Temple and J. A. Montgomery, "Triazoles: 1,2 4", Wiley-Interscience, New York, 1981, pp. 251-258). The alkylation reaction is generally run at a temperature of from 0° C. to 125° C., depending on the reactivity of the alkylating agent.

The triazolinethiones 6 may be prepared by alternative routes. In the method of F. Malbec, R. Milcent, and G. Barbier [*J. Heterocycl. Chem.*, 21, 1689 (1984)] (Scheme 2), the imidate hydrochloride 8 is reacted with thiosemicarbazide at ambient temperature to give the ester thiosemicarbazone 9. The conversion of 9 to the triazolinethione 6 can be effected by heating with amine 1 in DMF at reflux. Similarly, an $N^4$ substituted ester thiosemicarbazone 9a, which is obtained by reaction of 8 with 3, can be cyclized to 6 by heating it in the presence of a base; e.g., 1,8-diazabicyclo[5.4.0]undec-7-ene (DBU) in a solvent such as tetrahydrofuran.

SCHEME 2

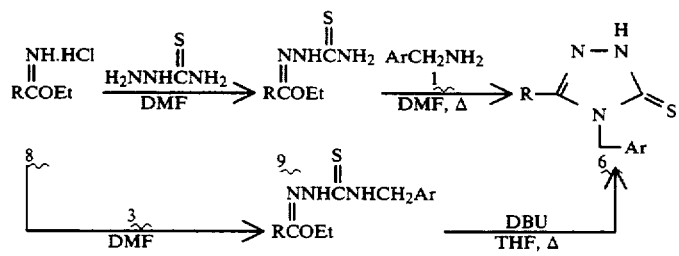

For triazolinethiones of type 6 where R=aryl, the method of T. Radha Vakula, V. Ranga Rao, and V. R. Srinivasan [*Indian J. Chem.*, 7, 577 (1969)](Scheme 3) is applicable. Thus the thiosemicarbazide derivative 3 is condensed with an aromatic aldehyde 10 to give the thiosemicarbazone 11. Upon treatment of 11 with bromine in acetic acid, the triazolinethione 12 is formed.

SCHEME 3

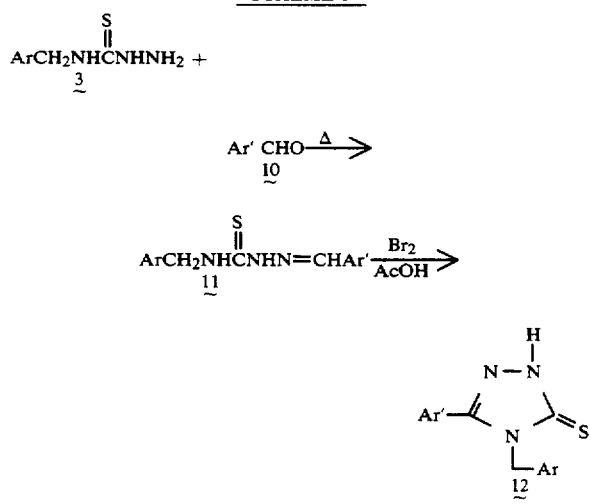

Following the method of L. Strzemecka [*Polish J. Chem.*, 57, 561 (1983] (Scheme 4), reaction of an amidrazone 13 with the isothiocyanate 4 in ethanol at reflux gives triazolinethione 6.

SCHEME 4

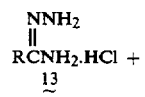

-continued
SCHEME 4

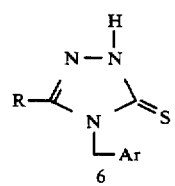

Certain S-substituted mercaptotriazoles of formula 7 which may not be accessible by the reactions of Scheme 1 (especially R'=aryl) can be prepared by an alternative route (Scheme 5) involving displacement of a leaving group on the triazole by an appropriate thiol. Treatment of the triazolinethione 6 with chlorine under anhydrous conditions in a solvent such as chloroform or dichloromethane gives as a major product the chlorotriazole 14 [D. S. Deshpande, T. G. Surendra Nath, and V. R. Srinivasan, *Indian Chem J. Chem.*, 13,852 (1975)]. In addition, the synthesis of chlorotriazoles by $POCl_3/PCl_5$ treatment of the corresponding triazolinone has been reported [S. Naqui and V. R. Srinivasan, *J. Sci. Industr. Res.*, 21B, 195 (1962). Reaction of 14 with a thiophenol or other thiol in the presence of a base such as N,N-diisopropylethylamine at elevated temperature (for example, in DMF at reflux) gives 7. Similar reactions have been reported by H. Becker and K. Wehner, British Patent 1,157,256 (1969). Alternatively, the methylthiotriazole 15 may be prepared (by alkylation of 6 with methyl iodide) and then oxidized to the methylsulfone 16 using hydrogen peroxide in acetic acid or similar methods. Displacement of the methanesulfonyl group of 16, like the chloro group of 14, by R'SH in the presence of a base affords 7, especially for R'=aryl. The preparation of a methanesulfonyltriazole analogous to 16 and its nucleophilic displacement have been reported by E. B. Akerblom and D. E. S. Campbell, *J. Med. Chem.*, 16, 312 (1973).

SCHEME 5

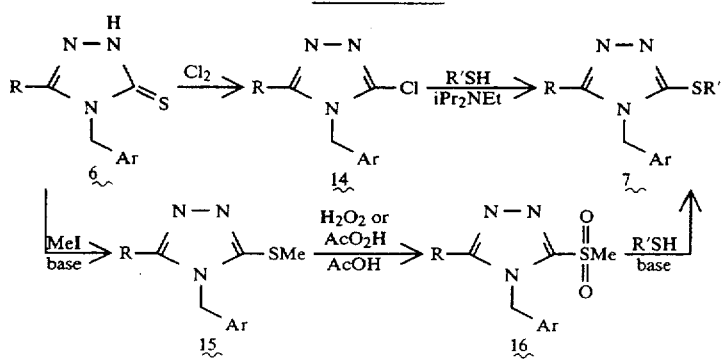

SCHEME 6

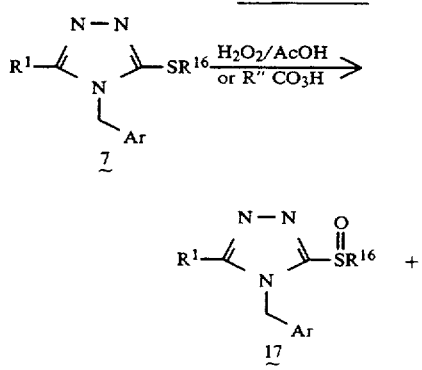

The S-substituted mercaptotriazoles 7 can be converted to the corresponding sulfoxides 17 and/or sulfone 18 by oxidation with various reagents such as hydrogen peroxide in acetic acid or a suitable peracid. Reactions of this type have been described by E. B. Akerblom and D. E. S. Campbell (see reference above). Whether 17 or 18 is the primary or exclusive product depends on the stoichiometry of the reagents, reaction time, and temperature.

SCHEME 7

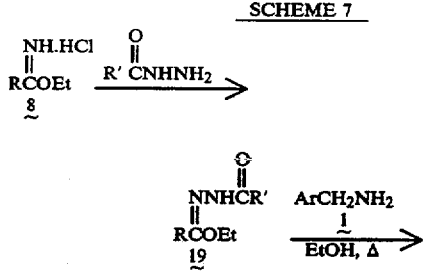

-continued
SCHEME 7

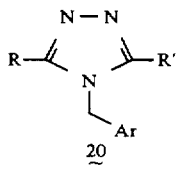

The method of R. Kraft, H. Paul, and G. Hilgetag [*Chem. Ber.*, 101, 2028 (1968)] (Scheme 7) is useful for preparing triazoles of structure 20 in which R' is aryl or heterocyclic. Treatment of the imidate hydrochloride 8 with an appropriate hydrazide (typically at −10° to 5° C.) gives the adduct 19, which can be reacted with the amine 1 and cyclized to the triazole 20 upon heating in ethanol. An adaptation of this method [M. Pesson, et al., *Bull. Soc. Chim. Fr.* 1590 (1970)] is used to prepare triazolecarboxamides of type 20 wherein R¹=CONR"R"'.

SCHEME 8

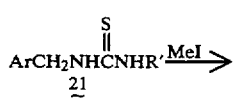

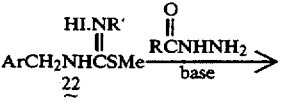

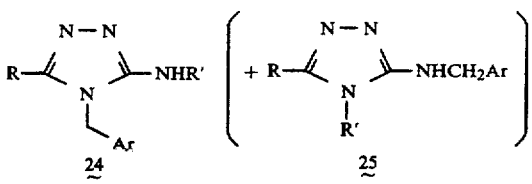

Aminotriazoles of formula 24 can be prepared as shown in Scheme 8. An analogous route has been reported by E. Akerblom, *Acta Chem. Scand.*, 19, 1135

(1965). Reaction of the isothiocyanate 4 with an appropriate amine gives the thiourea 21, which is alkylated with methyl iodide to give the isothiourea hydriodide 22. The acylaminoguanidine 23, obtained by reaction of 2% with a hydrazide in the presence of base, can be thermally cyclized to 24, which is separated from the isomeric byproduct 25. Modest yields of aminotriazoles analogous to 24 have also been obtained by direct thermal reaction of intermediates analogous to 22 with a hydrazide [L. Carey, B. J. Price, J. W. Clitherow, J. Bradshaw, M. Martin-Smith, D. E. Bays, and P. Blatcher, U.S. Pat. No. 4,481,199 (1984)].

aldehyde to give the Schiff base 29. Reduction of 29 with a suitable reducing agent such as sodium borohydride gives 30. Related synthesis of benzylaminotriazoles have been reported by Reiter [J. Reiter, T. Somorai, P. Dvortsak, and Gy. Bujtas, *J. Heterocycl. Chem.*, 22. 385 (1985) and J. Reiter, L. Pongo, and P. Dvortsak, J. Heterocycl. Chem., 24, 127 (1987)].

SCHEME 11

SCHEME 9

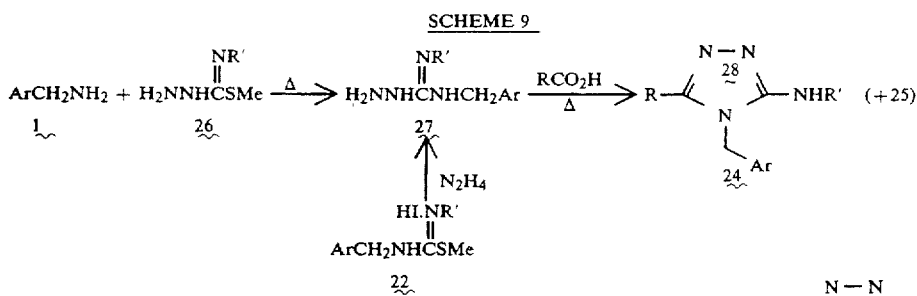

In another route (Scheme 9) following a sequence reported by L. Carey, et al., U.S. Pat. No. 4,481,199 (see above), amine 1 is heated with the S-methyl thiosemicarbazide derivative 26 to give the aminoguanidine 27. Heating 27 with an appropriate carboxylic acid provides the aminotriazole 24, which is separated from the isomer 25 if present. Similar chemistry has been reported by C. F. Kröger, G. Schoknecht, and H. Beyer, Chem, Ber,, 97,396 (1964), R. G. W. Spickett and S. H. B. Wright, British Patent 1,070,243 (1967), and G. J. Durant, G. M. Smith, R. G. W. Spickett, and S. H. B. Wright, *J. Med. Chem.*, 9, 22 (1966). This last paper also describes the synthesis of aminoguanidines analogous to 27 by hydrazine treatment of isothioureas corresponding to 22 (see Scheme 8).

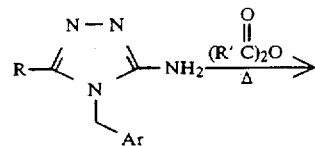

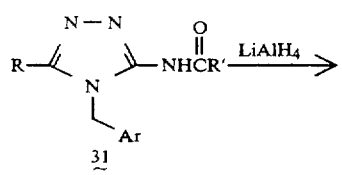

SCHEME 10

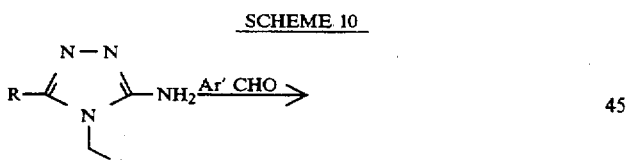

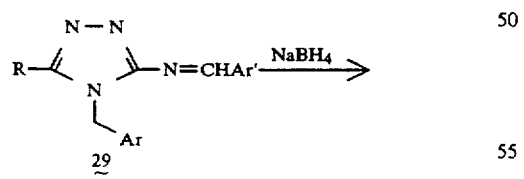

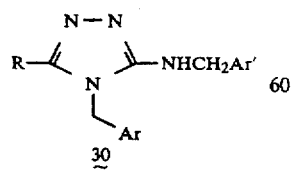

A useful route to certain N-(arylmethyl) aminotriazoles 30 is shown in Scheme 10. The aminotriazole 28 (equivalent to 24, R'=H), which can be prepared by Scheme 8 or Scheme 9 is condensed with an aromatic

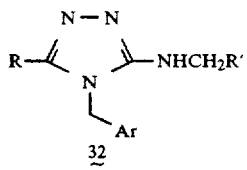

Following the methods of R. G. Harrison, W. B. Jamison, W. J. Ross, and J. C. Saunders, Australian Patent Specification 518,316, aminotriazoles of structure 28 can be heated with an acid anhydride to give the acylaminotriazoles 31. These can be reduced with lithium aluminum hydride to give the N-substituted aminotriazoles of formula 32.

SCHEME 12

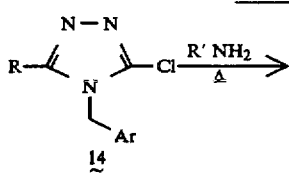

-continued
SCHEME 12

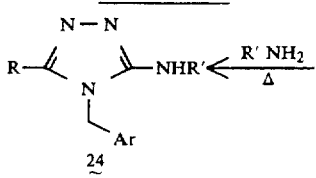

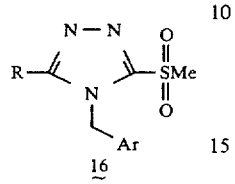

Aminotriazoles of structure 24 can also be obtained by heating a chlorotriazole 14 or a methanesulfonyltriazole 16 with an amine. Amine displacements on chlorotriazoles have been reported by H. G. O. Becker and V. Eisenschmidt, Z. Chem., 8, 105 (1968) and H. Becker and K. Wehner, British Patent 1,157,256 (1969).

SCHEME 13

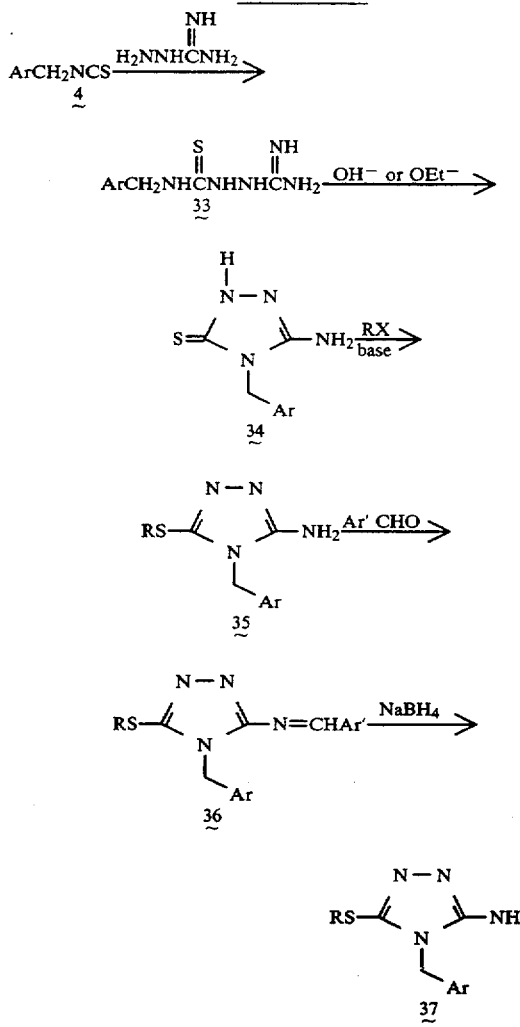

Aminomercaptotriazoles of structure 37 can be prepared as outlined in Scheme 13, which utilizes the chemistry of L. E. Godfrey and F. Kurzer, J. Chem. Soc. 5137 (1961), J. Reiter, T. Somorai, P. Dvortsak, and Gy. Bujtas, J. Hetetocycl. Chem., 22, 385 (1985), and J. Reiter, L. Pongo, and P. Dvortsak, J. Heterocyclic Chem., 24, 127 (1987). Reaction of the isothiocyanate 4 with aminoguanidine gives 33, which can be cyclized in the presence of base to the aminotriazolinethione 34. Alkylation of 34 in the presence of base yields the 5-substituted derivative 35. Further transformations to the Schiff base 36 and then to 37 are as in Scheme 10,

SCHEME 14

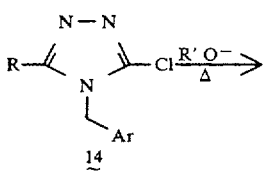

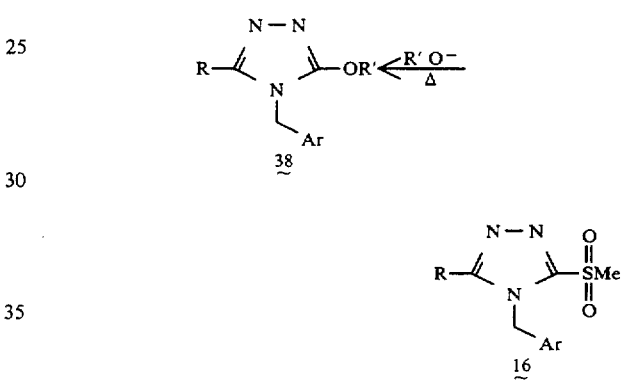

Alkoxy and aryloxytriazoles of formula 38 can be prepared by heating a chlorotriazole 14 or a methanesulfonyl triazole 16 with the appropriate alkoxide or phenoxide anion. Such a transformation has been described by E. B. Akerblom and D. E. S. Campbell, J. Med. Chem., 16, 312 (1973).

SCHEME 15

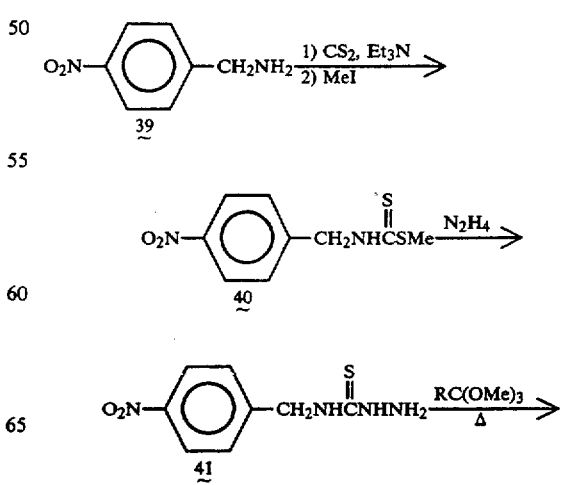

SCHEME 15 -continued

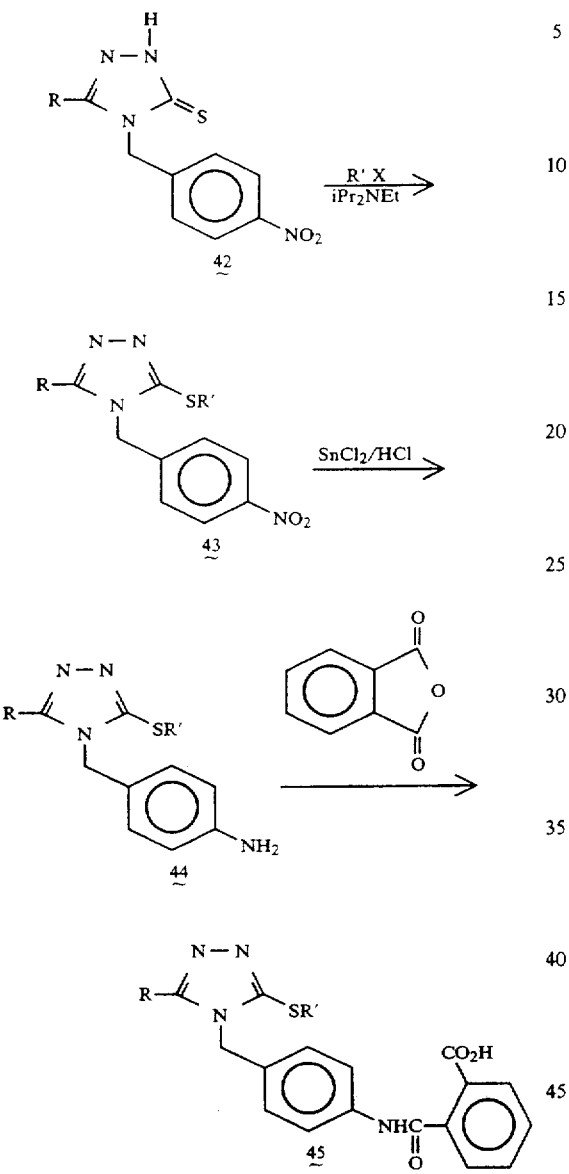

SCHEME 16

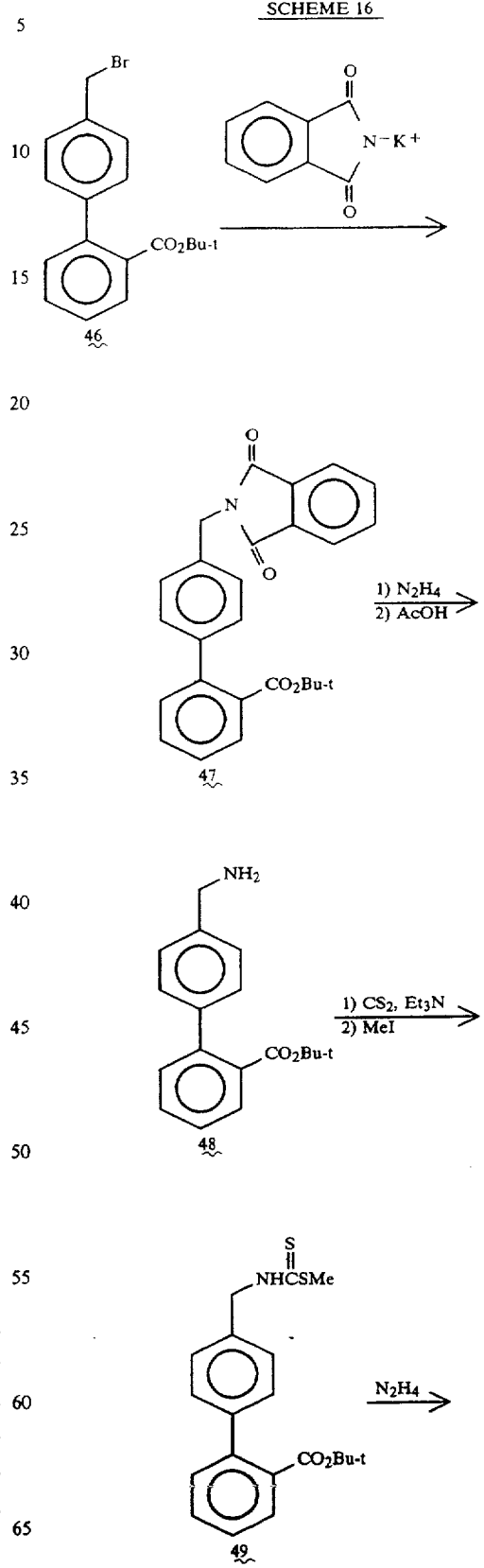

The elaboration of the 4-(2-carboxybenzamido)benzyl substituted at the 4-position of a 1,2,4-triazole is shown in Scheme 15. Using the methods of Scheme 1, 4-nitrobenzylamine is successively converted to the methyl dithiocarbamate 40, the thiosemicarbazide 41, the triazolinethione 42, and the S-alkylated mercaptotriazole 43. Reduction of the nitro group, preferably with stannous chloride in the presence of hydrochloric acid at 0°–25° C. gives the amine 44. Treatment of 44 with phthalic anhydride at room temperature in a suitable solvent such as anhydrous tetrahydrofuran yields the phthaloyl derivative 45.

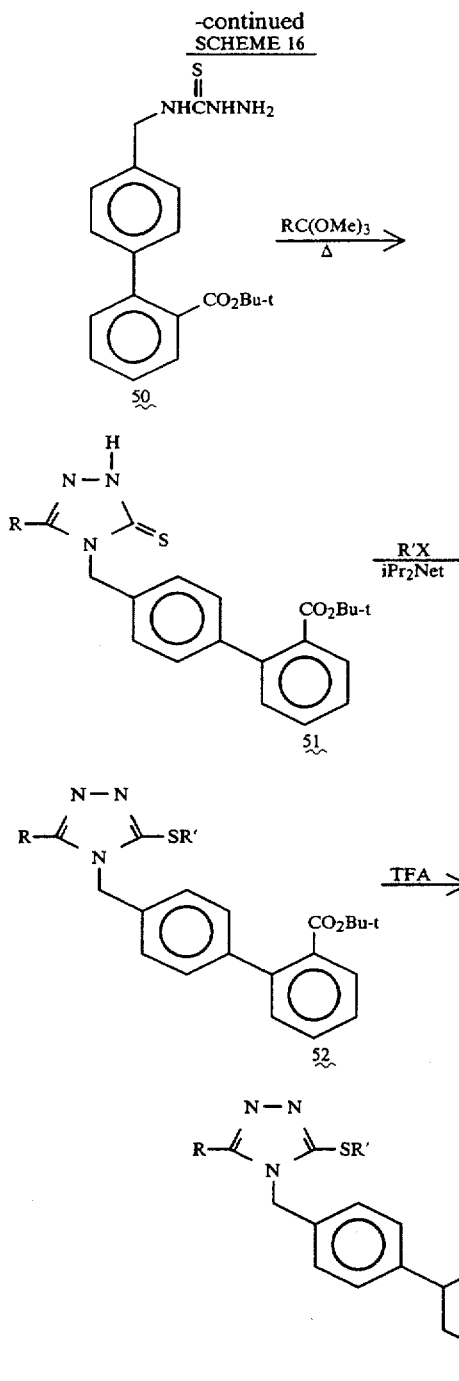

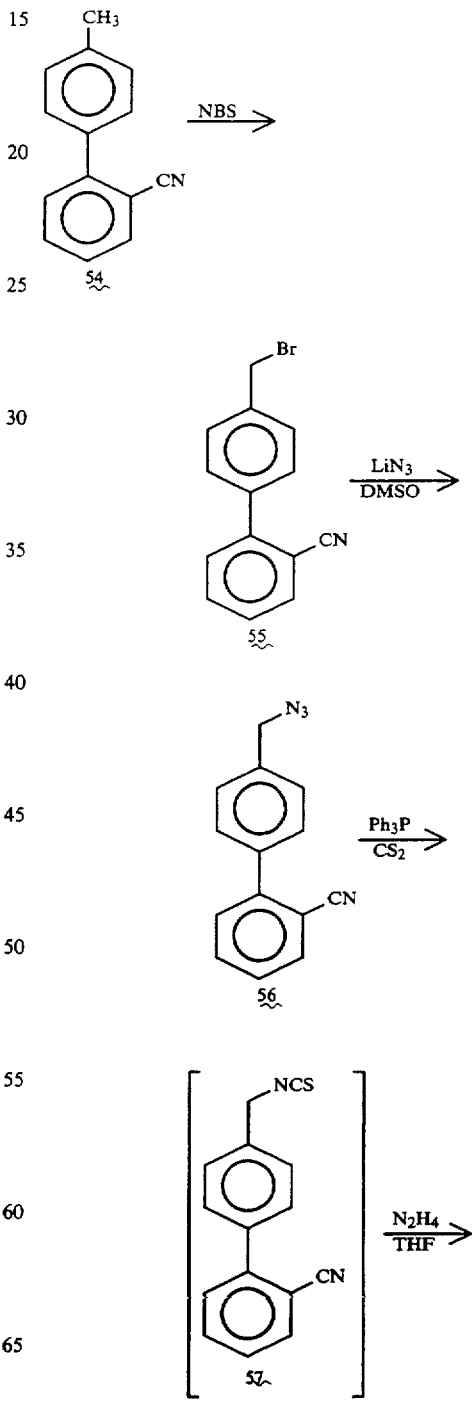

by other methods known in the literature. Following the procedures of Scheme 1, 48 is converted sequentially to the methyl dithiocarbamate 49, the thiosemicarbazide 50, the triazolinethione 51, and the S-alkylated mercaptotriazole 52. Deprotection of the t-butyl ester to give the free acid 53 is achieved by treatment of 52 with trifluoroacetic acid at room temperature.

The incorporation of the (2'-carboxybiphenyl-4-yl)methyl substituent into a 1,2,4-triazole at the 4-position is outlined in Scheme 16. The starting material, 4-bromomethyl-2'-(t-butoxycarbonyl)biphenyl (46), can be prepared as described in European Patent Application 253,310 (or in Merck Case No. 17930 filed 5/15/89). Treatment of 46 with potassium phthalimide at room temperature in a suitable solvent such as N,N-dimethylformamide gives the phthalimido product (47), which is converted to the amine 48 by a standard hydrazinolysis procedure. Alternatively, using the methods described in EP 253,310, 46 may be treated with sodium azide in dimethylformamide, and the resulting azido intermediate may be reduced to the amine 48 by hydrogenation in the presence of a palladium catalyst or

31

-continued
SCHEME 17

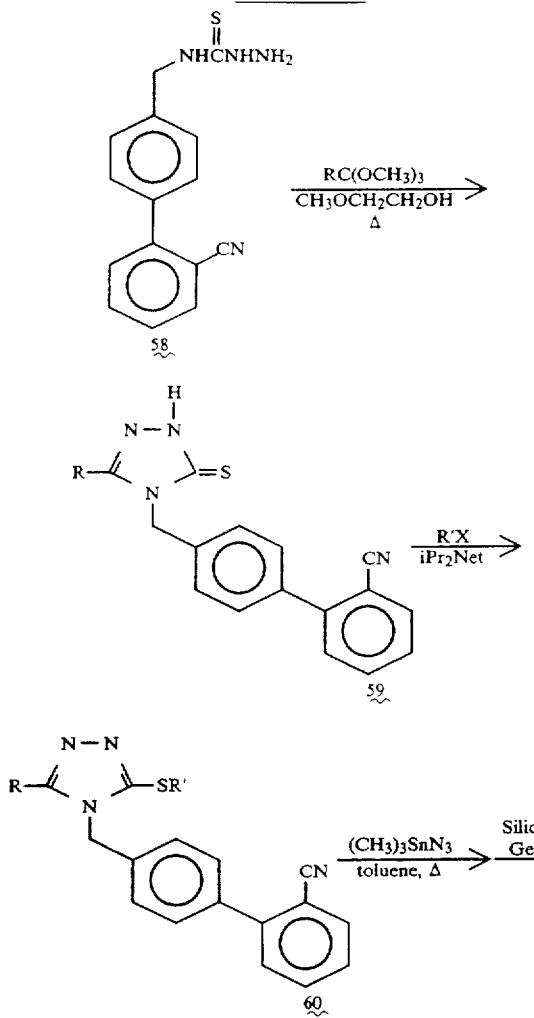

32

-continued
SCHEME 17

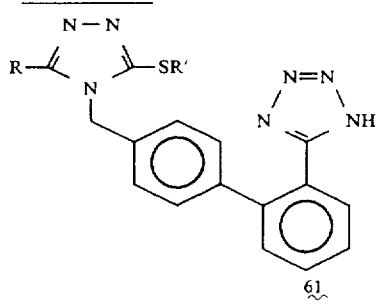

Incorporation of a [2'-(1H-tetrazol-5-yl)biphenyl-4-yl]methyl substituent into a 1,2,4-triazole at the 4-position is outlined in Scheme 17. The starting material, 4-methyl-2'-cyanobiphenyl (54), is described in EP 253,310 or may be prepared by nickel or palladium-catalyzed coupling of p-tolylzinc chloride with 2-bromobenzonitrile as described in U.S. Ser. No. 351,508 filed May 15, 1989. Bromination of 54 with N-bromosuccinimide as described in EP 253,310 gives the bromomethyl derivative 55, and this is converted to the azide 56 using an alkali metal azide such as lithium azide in a suitable solvent such as dimethyl sulfoxide at room temperature. Conversion of 56 to the isothiocyanate 57 is carried out using triphenylphosphine and carbon disulfide (O. Tsuge, S. Kanemasa, and K. Matsuda, *J. Org. Chem.*, 49, 2688(1984)). This product is not purified but is treated directly with hydrazine hydrate in a solvent such as tetrahydrofuran to give the thiosemicarbazide 58. Ring closure to the triazolinethione derivative 59 is accomplished using a trimethyl orthoester such as trimethyl orthovalerate in a suitable solvent such as 2-methoxyethanol at a elevated temperature. This derivative is treated with an appropriate alkylating agent R'X (as described in Scheme 1) in the presence of a non-nucleophilic base such as N,N-diisopropylethylamine in a suitable solvent such as 2-methoxyethanol to give the S-alkylated product 60. Conversion of the nitrile 60 to the required tetrazole product 61 can be accomplished using trimethyltin azide at elevated temperature in a suitable solvent such as toluene or xylene according to methods described in EP 291,969, followed by destannylation in the presence of silica gel.

SCHEME 18

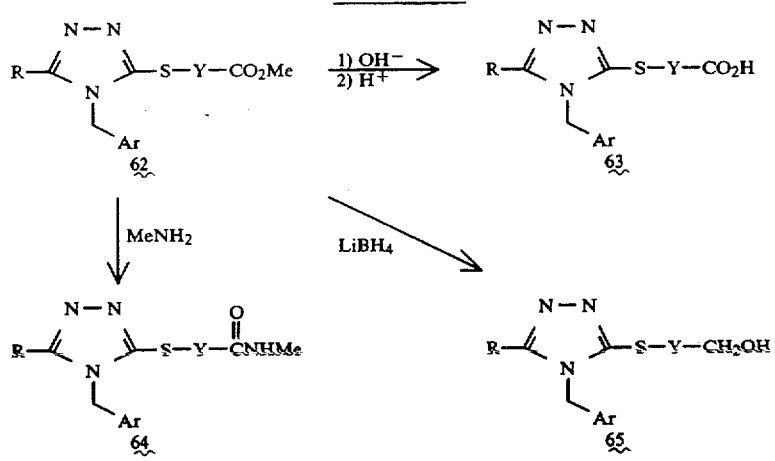

wherein Y represents an alkyl, aryl, or aralkyl group bearing the designated substituent (i.e., carbomethoxy, carboxy, etc.).

Further transformations of substituent functional groups can be carried out after assembly of the triazole ring and either before or after full elaboration of the arylmethyl substituent at $N^4$. Typical examples are shown in Scheme 18. Thus the methyl ester of 62 can be saponified by treatment with aqueous sodium hydroxide (optionally in the presence of a cosolvent such as alcohol, tetrahydrofuran, or dioxane) at room temperature to give, after acidification, the acid 63. The N-methyl amide 64 is readily obtained by reaction of 62 with excess aqueous methylamine at room temperature in the presence of a cosolvent such as methanol. Reduction of the methyl ester 62 to the hydroxymethyl derivative 65 can can be accomplished by treatment with lithium borohydride in a solvent such as tetrahydrofuran. These examples are in no way exclusive of other substituent functional group transformations which can be accomplished after formation of the 4H-1,2,4-triazole system.

SCHEME 19

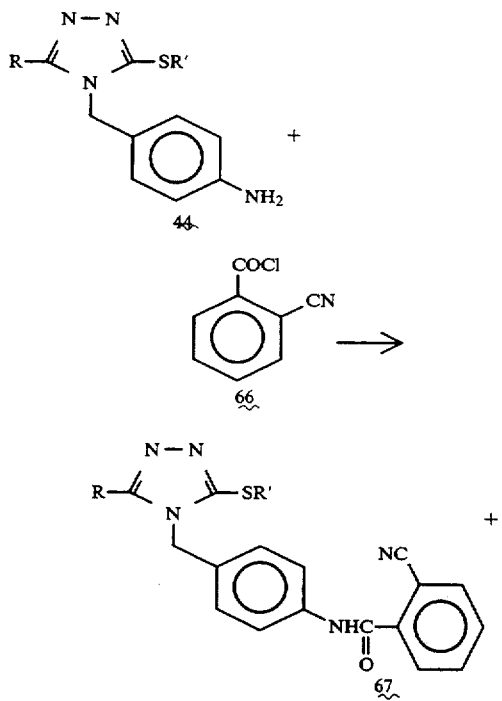

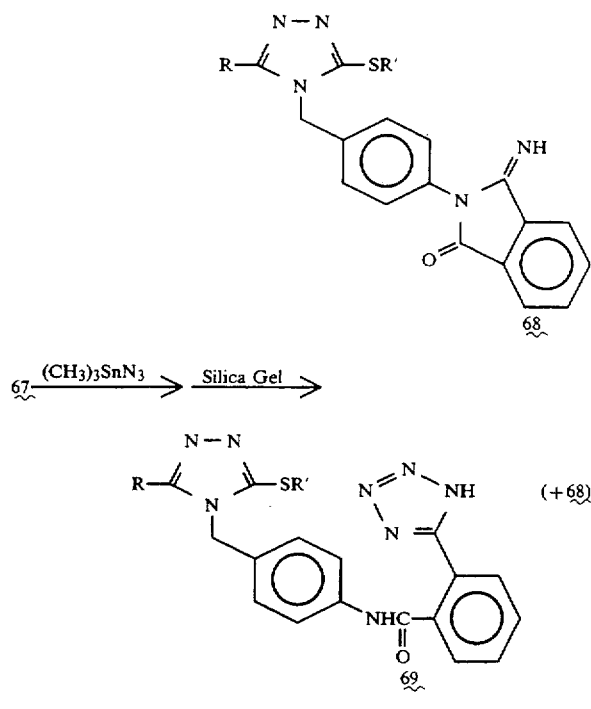

Scheme 19 outlines a typical preparation of triazoles substituted at $N^4$ with a 4-[2'-(1H-tetrazol-5-yl)benzamido]benzyl side chain. Treatment of the amino intermediate 44 (from Scheme 15) with 2-cyanobenzoyl chloirde 66 yields the 2-cyanobenzamide 67, which can be chromatographically separated from the cyclic by-product 68. Conversion of the nitrile 67 to the tetrazole 69 is accomplished by heating 67 with trimethyltin azide, followed by destannylation with silica gel. Additional quantities of the by-product 68 are formed during the trimethyltin azide reaction, but the desired product 69 can be separated from 68 by chromatography.

SCHEME 20

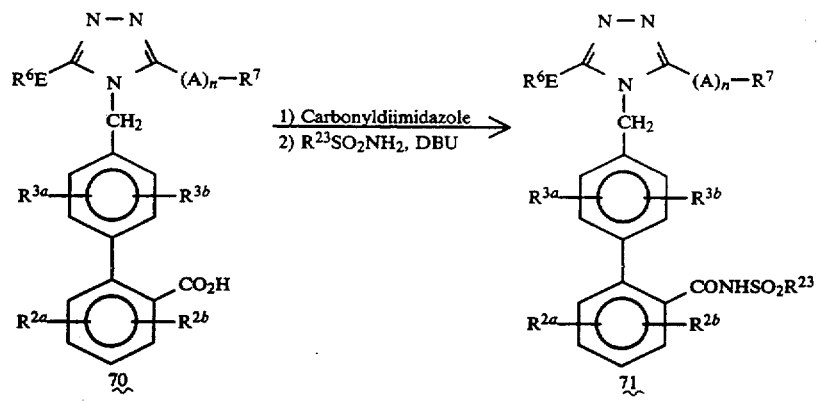

-continued
SCHEME 20

Alternative Methods a. (i) SOCl$_2$, Δ
(ii) R$^{23}$SO2NH$^-$M$^+$ (where M is Na or Li)

b. (i) (COCl$_2$)—DMF, −20° C.
(ii) R$^{23}$SO2NH$^-$M$^+$ c. (i) N-(N,N-Diphenylcarbamoyl)pyridinium chloride/aq. NaOH
(ii) R$^{23}$SO$_2$NH$^-$M$^+$ Compound of formula (I) wherein R$^1$ is —CONHSO$_2$R$^{23}$ (where R$^{23}$ is substituted or unsubstituted alkyl, aryl, or heteroaryl) may be prepared from the corresponding carboxylic acid derivatives (70) as outlined in Scheme 20. The carboxylic acid 70, obtained as described in Scheme 16 and other schemes, can be converted into the corresponding acid chloride by treatment with thionyl chloride at reflux or, preferably, with oxalyl chloride and a catalytic amount of dimethylformamide at low temperature [A. W. Burgstahler, et al., Synthesis, 767 (1976)]. The acid chloride can then be treated with the alkali metal salt of R$^{23}$SO$_2$NH$_2$ to form the desired acylsulfonamide 71. Alternatively, 71 may be prepared from 70 using N,N-diphenylcarbamoyl anhydride intermediates [F. J. Brown, et al., European Patent Application EP 199,543; K. L. Shepard and W. Halczenko, J. Heterocycl. Chem., 16, 321 (1979)]. Preferably, the carboxylic acid 70 is treated with carbonyldiimidazole to give an acyl-imidazole intermediate, which can then be treated with an appropriate aryl- or alkylsulfonamide in the presence of 1,8-diazabicyclo[5.4.0]undec-7-ene (DBU) to give the desired acylsulfonamide 71.

SCHEME 21

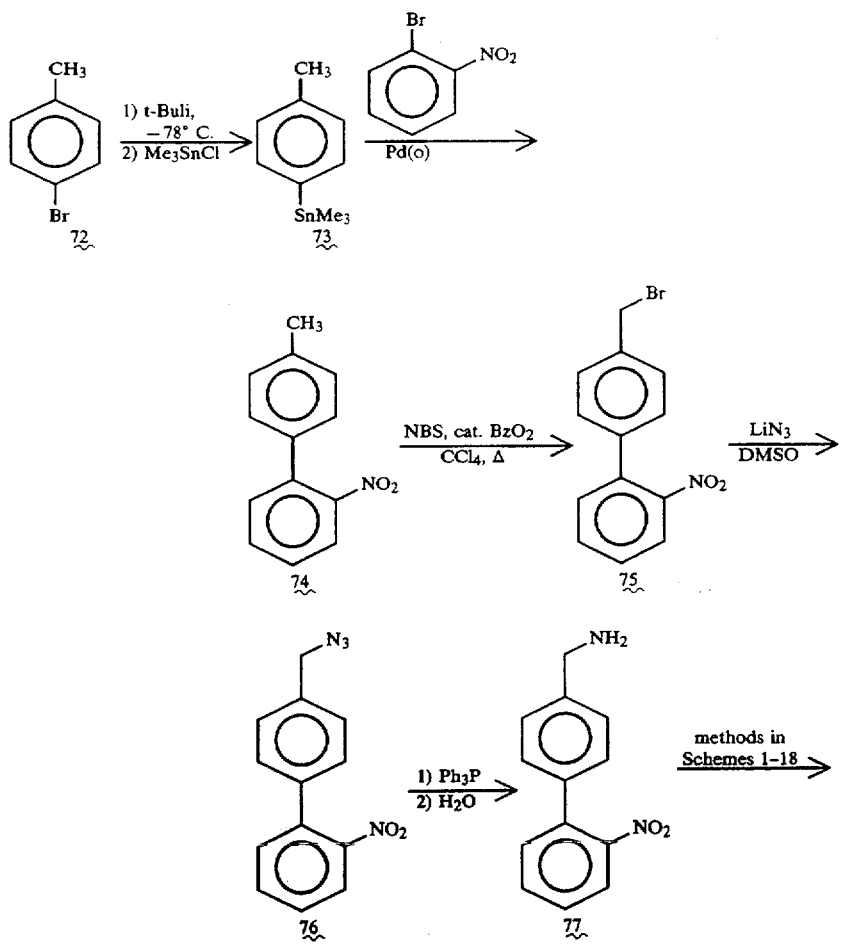

-continued
SCHEME 21

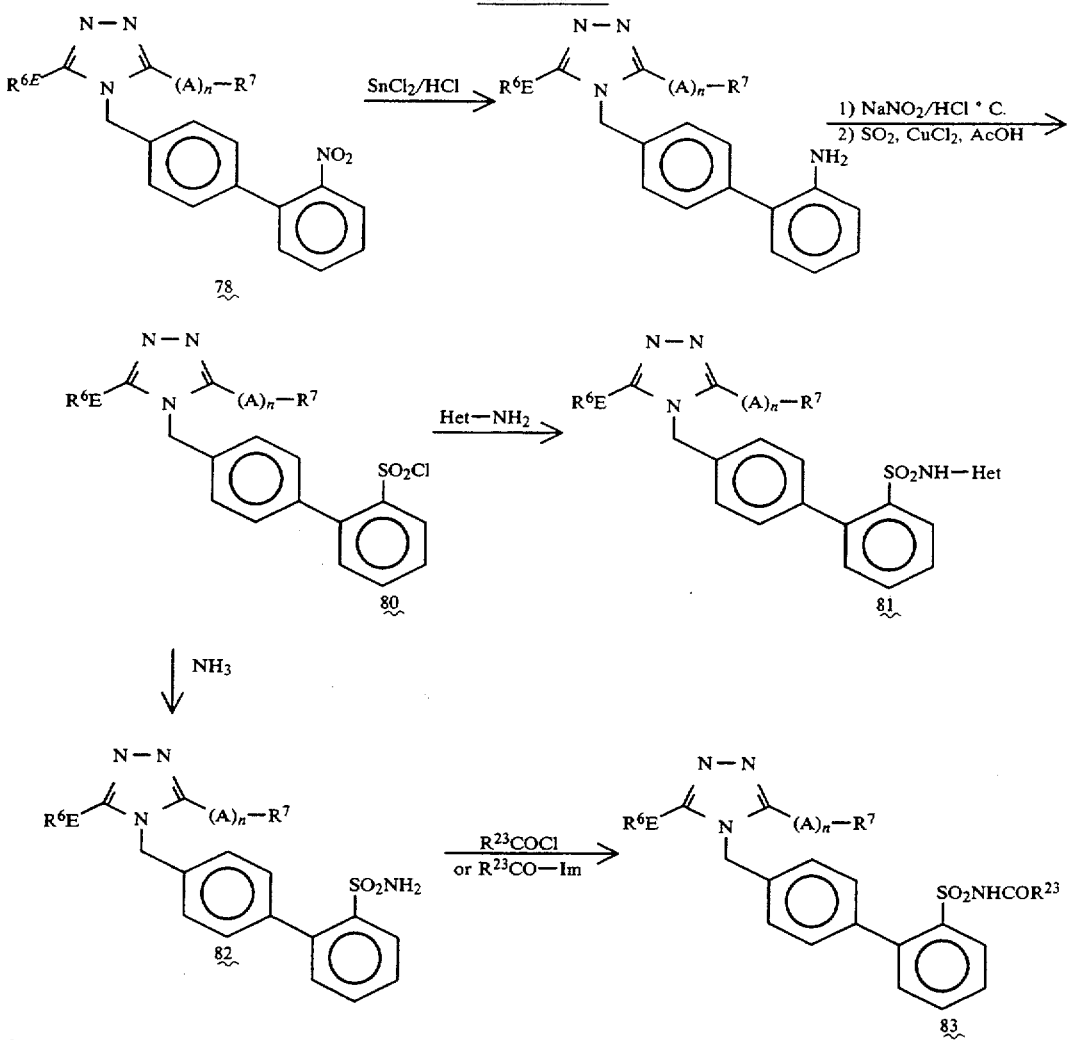

where
NBS = N-bromosuccinimide
Bz = benzoyl
Het = heteroaryl
Im = 1-imidazolyl.

The preparation of compounds of formula (I) wherein $R^1$ is —$SO_2NHCOR^{23}$ is outlined in Scheme 21. p-Bromotoluene (72) is converted to the trimethylstannane derivative 73 [S. M. Moerlein, *J. Organometal. Chem.*, 319, 29 (1987)], which may be coupled with o-bromonitrobenzene in the presence of $(Ph_3P)_4Pd$ or $(Ph_3P)_2PdCl_2$ catalyst to give the biphenyl derivative 74. Such couplings have been described by J. K. Stille, *Pure Appl. Chem.*, 57, 1771 (1985); T. R. Bailey, *Tetrahedron Lett.*, 27, 4407 (1986); and D. A. Widdowson and Y.-Z. Zhang, *Tetrahedron*, 42, 2111 (1986). Bromination of 74 with N-bromosuccinimide in the presence of catalytic benzoyl peroxide gives 75, which upon treatment with lithium azide in DMSO yields the azido derivative 76. Reduction of 76 to the amine 77 may be accomplished by treatment with triphenylphosphine followed by water. In an alternative route, the bromo group of 75 may be displaced by potassium phthalimide. Hydrazinolysis of the phthalimide derivative yields 77.

By the methods described in the previous schemes, the amine 77 can be converted to a variety of triazoles of the general formula 78. Reduction of the nitro group of 78, preferably with stannous chloride/hydrochloric acid gives the amino derivative 79. Diazotization of the amine 79 and reaction of the diazonium salt with sulfur dioxide in the presence of cuptic chloride affords the corresponding arylsulfonyl chloride 80 [see H. Meerwein, et al., *Chem. Ber.*, 90,841 (1957); A. J. Prinsen and H. Cerfontain, *Rec. Tray. Chim.*, 84, 24 (1965); E. E. Gilbert, *Synthesis*, 3 (1969); and references cited therein]. Treatment of the sulfonyl chloride 80 with an appropriate heteroaryl amine provides the N-heteroaryl sulfonamide 81. Reaction of the sulfonyl chloride with ammonia yields the sulfonamide 82, which is then treated with an appropriate acylating agent (such as an acid chloride, a carbamoyl chloride, or an acylimidazole derivative) to give the acylsulfonamide product 83.

SCHEME 22

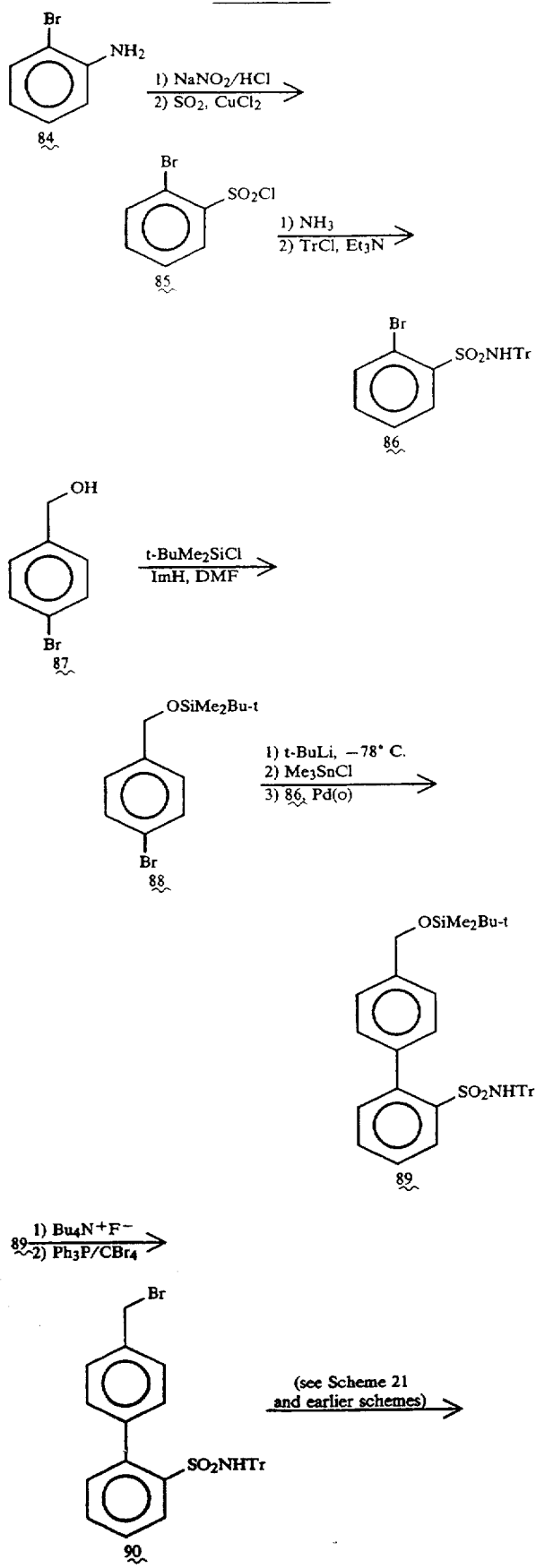

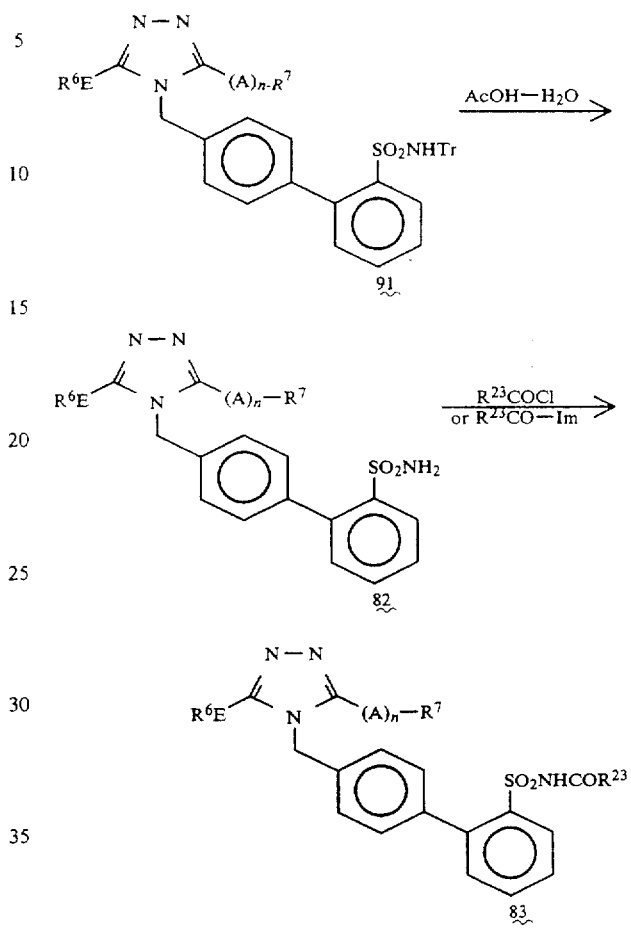

where
Tr = trityl (i.e., triphenylmethyl)
Im = 1-imidazolyl.

Scheme 22 shows an alternative sequence leading to 83 in which a protected sulfonamide is present at the time of the biaryl coupling. By the methods described above, o-bromoaniline (84) is converted to the corresponding sulfonyl chloride 85. Treatment of 85 with ammonia and then with trityl chloride in the presence of triethylamine yields the N-trityl sulfonamide 86. p-Bromobenzyl alcohol (87) is t-butyldimethylsilylated, and the resulting 88 is coupled with 86 under the conditions described above to give the biphenyl product 89. The silyl group is removed with tetrabutylammonium fluoride, and treatment of the alcohol with triphenylphosphine/carbon tetrabromide gives the bromo derivative 90. Using the methods of Scheme 21 and earlier schemes, 90 may be transformed into a variety of triazoles of the general formula 91. The trityl protecting group is removed with aqueous acetic acid to give the free sulfonamide 82 which is acylated to yield the target 83 as in Scheme 21.

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lyeins, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of A II at the receptors. In order to identify A II antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml), homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear](10 μl; 20,000 cpm) with or without the test sample and the mixture was incubated at 37° C. for 90 minutes. The mixture was then diluted with ice-cold 50 mM Tris-0.9% NAGl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as A II antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10μl) with or without the test sample and the mixture was incubated at 37° C. for 1 hour. The mixture was then diluted with Tris buffer (4ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

The potential antihypertensive effects of the compounds described in the present invention may be evaluated using the methodology described below: Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volume—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention were evaluated and were found to exhibit an activity of at least $IC_{50} < 50\mu M$ thereby demonstrating and confirming the utility of the compounds of the invention as effective A II antagonists.

Thus, the compounds of the invention are useful in treating hypertension. They are also of value in the management of acute and chronic congestive heart failure, in the treatment of secondary hyperaldosteronism, primary and secondary pulmonary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the the compounds of this invention for these and similar disorders will be apparent to those skilled in the art.

The compounds of this invention are also useful to treat elevated intraocular pressure and can be administered to patients in need of such treatement with typical pharmaceutical formulation such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered in patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, resetpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delaprilhydrochloride, enalapril, enalaprilat, fosinoprilsodium, lisinopril, pentopril, quinapril hydrochlorideramapril, reprotide, zofenopril calcium, diflusinal, diltiazem, felodipine, nicardipine, nifedipine, niludipine, nimodipine, nisoldipine, nitrendipine, verapimil and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg,), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto.

EXAMPLE 1

Preparation of
3-n-Butyl-5-(carbomethoxymethylthio)-4-[4-(2-carboxybenzamido)benzyl]-4H-1,2,4-triazole Step A: Methyl N-(4-Nitrobenzyl)dithiocarbamate To a stirred solution of 150 g (795 mmole) of 4-nitrobenzylamine hydrochloride and 243 ml (176 g, 1.75 mole) of triethylamine in 780 ml of methanol was added gradually (under $N_2$) a solution of 54 ml (68.9 g, 906 mmole) of carbon disulfide in 300 ml of methanol. The internal temperature was maintained below 30° C. during the addition, which took 75 minutes. After an additional hour at room temperature, the reaction mixture was cooled to −10° C. in an ice-MeOH bath as a solution of 50 ml (113 g, 795 mmole) of methyl iodide in 125 ml of methanol was gradually added over about 20 minutes. The cooling bath was removed, and the mixture was allowed to stir at room temperature for 2 hours. It was then concentrated in vacuo to a volume of approximately 500 ml and partioned between 2 L of ether and 2 L of 0.2 N HCl. The ethereal phase was washed with 2 L of saturated aqueous NAGl, dried over. MgSO$_4$, filtered and concentrated to give a yellow solid. Trituration with petroleum ether and drying afforded 187 g (97%) of methyl N-(4-nitrobenzyl)dithiocarbamate, mp 106°-107° C., satisfactory purity by TLC in 2:1 hexane EtOAc; mass spectrum (FAB) m/e 243 (M+1)+.

Analysis (C$_9$H$_{10}$N$_2$O$_2$S$_2$) Calcd: C, 44.61; H, 4.16; N, 11.56. Found: C, 44.98; H, 4.21; N, 11.57.

300 MHz NMR (CDCl$_3$) δ2.66 (s, 3H), 5.06 (d, J=6 Hz, 2H), 7.23 (br m, 1 H), 7.46 (d, J=8 Hz, 2H) 8.19 (d, J=8 Hz, 2H).

Step B: 4-(4-Nitrobenzyl)-3-thiosemicarbazide

A solution of 187 g (772 mmole) of methyl N-(4-nitrobenzyl)dithiocarbamate and 450 ml of hydrazine hydrate in 1400 ml of absolute ethanol was stirred mechanically and heated to reflux. Precipitation began by the time the internal temperature reached about 40° C. After 2 hours at reflux, the mixture was cooled and allowed to stand at room temperature. The solid was collected on a filter, washed with ethanol, and dried to give 105 g (60%) of light yellow crystals, mp 196°-198° C. satisfactory purity by TLC in 95:5:0.5 CH$_2$Cl$_2$—MeOH-concd NH$_4$OH; mass spectrum (FAB) m/e 227 (M+1)+.

Analysis (C$_8$H$_{10}$N$_4$O$_2$S). Calcd: C, 42.48; H, 4.46; N, 24.77. Found: C, 42.62; H, 4.68; N, 24.40.

300 MHz NMR (DMSO)-d$_6$) δ4.56 (br s, 2 H), 4.83 (d, J=6 Hz, 2 H), 7.54 (d, J=9 Hz, 2 H), 8.18 (d, J=9 Hz, 2 H), 8.56 (v br s, 1 H) 8.88 (br s, 1 H).

Step C:
5-n-Butyl-2,4-dihydro-4-(4-nitrobenzyl)-3H-1,2,4-triazole-3-thione

A mixture of 56.6 g (250 mmole) of 4-(4-nitrobenzyl)-3-thiosemicarbazide, 63.1 ml (59.4 g, 370 mmole), and 500 ml of 2-methoxyethanol was stirred at reflux under N$_2$ for approximately 24 hours. The cooled red-orange solution was concentrated. Trituration of the residue with ether gave a solid, which was collected on a filter and washed with ether. After drying, 45.2 g (62%) of white crystals of the filtered compound were obtained, mp 159°-160°, homogeneous by TLC in 19:1 CH$_2$Cl$_2$—MeOH; mass spectrum (FAB) m/e 293 (M+1)+.

Analysis (C$_{13}$H$_{16}$N$_4$O$_2$S) Calcd: C, 53.41; H, 5.52; N, 19.17. Found: C, 53.51; H, 5.56; N, 19.16.

300 MHz NMR (DMSO-d$_6$) δ0.76 (t, J=7 Hz, 3H), 1.22 (m, 2 H), 1.44 (m, 2H), 2.49 (t, J=8 Hz, 2 H), 5.38 (s, 2H ), 7.48 (d, J=8 Hz, 2H ), 8.24 (d, J=8 Hz, 2H).

Step D:
3-n-Butyl-5-(carbomethoxymethylthio)-4-(4-nitrobenzyl)-4H-1,2,4-triazole A stirred solution of 2.00 g (6.84 mmole) of 5-n-butyl-2,4-dihydro-4-(4-nitrobenzyl)-3H-1,2,4-triazole-3-thione in 10 ml of 2-methoxyethanol was treated with 2.38 ml (1.77 g, 13.7 mmole) of N,N-disopropylethylamine followed by 1.20 ml (1.48 g, 13.7 mmole) of methyl chloroacetate. The solution was stirred at room temperature under N$_2$ for 2 hours and then concentrated in vacuo at 45° C. The residual oil was partioned between 70 ml of ethyl acetate and 70 ml of H$_2$O. The organic phase was washed with 70 ml of H$_2$O and then with 50 ml of saturated NaCl solution. The ethyl acetate solution was dried (MgSO$_4$), filtered, concentrated and dried in vacuo to yield 2.50 g (100%) of the titled compound as an oil, homogenous by TLC in 19:1 CH$_2$Cl$_2$—MeOH; mass spectrum (FAB) m/e 365 (M+1)+.

Analysis (C$_{16}$H$_{20}$ON$_4$O$_4$S) Calcd: C, 52.73; H, 5.53; N, 15.38. Found: C, 52.56; H, 5.44; N, 15.12.

300 MHz NMR (CDCl$_3$) δ 0.86 (t; J=7 Hz, 3H), 1.36 (m, 2 H), 1.69 (m, 2H), 2.61 (t,J=7 Hz, 2 H), 3.73 (s, 3H), 4.03 (s, 2H), 5.25 (s, 2H), 7.21 (d, J=8 Hz, 2H ), 8.24 (d, J=8 Hz, 2H).

Step E:
4-(4-Aminobenzyl)-3-n-butyl-5-(carbomethoxymethylthio)-4H-1,2,4-triazole To a solution of 2.46 g (6.76 mmole) of 3 -n- butyl-5-(carbomethoxymethylthio)-4-(4-nitrobenzyl)-4H-1,2,4-triazole in 32 ml of tetrahydrofuran stirred in an ice bath was added gradually over 15 minutes a solution of 15.2 g (67.6 mmole) of stannous chloride dihydrate in 19 ml of concentrated HCl. The ice bath was removed, and the mixture was stirred at room temperature for 1.5 hours. It was then poured into a vigrously stirred mixture of 68 ml of 50% NaOH and 270 g. of ice. This was rapidly extracted with 3×300 ml of ether. The combined ether extracts were washed with 150 ml of H$_2$O, then dried (MgSO$_4$), filtered, and concentrated to give 566 mg (25%) of a white waxy solid, homogeneous by TLC in 97:3 CHCl$_3$-iPrOH; mass spectrum (FAB) m/e 335 (M+1)+. This material was used directly in the next reaction.

300 MHz NMR (DMSO-d$_6$) δ0.82 (t, J=7 Hz, 3H), 1.28 (m, 2 H), 1.52 (m, 2 H), 2.62 (t,J=7 5 Hz, 2 H), 3.53 (s, 3H), 4.02 (s, 2H), 4.94 (s, 2H), 5.33 (v br s, 2H), 6.52 (d, J=8 Hz, 2 H), 6.82 (d, J=8 Hz, 2H).

Step F:
3-n-Butyl-5-(carbomethoxymethylthio)-4-[4-(2-carboxybenzamido)benzyl]-4H-1,2,4-triazole A solution of 566 mg (1.69 mmole) of 4-(4-aminobenzyl)-3-n-butyl-5-(carbomethoxymethylthio)-4H-1,2,4-triazole in 15 ml of dry tetrahydrofuran (THF) was treated with 250 mg (1.69 mmole) of phthalic anhydride dissolved in 2 ml of dry THF. The resulting solution was stirred overnight at room temperature in a stoppered flask. The solid which had precipitated was collected on a filter and washed with ether to yield (after vacuum-drying at 30° C.) 629 mg (77%) of a white solid, mp 161°-162° C., homogeneous by TLC in 90:10:1CH$_2$Cl$_2$—MeOH-AcOH; mass spectrum (FAB) m/e 483 (M+1)+.

Analysis (C$_{24}$H$_{26}$N$_4$O$_5$S) Calcd: C, 59.73; H, 5.43; N, 11.61. Found: C, 59.66; H, 5.48; N, 11.54.

300 MHz NMR (DMSO-d$_6$) δ0.85 (t, J=7 Hz, 3H), 1.31 (m, 2 H), 1.56 (m, 2H), 2.65 (t, J=7.5 Hz, 2 H), 3.63 (s, 3H), 4.04 (s, 2H), 5.14 (s, 2H), 7.08 (d, J=8 Hz, 2H), 7.5–7.7 (m, 5H), 7.88 (d, 8 Hz, 1H), 10.40 (s, 1H).

EXAMPLE 2

Preparation of
3-n-Butyl-4-[4-(2-carboxybenzamido)benzyl]-5-(N-methylcarbamoylmethylthio)-4H-1,2,4-triazole

Step A:
3-n-Butyl-5-(N-methylcarbamoylmethylthio)-4-(4-nitrobenzyl)-4H-1,2,4-triazole To a stirred solution of 502 mg (1.37 mmole) of 3-n-butyl-5-(carbomethoxymethylthio)-4- 4-nitrobenzyl)-4H-1,2,4-triazole in 2.2 ml of methanol was added 2.2 ml of 40% methylamine (aqueous). Within 15 minutes a heavy precipitate had formed. After dilution with $H_2O$, the solid was collected on a filter and washed with $H_2O$ followed (after air-drying) by ether. The titled compound (413 mg, 83%) was obtained as a white solid, mp 132°–133° C., virtually homogeneous by TLC in 19:1 $CH_2Cl_2$—MeOH; mass spectrum (FAB) m/e 364 $(M+1)^+$. Analysis ($C_{16}H_{21}N_5O_3S$) Calcd: C, 52.87; H, 5.82; N, 19.27. Found: C, 52.87; H, 5.84; N, 19.17.

300 MHz NMR (DMSO-$d_6$) $\delta$0.81 (t, J=7 Hz, 3H), 1.28 (m, 2H), 1.53 (m; 2H), 2.56 (d,. J=4 Hz, 3H) 2.62 (t, J=8 Hz, 2H), 3.82 (s, 2H), 5.38 (s, 2H), 7.32 (d, J=8 Hz, 2H), 8.13 (br m, 1H), 8.24 (d, J=8 Hz, 2H).

Step B:
4-(4-Aminobenzyl)-3-n-butyl-5-(N-methylcarbamoylmethylthio)-4H-1,2,4-triazole Reduction of 3-n-butyl-5-(N-methylcarbamoylmethylthio)-4-(4-nitrobenzyl)-4H-1,2,4-triazole with stannous chloride according to the procedure of Example 1, Part E afforded a 40% yield of white solid, mp 124°–125° C., homogeneous by TLC in 9:1 $CHCl_3$-MeOH; mass spectrum (FAB) m/e 334 $(M+1)^+$.

Analysis ($C_{16}H_{23}N_5OS.0.2 H_2O$) Calcd: C, 57.01; H, 7.00; N, 20.78. Found: C, 57.27, H, 6.99; N, 20.42.

300 MHz NMR (DMSO-$d_6$) $\delta$0.83 (t, J=7Hz, 3H), 1.29 (m, 2H), 1.52 (m, 2H), 2.59 (d, J=4Hz, 3H), 2.61 (t, 8Hz, 2H), 3.80 (s, 2H), 4.95 (s, 2H), 5.14 (br s, 2H ), 6.51 ( d, J=8Hz, 2H ), 6.80 ( d, J=8 Hz, 2H ), 8.13 (br d, J=4Hz, 1H).

Step C:
3-n-Butyl-4-[4-(2-carboxybenzamido)benzyl]-5-(N-methylcarbamoylmethylthio)-4H-1,2,4-triazole By the procedure of Example 1, Part F, 4-(4-aminobenzyl)-3-n-butyl-5-(N-methylcarbamoylmethylthio)-4H-1,2,4-triazole was reacted with phthalic anhydride. Because the product did not precipitate, the solution was concentrated in vacuo. Trituration of the residue with ether afforded a 73% yield of a white solid, mp 137°–139° C. dec., homogeneous by TLC in 90:10:1$CH_2Cl_2$—MeOH-AcOH; mass spectrum (FAB) m/e 482 $(M+1)^+$.

Analysis ($C_{24}H_{27}N_5O_4S.0.25 H_2O$) Calcd: C, 59.30; H, 5.70; N, 14.41. Found: C, 59.35; H, 5.81; N, 14.38.

300 MHz NMR (DMSO-$d_6$) $\delta$0.84 (t, J=7Hz, 3H), 1.31 (m, 2H), 1.55 (m, 2H), 2.58 (d, J=4Hz, 3H), 2.64 (t, J=7.5Hz, 2H), 3.82 (s, 2H), 5.14 (s, 2H), 7.07 (d, J=8Hz, 2H), 7.5-7.7 (m, 5H), 7.87 (d, J=7.5 Hz, 1H), 8.13 (br m, 1H), 10.40 (s, 1H), 13.02 (br s, 1H).

EXAMPLE 3

Preparation of
3-n-Butyl-4-[4-(2-carboxybenzamido)benzyl]-5-(2-hydroxyethythio)-4H-1,2,4-triazole

Step A:
3-n-Butyl-5-(2-hydroxyethylthio)-4-(4-nitrobenzyl)-4H-1,2,4-triazole A solution of 2.00 g (6.79 mmole) of 5-n-butyl-2,4-dihydro-4-(4-nitrobenzyl)-3H-1,2,4-triazole-3-thione in 20 ml of 2-methoxyethanol was treated with 2.37 ml (1.76 g, 13.6 mmole) of N,N-diisopropylethylamine followed by 0.96 ml (1.70 g, 13.6 mmole) of 2-bromoethanol. The solution was stirred under $N_2$ at room temperature for 2 days and then concentrated in vacuo. The residual oil was partitioned between 50 ml of ethyl acetate and 100 ml of 0.1 N HCl. The organic layer was washed with an additional 100 ml of 0.1N HCl then dried over $MgSO_4$, filtered, and concentrated at 35° C. The residue was purified by column chromatography on silica gel (gradient elution with 2.2–9% methanol in $CH_2Cl_2$), affording 1.46 g (61%) of an oil, homogeneous by TLC in 19:1 $CH_2Cl_2$—MeOH; mass spectrum (FAB) m/e 337 $(M+1)^+$.

Analysis (C15H20N4O3S.0.75 $H_2O$) Calcd: C, 51.48; H, 6.19; N, 16.01. Found: C, 51.64; H, 6.00; N, 15.86.

300 MHz NMR (CDCl$_3$) $\delta$0.82 (t, J=7 Hz, 3H), 1.31 (m, 2H), 1.64 (m, 2H), 2.55 (t, J=8 Hz, 2H) 3.27 (t, J=5.5 Hz, 2H), 3.96 (t, J=5.5 Hz, 2H), 5.11 (s, 2H), 7.15 (d, J=8 Hz, 2H), 8.17 (d, J=8 Hz, 2H).

Step B:
4-(4-Aminobenzyl)-3-n-butyl-5-(2-hydroxyethythio)-4H-1,2,4-triazole

Treatment of 3-n-butyl-5-(2-hydroxyethylthio)-4H-1,2,4-triazole with stannous chloride according to the procedure of Example 1, Part E gave a 30% yield of the desired amine as a solid, mp 131°–133° C., homogeneous by TLC in 9:1$CHCl_3$—MeOH; mass spectrum (FAB) m/e 306 $(M+1)^+$.

300 MHz NMR (DMSO-$d_6$) $\delta$0.84 (t, J=7Hz, 3H), 1.30 (m, 2H), 1.53 (m, 2H), 2.62 (t, J=7Hz, 2H), 3.17 (t, J=7Hz, 2H), 3.64 (dt, J=6,7Hz, 2H), 4.95 (s, 2H), 5.05 (t, J=6Hz, 1H), 5.15 (br s, 2H), 6.52 (d, J=8 Hz, 2H), 6.80 (d, J=8Hz, 2H).

Step C:
3-n-Butyl-4-[4-(2-carboxybenzamido)benzyl]-5-(2-hydroxyethythio)-4H-1,2,4-triazole By the procedure of Example 1, Part F, 4-(4-aminobenzyl)-3-n-butyl-5-(2-hydroxyethylthio)-4H-1,2,4-triazole was reacted with phthalic anhydride. Concentration of the reaction mixture and trituration of the residue with acetone gave a 69% yield of white solid, mp 157°–159° C., homogeneous by TLC in 90:10:1 $CH_2Cl_2$—MeOH-AcOH; mass spectrum (FAB) m/e 455 $(M+1)^+$. Analysis ($C_{23}H_{26}N_4O_4S.0.3 H_2O$) Calcd: C, 60.06; H, 5.83; N, 12.18. Found: C, 60.23; H, 5.88; N, 12.14.

300 MHz NMR (DMSO-$d_6$) $\delta$0.84 (t, J=7Hz, 3H), 1.31 (m, 2H), 1.56 (m, 2H), 2.64 (t, J=7Hz, 2H), 3.16 (t, J=7Hz, 2H), 3.62 (m, 2H), 5.04 (br m, 1H), 5.12 (s, 2H), 7.05 (d, J=8 Hz, 2H), 7.5-7.7 (m, 5H), 7.87 (d, J=7Hz, 1H), 10.39 (s, 1H).

EXAMPLE 4

Preparation of
3-Benzylthio-5-n-butyl-4-[4-(2-carboxybenzamido)benzyl]-4H-1,2,4-triazole

Step A:
3-Benzylthio-5-n-butyl-4-(4-nitrobenzyl)-4H-1,2,4-triazole

A solution of 929 mg (3.18 mmole) of 5-n-butyl-2,4-dihydro-4-(4-nitrobenzyl)-3H-1,2,4-triazole-3-thione in 8.7 ml of 2-methoxyethanol was treated with 1.09 ml (809 mg, 6.26 mmole) of N,N-disopropylethylamine followed by 720 µl (793 mg, 6.26 mmole) of benzyl chloride. The solution was stirred at room temperature under $N_2$ for 2 days and then concentrated in vacuo at 35° C. The residue was taken up in ethyl acetate and washed successively with 50 ml of $H_2O$, 50 ml of 0.2 N HCl and 50 ml of $H_2O$. After drying over $MgSO_4$, the ethyl acetate solution was filtered and concentrated in vacuo. The residue was chromatographed on a silica gel column (gradient elution with 1–3% methanol in $CH_2Cl_2$) to yield 757 mg (78%) of an oil, homogeneous by TLC in 19:1$CH_2Cl_2$—MeOH; mass spectrum (FAB) m/e 383 (M+1)+.

Analysis ($C_{20}H_{22}N_4O_2S.0.2H2O$) Calcd: C,62.22; H, 5.85; N, 14.51. Found: C, 62.38; H, 5.77; N, 14.52.

300 MHz NMR (CDCl$_3$) δ0.87 (t, J=7.5 Hz, 3H), 1.33 (m, 2H), 1.64 (m, 2H), 2.52 ( t, J=8 Hz, 2H), 4.36 ( s, 2H), 4.86 (s, 2H), 6.97 (d, J=8 Hz, 2H), 7.26 (m, H), 8.12 (d, J=8 Hz, 2H).

Step B:
4-(4-Aminobenzyl)-3-benzylthio-5-n-butyl-4H-1,2,4-triazole

A solution of 916 mg (2.4 mmole) of 3-benzylthio-5-n-butyl-4-(4-nitrobenzyl)-4H-1,2,4triazole in 13 ml of tetrahydrofuran (THF) was stirred in an ice bath as a solution of 5.42 g (24 mmole) of stannous chloride dihydrate in 7 ml of concentrated HCl was added dropwise over the course of 12 minutes. The ice bath was removed, and the mixture was stirred at room temperature for 5 hours. Next, it was poured into a vigorously stirred mixture of 37 ml of 50% NaOH and 100 g of ice, and the product was extracted with 3×100 ml of ether. The combined ether fractions were washed with $H_2O$, then dried over $MgSO_4$, filtered, and concentrated in vacuo to yield 824 mg (94%) of an oil which was homogeneous by TLC in 9:1 CHCl$_3$-MeOH; mass spectrum (FAB) m/e 353 (M+1)+.

Analysis [$C_{20}H_{24}N_4S.0.4$ $H_2O.0.1$ $C_4H_8O$ (THF)]Calcd: C, 66.78; H, 7.03; N, 15.27. Found: C, 67.07; H, 7.29; N, 14.94.

300 MMz NMR (CDCl$_3$) δ0.88 (t, J=7 Hz, 3H), 1.33 (m, 2H), 1.62 (m, 2H), 2.57 (t, J=7.5 Hz, 2H), 4.33 (s, 2H ), 4.67 (s, 2H ), 6.56 (d, J=8 Hz, 2H ), 6.72 (d, J=8 Hz, 2H), 7.27 (s, 5H); small multiplets at 1.84 and 3.75 confirmed presence of THF.

Step C:
3-Benzylthio-5-n-butyl-4-[4-(2-carboxybenzamido)benzyl]-4H-1,2,4-triazole To solution of 788 mg (2.24 mmole) of 4-(4-aminobenzyl)-3-benzylthio-5-n-butyl-4H-1,2,4-triazole in 1.9 ml of dry tetrahydrofuran (THF) was added a solution of 332 mg (2.24 mmole) of phthalic anhydride in dry THF. The solution was stirred at room temperature in a stoppered flask for 2 hours and then concentrated in vacuo at room temperature. Trituration of the residual stiff foam with ether gave 988 mg (85%) of an off-white solid: mp 158°–160°, homogeneous by TLC in 90:10:1$CH_2Cl_2$—MeOH-AcOH; mass spectrum (FAB) m/e 501 (M+1)+.

Analysis [$C_{28}H_{28}N_4O_3S.0.5.H_2O0.1$ $C_4H_{10}O$ (ether)-]Calcd: C, 65.97; H, 5.85; N, 10.84. Found: C, 66.01; H, 5.87; N, 10.55.

300 MHz NMR (DMSO-d$_6$) δ0.84 (t, J=7 Hz, 3H), 1.29 (m, 2H), 1.54 (m, 2H) 2.60 (t, J=8 Hz, 2H) 4.32 (s, 2 H), 4.96 (s, 2 H), 6.92 (d, J=8 Hz, 2 H), 7.30 (m, 5H), 7.5–7.7 (m, 5H), 7.88 (d, J=8 Hz, 1H), 10.36 (s,1H), 13.01 (br s, 1H); presence of small amount of ether also confirmed.

EXAMPLE 5

Preparation of
3-n-Butyl-4-[4-(2-carboxybenzamido)benzyl]-5-phenylthio-4H-1,2,4-triazole

Step A:
3-n-Butyl-5-chloro-4-(4-nitrobenzyl)-4H-1,2,4-triazole

Chlorine gas was bubbled through a stirred solution of 5.00 g (17.1 mmole) of 5-n-butyl-2,4-dihydro-4-(4-nitrobenzyl)-3H-1,2,4-triazole-3-thione in 260 ml of dry $CH_2Cl_2$ for 1.5 hours. A precipitate formed after 10 minutes. (This material, which is not the desired final product, is not isolated). The reaction mixture was poured into 400 ml of ethyl acetate and washed with 3×500 ml of saturated NaHCO$_3$ solution, 400 ml of $H_2O$, and finally 400 ml of saturated NaCl solution. The ethyl acetate phase was dried over MgSO$_4$, filtered, and concentrated. The residue was pre-absorbed onto silica gel by evaporation from methanol. This was added as a slurry to the top of a silica gel column, which was eluted with a gradient of 0–1% methanol in $CH_2Cl_2$. Concentration of pooled product fractions yielded 1.90 g (37%) of a yellow oil, which showed satisfactory purity by TLC in 19:1$CH_2Cl_2$—MeOH and gave a positive Bellstein test for chlorine; mass spectrum (EI) m/e 294 (M+).

Analysis ($C_{13}H_{15}ClN_4O_2.0.33$ $H_2O$) Calcd: C, 51.92; H, 5.23; N, 18.64; Cl, 11.79. Found: C, 51.69; H, 5.18; N, 18.24; Cl, 11.84.

300 MHz NMR (CDCl$_3$) δ0.89 (t, J=7 Hz, 3H), 1.38 (m, 2H), 1.71 (m, 2H) 2.64 (t, J=7.5 Hz, 2H) 5.21 (s, 2 H), 7.22 (d, J=8 Hz, 2 H), 8.26 (d, J=8 Hz, 2H)

Step B:
3-n-Butyl-4-(4-nitrobenzyl)-5-phenylthio-4H-1,2,4-triazole

A solution of 100 mg (0.34 mmole) of 3-n-butyl-5-chloro-4-(4-nitrobenzyl)-4H-1,2,4-triazole, 140 µl (150 mg, 1.36 mole) of thiophenol, and 237 µl (176 mg, 1.36 mmole) of N,N-diisopropylethylamine in 1 ml of dry DMF was stirred at reflux under $N_2$ for 2 hours. The cooled dark solution was concentrated in vacuo, and the residue was partitioned between 50 ml of ether and 50 ml of 0.2N HCl. The ethereal phase was washed with saturated Na$_2$CO$_3$ solution, then dried (MgSO$_4$), filtered and concentrated. Column Chromatography of the residue on silica gel (gradient elution with 0–2% isopropanol in CHCl$_3$) gave 28 mg (22%) of an oil, homogeneous by TLC in 97:3 CHCl$_3$—PrOH; mass spectrum (FAB) m/e 369 (M+1)+.

300 MHz NMR (CDCl$_3$) δ0.86 (t, J=7Hz, 3H), 1.34 (m, 2H), 1.70 (m, 2H), 2.58 (t, J=7.5 Hz, 2H), 5.22 (s,

2H), 6.91 (d, J=8Hz, 2H), 7.1-7.3 (m, 5H), 8.04 (d, J=8Hz, 2H).

Step C:
4-(4-Aminobenzyl)-3-n-butyl-5-phenylthio-4H-1,2,4-triazole

The stanous chloride reduction of 3-n-butyl-4-(4-nitrobenzyl)-5-phenylthio-4$\underline{H}$-1,2,4-triazole was accomplished using the procedure of Example 1, Part E, except that ethyl acetate rather than ether was used for the product extraction. A quantitative yield of the amine was obtained as an oil, homogeneous by TLC in 9:1 CHCl$_3$-MeOH; mass spectrum (FAB) m/e 339 (M+1)$^+$.

300 MHz NMR (CDCl$_3$) $\delta$0.87 (t, J=7.5 Hz, 3H), 1.34 (m, 2H), 1.56 (m, 2H), 2.61 (t, J=8Hz, 2H), 5.00 (s, 2H), 6.53 (d, J=8Hz, 2H), 6.69 (d, J=8 Hz, 2H), 7.2-7.35 (m, 5H).

Step D:
3-n-Butyl-4-[4-(2-carboxybenzamido)benzyl]-5-phenylthio-4H-1,2,4-triazole Treatment of 4-(4-aminobenzyl)-3-n-butyl-5-phenylthio-4H-1,2,4-triazole with phthalic anhydride according to the procedure of Example 4, Part C, gave a 42% yield of pale yellow solid, mp 144°-146° C., good purity by TLC in 90:10:1CH$_2$Cl$_2$—MeOH-AcOH; mass spectrum (FAB) m/e 487 (M+1)$^+$.

Analysis (C$_{27}$H$_{26}$N$_4$O$_3$S.H$_2$O) Calcd: C, 64.26; H, 5.59; N, 11.11. Found: C, 64.46; 11, 5.59; N, 10.86.

300 MHz NMR (DMSO-d$_6$) $\delta$0.83 (t, J=7.5Hz, 311), 1.29 (m, 2H), 1.56 (m, 2H), 2.65 (t, J=7.5 Hz, 211), 5.19 (s, 2H), 6.92 (d, J=8Hz, 2H), 7.2-7.4 (m, 5H), 7.5-7.7 (m, 5H), 7.87 (d, J=8Hz, 1H), 10.37 (s, 1H), 13.04 (v br s, 1H).

EXAMPLE 6

Preparation of 4-[4-(2-Carboxybenzamido)benzyl]-3-ethylthio-3-ethylthio-5-trifluoromethyl-4H-1,2,4-triazole

Step A:
2,4-Dihydro-4-(4-nitrobenzyl)-5-trifluoromethyl-3H-1,2,4-triazole-3-thione A suspension of 1.00 g (4.42 mmole) of 4-(4-nitrobenzyl)-3-thiosemicarbazide in 1.1 ml of anhydrous trifluoroacetic acid was heated under N$_2$ in an oil bath at 75° C. for one hour and then at 125° C. for 24 hours. The solid obtained upon cooling was treated portionwise with saturated aqueous NaHCO$_3$ solution (about 10 ml total), and the mixture was stirred thoroughly until CO$_2$ evolution had ceased. The solid was collected on a filter, washed thoroughly with H$_2$O, and then dried in vacuo over P$_2$O$_5$ to give 1.07 g (80%) of a pale yellow solid, mp 155°-157° C., homogeneous by TLC in 19:1 CH$_2$Cl$_2$—MeOH; mass spectrum m/e 305 (M+1)$^+$.

Analysis (C$_{10}$H$_7$F$_3$N$_4$O$_2$S) Calcd: C, 39.47; H, 2.32; N, 18.42. Found: C, 39.58; H, 2.38; N, 18.16.

300 MHz NMR (DMSO-d$_6$) $\delta$5.49 (s, 2H), 7.50 ( d, J=8 Hz, 2H), 8.22 (d, J=8 Hz, 2H)

Step B:
3-Ethylthio-4-(4-nitrobenzyl)-5-trifluoromethyl-4H-1,2,4-triazole

A solution of 1.07 g <3.52 retool) of 2,4-dihydro-4-(4-nitrobenzyl)-5-trifluoromethyl-3H-1,2,4-triazole-3H-thione in 9 ml of methanol was treated with 613 $\mu$l (454 rag, 3.52 mmole) of N,N-diisopropylethylamine followed by 296 $\mu$l (577 mg, 3.70 mmole) of ethyl iodide. The solution was stirred at 60° C. under N$_2$ for two hours, then cooled and concentrated. The residue was partitioned between 50 ml of ethyl acetate and 50 ml of 0.2 N HCl. The ethyl acetate fraction was washed with an additional 50 ml of 0.2 N HCl and then with saturated NaCl solution. The organic phase was dried (MgSO$_4$), filtered, and concentrated. The residual oil was chromatographed on a column of silica gel (gradient elution with 0–0.8% methanol in CH$_2$Cl$_2$) to provide 586 mg (50%) of an oil which solidified on standing: mp 70°-71.5° C., homogeneous by TLC in 19:1 CH$_2$Cl$_2$—MeOH; mass spectrum (FAB) m/e 333 (M+1)$^+$.

Analysis (Cl$_2$H$_{11}$F$_3$N$_4$O$_2$S) Calcd: C, 43.37; H, 3.34; N, 16.86. Found: C, 43.32; H, 3.17; N, 16.70.

300 MHz NMR (CDCl$_3$) $\delta$1.55 (t, J=7.5 Hz, 3H), 3.37 (q, J=7.5 Hz, 2H), 5.30 (s, 2H), 7.28 (d, J=8 Hz, 2H), 8.25 (d, J=8Hz, 2H).

Step C: 4-(4-Aminobenzyl)-3-ethylthio-5-trifluoromethyl-4H-1,2,4-triazole

Stannous chloride reduction of 3-ethylthio-4-(4-nitrobenzyl)-5-trifluoromethyl-4H-1,2,4-triazole according to the procedure of Example 1, Part E, yielded 70% of the amine as a yellow oil (which transformed to a waxy solid on standing), homogeneous by TLC in 9:1CHCl$_3$-MeOH; mass spectrum (FAB) m/e 303 (M+1)$^+$.

Analysis [C$_{12}$H$_{13}$F$_3$N$_4$S.0.8H$_2$O.0.03C$_4$H$_8$O$_2$(ethyl acetate)]Calcd: C, 45.88; H, 4.68; N, 17.55. Found: C, 45.70; H, 4.40; N, 17.16.

300 MHz NMR (DMSO-d$_6$) $\delta$1.33 (t, J=7.5 Hz, 3H), 3.23 (q, J=7.5 Hz, 2H), 5.09 (s, 2H), 5.6 (v br s, 2H), 6.54 (d, J=8Hz, 2H), 6.82 (d, J=8Hz, 2H); presence of a small amount of ethyl acetate was also confirmed.

Step D:
4-[4-(2-Carboxybenzamido)benzyl]-3-ethylthio-5-trifluoromethyl-4H-1,2,4-triazole Reaction of 4-(4-aminobenzyl)-3-ethylthio-5-trifluoromethyl-4$\underline{H}$-1,2,4-triazole with phthalic anhydride according to the procedure of Example 1, Part F, provided a 59% yield of white solid, mp 154°-156° C., homogeneous by TLC in 90:10:1 CH$_2$Cl$_2$—MeOH-AcOH; mass spectrum (FAB) m/e 451 (M+1)$^+$.

Analysis [C$_{20}$H$_{17}$F$_3$N$_4$O$_3$S.0.4 C$_4$H$_{10}$O (ether)]Calcd: C, 54.04; H, 4.41; N, 11.67. Found: C, 53.98; H, 4.28; N, 11.37.

300 MHz NMR (DMSO-d$_6$) $\delta$1.35 (t, J=7Hz, 3H), 3.25 (q, J=7Hz, 2H), 5.27 (s, 2H), 7.07 (d, J=7.5 Hz, 2H), 7.5-7.7 (m, 5H), 7.87 (d, J=7.5 Hz, 1H), 10.42 (s, 1H); presence of ether was also confirmed.

EXAMPLE 7

Preparation of 4-[4-(2-Carboxybenzamido)benzyl]-3-ethylthio-5-methoxymethyl-4H-1,2,4-triazole

Step A:
2.4-Dihydro-5-methoxymethyl-4-(4-nitro-benzyl)-3H-1,2,4-triazole-3-thione A mixture of 2.51 g (11.1 mmole) of 4-(4-nitrobenzyl)-3-thiosemicarbazide, 2.00 g (13.3 mmole) of trimethyl 2-methoxyorthoacetate*, and 30 ml of 2-methoxyethanol was stirred under N$_2$ in an oil bath at 100° C. A clear solution developed within a few minutes. After three days, the solution was cooled and concentrated. The residual solid was leached with hot CH$_2$Cl$_2$ (approximately 50 ml) and then purified by column chromatography on silica gel. (Note: The material was preabsorbed on silica gel from methanol and added as a slurry to the top of the column.) Following gradient elution with 0–0.75% methanol in $CH_2Cl_2$, concentration of the product fractions yielded 1.07 g (34%) of an off-white solid, mp 170°–172° C., homogeneous by TLC in 19:1 $CH_2Cl_2$—MeOH; mass spectrum (FAB) m/e 281 (M+1)+.

(*J. H. van Boom, G. R. Owen, J. Preston, T. Ravindranathan, and C. B. Reese, *J. Chem. Soc. (C)*, 3230 (1971)

Analysis ($C_{11}H_{12}N_4O_3S$) Calcd: C, 47.13; H, 4.32; N, 19.99. Found: C, 46.94; H, 4.29; N, 19.81.

300 MHz NMR (DMSO-d6) δ3.10 (s, 3H), 4.40 (s, 2H), 5.36 (s, 2H), 7.48 (d, J=8 Hz, 2H), 8.21 (d, J=8 Hz, 2H)

Step B:
3-Ethylthio-5-methoxymethyl-4-(4-nitrobenzyl)-4H-4H-1,2,4-triazole

Alkylation of 2,4-dihydro-5-methoxymethyl-4-(4-nitrobenzyl)-3J-1,2,4-triazole-3-thione with ethyl iodide according to the procedure of Example 6, Part B, provided a 43% yield of the product as an oil, homogeneous by TLC in 19:1$CH_2Cl_2$—MeOH; mass spectrum (FAB) m/e 309 (M+1)+.

Analysis ($C_{13}H_{16}N_4O_3S$) Calcd: C, 50.63; H, 5.23; N, 18.17. Found: C, 50.23; H, 5.18; N, 17.97.

300 MHz NMR (CDCl3) δ1.42 (t, J=7.5 Hz, 3H), 3.28 (q, J=7.5 Hz, 2H), 3.32 (s, 3H), 4.56 (s, 2H), 5.27 (s, 2H), 7.30 (d, J=8Hz, 2H), 8.23 (d, J=8Hz, 2H).

Step C:
4-(4-Aminobenzyl)-3-ethylthio-5-methoxymethyl-4H-1,2,4-triazole

This material was obtained in 80% yield by treatment of 3-ethylthio-5-methoxymethyl-4-(4-nitrobenzyl)-4H-1,2,4-triazole with stannous chloride according to the procedure of Example 1, Part E. The product was obtained as a clear oil, homogeneous by TLC in 9:1 CHCl3-MeOH; mass spectrum (FAB) m/e 279 (M+1)+.

Analysis [$C_{13}H_{18}N_4OS$.0.1 $H_2O$.0.2 $C_4H_{10}O$ (ether)]Calcd: C, 56.18; H, 6.90; N, 19.00. Found: C, 56.05; H, 6.93; N, 19.20.

300 MHz NMR (DMSO-d6) δ1.26 (t, J=7.5 Hz, 3H), 3.08 (q, J=7.5 Hz, 2H), 3.26 (s, 3H), 4.50 (s, 2H), 4.95 (s, 2H), 5.14 (br s, 2H), 6.50 (d, J=8Hz, 2H), 7.86 (d, J=8Hz, 2H).

Step D:
4-[4-(2-Carboxybenzamido)benzyl]-3-ethylthio-5-methoxymethyl-4H-1,2,4-triazole By the procedure of Example 1, Part F, 4-(4-aminobenzyl)-3-ethylthio-5-methoxymethyl-4H-1,2,4-triazole was reacted with phthalic anhydride to give a 90% yield of white solid, mp 192°–193° C., homogeneous by TLC in 90: 10: $CH_2Cl_2$—MeOH-AcOH; mass spectrum (FAB) m/e 428 (M+1)+.

Analysis ($C_{21}H_{23}N_4O_4S$) Calcd: C, 59.00; H, 5.42; 13.11. Found: C, 59.36; H, 5.47; 12.95.

300 MHz NMR (DMSO-d6) δ1.27 (t, J=7.5Hz, 3H), 3.10 (q, J=7.5Hz, 2H), 3.27 (s, 3H), 4.56 (s, 2H), 5.13 (s, 2H), 7.12 (d, J=8Hz, 2H), 7.5–7.7 (m, 5H), 7.87 (d, J=8Hz, 1H), 10.39 (s, 1H), 13.02 (br s, 1H).

EXAMPLE 8

Preparation of 4-[4-(2-Carboxybenzamido)benzyl]-3H-ethylthio-5-phenyl-4H-1,2,4-triazole

Step A:
2,4-Dihydro-4-(4-nitrobenzyl)-5-phenyl-3H-1,2,4-triazole-3-thione

A mixture of 1.10 g (4.86 mmole) of 4-(4-nitrobenzyl)-3-thiosemicarbazide, 1.00 ml (1.07 g, 5.83 mmole) of trimethyl orthobenzoate, and 5.5 ml of 2-methexyethanol was stirred at 100° C. overnight. The mixture, from which a solid had precipitated, was cooled and filtered to give 779 mg of a white powder. The residue from concentration of the mother liquor was flash chromatographed on silica gel (elution with 0.75% methanol in $CH_2Cl_2$) to provide an additional 214 mg of the titled compound, mp 237.5°–238° C., homogeneous by TLC in 97:3 $CH_2Cl_2$—MeOH; mass spectrum (FAB) m/e 313 (M+1)+.

300 MHz NMR (CDCl3) δ3.72 (br s, 1H), 5.28 (s, 2H), 7.1–7.45 (m, 7H), 8.02 (d, J=9 Hz, 2H).

Step B:
3-Ethylthio-4-(4-nitrobenzyl)-5-phenyl-4H-1,2,4-triazole

Reaction of 2,4-dihydro-4-(4-nitrobenzyl)-5-phenyl-3H-1,2,4-triazole-3-thione with ethyl iodide according to the procedure of Example 6, Part B, gave a 91% yield of the desired product as a solid, mp 107.5°–108.5° C., homogeneous by TLC in 97:3 $CH_2Cl_2$—MeOH; mass spectrum (FAB) m/e 341 (M+1)+.

200 MHz NMR (CDCl3) δ 1.40 (t, J=7Hz, 3H), 3.30 (q, J=7Hz, 2H), 5.25 (s, 2H), 7.18 (d, J=8Hz, 2H), 7.35–7.5 (m, 5H), 8.18 ( d, J=8Hz, 2H).

Step C:
4-(4-Aminobenzyl)-3-ethylthio-5-phenyl-4H-1,2,4-triazole

Following the procedure of Example, 1, Part E, 3-ethylthio-4-(4-nitrobenzyl)-5-phenyl-4H-1,2,4triazole was reduced with stannous chloride to give (after multiple extractions with ethyl acetate in addition to ether) an 82% yield of the amine as a solid, mp 126.5°–127° C., homogeneous by TLC in 9:1 $CH_2Cl_2$—MeOH, mass spectrum (FAB) m/e 311 (M+1)+.

200 MHz NMR (CDCl3) δ1.40 (t, J=7.5Hz, 3H), 3.26 (q, J=7.5Hz, 2H), 3.72 (br s, 2H), 5.04 (s, 2H), 6.60 (d, J=8Hz, 2H), 6.78 (d, J=8Hz, 2H), 7.35–7.6 (m, 5H).

Step D:
4-[4-(2-Carboxybenzamido)benzyl]-3-ethylthio-5-phenyl-4H-1,2,4-triazole Treatment of 4-(4-aminobenzyl)-3-ethylthio-5-phenyl-4H-1,2,4-triazole with phthalic anhydride as described in Example 4, Part C, gave a 60% yield of pale yellow solid, mp 177.5°–178° C., homogeneous by TLC in 90:10:1$CH_2Cl_2$—MeOH-AcOH; mass spectrum (FAB) m/e 459 (M+1)+.

Analysis ($C_{25}H_{22}N_4O_3S$,0.2 $H_2O$) Calcd: C, 64.97; H, 4.89; N, 12.12. Found: C, 64.92; H, 4.93; N, 12.04.

300 MHz NMR (DMSO-d6) δ1.33 (t, J=7.5Hz, 3H), 3.17 (q, J=7.5Hz, 2H), 5.21 (s, 2H), 6.92 (d, J=8Hz, 2H), 7.45–7.7 (m, 10H), 7.87 (d, J=8Hz, 1H), 10.39 (s, 1H), 13.02 (br s, 1H).

EXAMPLE 9

Preparation of 3-n-Butyl-4-[4-(2-carboxybenzamido)benzyl]-5-(2-furyl)-4H-1,2,4-triazole

Step A: Ethyl Valerate 2-Furoylhydrazone

A solution of 2.40 g (15.2 mmole) of ethyl valerimidate hydrochloride* in 25 ml of dry ethanol was stirred at −10° C. (ice-salt bath) under protection from moisture as a solution of 1.97 g (15.6 mmole) of 2-furoic hydrazide in 60 ml of dry ethanol was added dropwise over 15 minutes. Upon completion of the addition, the flask was stoppered and kept at 5° C. for three days. The filtered solution was concentrated, and the residue was flash chromatographed on silica gel (elution with 1.5% methanol in $CH_2Cl_2$) to give 2.18 g (58%) of an oil which was sufficiently pure by TLC (97:3 $CH_2Cl_2$—MeOH) for use in the next step. Mass spectrum (FAB) m/e 239 (M+1)+. NMR suggested that the material is a mixture of syn and anti-isomers.

200 MHz NMR ($CDCl_3$) 0.8–0.95 (m, 2H), 1.2–1.4 (m, 5H), 2.3–2.5 (m, 2H), 4.1–4.25 (m, 2H), 6.46 (m, 1H), 7.13 (m, 1H), 7.42 (s, 1H), 8.38, 9.53 (br s, 1H total)

*(prepared by method of A. J. Hill and I. Rabinowitz, *J. Am. Chem. Soc.*, 48, 734 (1926))

Step B: 3-n-Butyl-5-(2-furyl)-4-(4-nitrobenzyl)-4H-1,2,4-triazole

To 678 mg (2.85 mmole) of ethyl valerate 2-furoylhydrazone dissolved in 3 ml of ethanol was added a solution of 514 mg (2.16 mmole) of 4-nitrobenzylamine (generated from the hydrochloride by partitioning between ether and saturated $Na_2CO_3$ solution) in 3 ml of ethanol. The resulting solution was heated at 45°–50° C. for two hours and then at 70° C. overnight. The solution was cooled and concentrated. Column chromatography of the residue on silica gel (gradient elution with 0.5–2.5% methanol in $CH_2Cl_2$) afforded some recovered starting material (ester hydrazone) followed by 432 mg (61%) of the product as a yellow oil which upon standing at 5° C. crystallized to a solid having mp 91°–92.5° C., homogeneous by TLC in 97:3 $CH_2Cl_2$—MeOH; mass spectrum (FAB) m/e 327 (M+1)+.

300 MHz NMR ($CDCl_3$) δ0.87 (t, J=7Hz, 3H ), 1.37 (m, 2H), 1.71 (m, 2H), 2.65 (t, J=7.5Hz, 2H), 5.46 (s, 2H ), 6.49 (dd, J=3.5,1Hz, 1H), 7.01 (d, J=3.5Hz, 1H ), 7.18 (d, J=8Hz, 2H ), 7.42 (d, J=1Hz, 1H), 8.18 (d, J=8Hz, 2H)

Step C: 4-(4-Aminobenzyl)-3-n-butyl-5-(2-furyl)-4H-1,2,4.triazole

A sample of 3-n-butyl-5-(2-furyl)-4-(4-nitrobenzyl)-4H-1,2,4-triazole was reduced with stannous chloride using the conditions of Example 1, Part E. After quenching with cold NaOH solution, the product was extracted 3× with ether and 2× with ethyl acetate. Purification by flash chromatography on silica gel (elution with 97:3 $CH_2Cl_2$—MeOH) afforded 83% of a pale yellow powder, mp 111°–111.5° C., homogeneous by TLC in 19:1 $CH_2Cl_2$—MeOH; mass spectrum (FAB) m/e 297 (M+1)+.

Analysis ($C_{17}H_{20}ON_4O.0.15 H_2O$) Calcd: C, 68.27; H, 6.84; N, 18.74. Found: C, 68.42; H, 7.02; N, 18.42.

200 MHz NMR ($CDCl_3$) δ0.86 (t, J=7.5Hz, 3H ), 1.37 (m, 2H), 1.69 (m, 2H), 2.68 (t, J=7.5Hz, 2H), 3.70 (br s, 2H), 5.23 (s, 2H), 6.49 (dd, J=3.5, 1Hz, 1H ), 6.60 (d, J=8Hz, 2H), 6.81 (d, J=8Hz, 2H ), 6.91 (d, J=3.5Hz, 1H), 7.51 (d, J=1Hz. 1H).

Step D: 3-n-Butyl-4-[4-(2-carboxybenzamido)benzyl]-5-2-furyl-4H-1,2,4-triazole Reaction of 4-(4-aminobenzyl)-S-n-butyl-5-(2-furyl)-4H-1,2,4-triazole with phthalic anhydride according to the procedure of Example 1, Part F, gave (after evaporation from methanol 8× to remove THF) 85% of a white powder, mp 169.5°–171° C. homogeneous by TLC in 90:10:1$CH_2Cl_2$—MeOH-AcOH; mass spectrum (FAB) m/e 445 (M+1)+.

Analysis ($C_{25}H_{24}N_4O_4.0.4 H_2O$) Calcd: C, 66.48; H, 5.53; N, 12.40. Found: C, 66.35; H, 5.71; N, 12.52.

300 MHz NMR ($CD_3OD$) δ0.95 (t, J=7.5Hz, 3H), 1.43 (m, 2H), 1.71 (m, 2H), 2.83 (t, J=7.5Hz, 2H), 5.53 (s, 2H), 6.67 (dd, J=3.5, 1Hz, 1H), 7.03 (d, J=3.5 Hz, 1H), 7.08 (d, J=8Hz, 2H), 7:5–7.7 (m, 5H), 7.77 (d, J=1Hz, 1H), 8.03 (d, J=8Hz, 1H);

300 MHz NMR (DMSO-$d_6$) δ10.38 (s, 1H), 12.95 (v br s, 1H).

EXAMPLE 10

Preparation of 3-n-Butyl-4-[4-(2-carboxybenzamido)benzyl]-5-(4-pyridyl)-4H-1,2,4-triazole

Step A: Ethyl Valerate Isonicotinoylhydrazone

A mixture of 2.46 g (17.9 mmole) of isonicotinic hydrazide and 50 ml of ethanol was stirred at −10° C. as a solution of 2.52 g (16.6 mmole) of ethyl valerimidate hydrochloride, in 46 ml of ethanol was added dropwise under protection from moisture. The mixture was maintained at −10° C. for three hours and then at 5° C. overnight. The filtered solution was concentrated, and the residue was flash chromatographed on silica gel (elution with 2.5% methanol in $CH_2Cl_2$) to provide 2.12 g (50%) of the titled compound as an oil which goes to a waxy solid at 5° C., homogeneous by TLC in 9:1 $CH_2Cl_2$—MeOH; mass spectrum (FAB) m/e 250 (M+1)+. NMR suggested that the product is a mixture of syn and anti-isomers.

300 MHz NMR ($CDCl_3$) δ0.75–0.9 (m, 3H), 1.1–1.35 (m, 5H), 1.4–1.65 (m, 2H), 2.25–2.4 (m, 2H), 4.0–4.2 (m, 2H), 7.52,7.59 (d, J=6Hz, 2H total), 8.55–8.65 (m, 2H), 9.36 (br s, 1H)

*prepared by method of A.J. Hill and I. Rabinowitz, *J. Am. Chem. Soc.*, 48, 734 (1926)

Step B: Preparation of 3-n-Butyl-4-(4-nitrobenzyl)-5-(4-pyridyl)-4H-1,2,4-triazole A mixture of 1.71 g (6.86 mmole) of ethyl valerate isonicotinoylhydrazone, 1.82 g (11.9 mmole) of 4-nitrobenzylamine (generated from the hydrochloride by partitioning between ether and saturated $Na_2CO_3$ solution), and 16 ml of ethanol was stirred at 50° C. for 1.5 hours (resulting in precipitation) and then diluted with additional ethanol (approx. 45 ml) and heated at 70° C. for three days. The mixture was then cooled and rotary evaporated. Flash chromatography of the residue on silica gel (elution with 2.5% methanol in $CH_2Cl_2$) yielded 760 mg (36%) of a pale yellow solid, mp 142°–142.5° C., homogeneous by TLC in 9:1 $CH_2Cl_2$—MeOH.

200 MHz NMR ($CDCl_3$) δ0.82 (t, J=7Hz, 3H), 1.33 (m, 2H), 1.72 (m, 2H), 2.60 (t, J=8Hz, 2H), 5.32 (s, 2H), 7.12 (d, J=8Hz, 2H), 7.26 (d, J=6Hz, 2H), 8.18 ( d, J=8Hz, 2H ), 8.61 ( d, J=6Hz, 2H )

Step C:
4-(4-Aminobenzyl)-3-n-butyl-5-(4-pyridyl)-4H-1,2,4-triazole

A sample of 3-n-butyl-4-(4-nitrobenzyl)-5-(4-pyridyl)-4H-1,2,4-triazole was reduced with stannous chloride according to the procedure of Example 1, Part E, except that the product was extracted from aqueous NaOH solution with multiple extractions of both ether and ethyl acetate. A quantitative yield was thus obtained of the amine as a pale yellow oil, which crystallized after prolonged standing at 5° C.: mp 63.5°–64.5° C., homogeneous by TLC in 9:1 $CH_2Cl_2$—MeOH; mass spectrum (FAB) m/e 308 (M+1)+.

200 MHz NMR ($CDCl_3$) δ0.84 (t, J=7Hz, 3H), 1.35 (m, 2H), 2.72 (m, 2H), 2.66 (t, J=7.5 Hz, 2H), 3.90 (br s, 2H), 5.06 (s, 2H), 6.60 (d, J=8Hz, 2H), 6.69 (d, J=8Hz, 2H), 7.45 (d, J=5.5Hz, 2H), 8.63 (d, J=5.5Hz, 2H).

Step D:
3-n-Butyl-4-[4-(2-carboxybenzamido)benzyl]-5-(4-pyridyl)-4H-1,2,4-triazole Acylation of 4-(4-aminobenzyl)-3-n-butyl-5-(4-pyridyl)-4H-1,2,4-triazole with phthalic anhydride following the procedure of Example 1, Part F, gave (after evaporation from methanol 2× to remove THF) a 63% yield of the product as a solid, mp 152°–153° C., homogeneous by TLC in 90:10:1$CH_2Cl_2$—MeOH—AcOH; mass spectrum (FAB) m/e 456 (M+1)+.

Analysis [$C_{26}H_{25}N_5O_3.H_2O.0.25C_4H_{10}O$ (ether)-]Calcd: C, 65.90; H, 6.04; N, 14.23. Found: C, 65.74; H, 6.26; N, 14.13.

300 MMz NMR (DMSO-$d_6$) δ 0.86 (t, J=7.5Hz, 3H), 1.36 (m, 2H), 1.66 (m, 2It), 2.69 (t, J=8Hz, 2H), 5.34 (s, 2H), 6.92 (d, J=8Hz, 2H), 7.5–7.7 (m, 7H), 7.86 (d, J=8Hz, 1H), 8.69 (d, J=5.5Hz, 2H), 10.41 (s, 1H), 13.00 (br s, 1H).

EXAMPLE 11

Preparation of
3-n-Butyl-4-[4-(2-carboxybenzamido)benzyl]-5(carboxymethylthio)-4H-1,2,4-triazole A solution of 300 mg (0. 622 mmole ) of 3-n-butyl-5-(carbomethoxymethylthio)-4-[4-(2-carboxybenzamido)benzyl]-4H-1,2,4-triazole (Example 1) in a mixture of 496 μl (1.24 mmole) of 2.5 N NaOH and 0.8 ml of $H_2O$ was stirred at room temperature. After two hours, the solution was titrated to pH 5 with 2N HCl. The resulting precipitate was collected on a filter, washed with $H_2O$, and dried in vacuo over $P_2O_5$ to give 184 mg (60%) of a white solid, mp 135°–137° C., homogeneous by TLC in 80:20:2:2 $CHCl_3$-MeOH-AcOH-$H_2O$.

Analysis ($C_{23}H_{24}O_2S.1.5$ $H_2O$) Calcd: C, 55.74; H, 5.49; N, 11.31. Found: C, 56.03; H, 5.27; N, 11.34.

300 MHz NMR (DMSO-$d_6$) δ0.84 (t, J=7Hz, 3H), 1.31 (m, 2H), 1.55 m, 2H), 2.64 (t, J=7Hz, 2H), 3.96 (s, 2H), 5.14 (s, 2H), 7.09 (d, J=8Hz, 2H), 7.5–7.7 (m, 5H), 7.87 (d, J=8Hz, 1H), 10.50 (s, 1H), 12.95 (v br s, 2H)

EXAMPLE 12

Preparation of
3-n-Butyl-5-[2-(carbomethoxy)benzylthio]-4-[4-(2-carboxybenzamido)benzyl]-4H-1,2,4-triazole Step A:
3-n-Butyl-5-[2-(carbomethoxy)benzylthio]-4-(4-nitrobenzyl)-4H-1,2,4-triazole Alkylation of 5-n-butyl-2,4-dihydro-4-(4-nitrobenzyl)-3H-1,2,4-triazole-3-thione with a 50% excess of methyl 2-(bromomethyl)benzoate* following the proedure of Example 4, Part A, gave a 55% yield of an oil, homogeneous by TLC in 19:1 $CH_2Cl_2$—MeOH; mass spectrum (FAB) m/e 4 41 (M+1)+.

Analysis ($C_{22}H_{24}N_4O_4S.0.33$ $H_2O$) Calcd: C, 59.18; H, 5.57 ; N, 12.55. Found: C, 59.36; H, 5.62 ; N, 12.48.

300 MHz NMR ($CDCl_3$) δ0.87 (t, J=7Hz, 3H), 1.34 (m, 2H), 1.65 (m, 2H), 2.53 (t, J=7.5Hz, 2H), 3.87 (s, 3H), 4.79 ( s, 2H), 4.92 ( s, 2H ), 6.98 ( d, J=8Hz, 2H), 7.3–7.5 (m, 3H), 7.95 (dd, J=8, 1Hz, 1H), 8.08 (d, J=8Hz, 2H).

*R. M. Scrowston and D. C. Shaw, *J. Chem. Soc. Perkin Trans. I*, 749 (1976)

Step B:
4-(4-Aminobenzyl)-3-n-butyl-5-[2-(carbomethoxy)benzylthio]-4H-1,2,4-triazole This material was obtained by stannous chloride reduction of 3-n-butyl-5-[2-(carbomethoxy)benzylthio]-4-(4-nitrobenzyl)-4H-1,2,4-triazole according to the procedure of Example 4, Part B, except that the product was extracted with ethyl acetate instead of ether. The product was obtained in 95% yield as a sticky foam which solidified upon standing: mp 103–104° , homogeneous by TLC in 9:1 $CHCl_3$-MeOH; mass spectrum (FAB) m/e 411 (M+1)+

Analysis ($C_{22}H_{26}N_4O_2S$) Calcd: C, 64.36; H, 6.38; N, 13.65. Found: C, 64.07; H, 6.50; N, 13.34.

300 MHz NMR ($CDCl_3$) δ0.84 (t, J: 7.5Hz, 3H), 1.30 (m, 2H), 1.60 (m, 2H), 2.51 (t, J=8Hz, 2H), 3.65 (br s, 2H), 3.88 (s, 3H), 4.65 (s, 2H), 4.74 (s, 2H), 6.51 (d, J=8Hz, 211 ), 6.67 (d, J=8Hz, 2H ), 7.3–7.45 (m, 3H), 7.95 (dd, J=8, 1Hz, 1H).

Step C:
3-n-Butyl-5-[2-(carbomethoxy)benzylthio]-4-[4-(2-carboxybenzamido)benzyl]-4H-1,2,4-triazole Treatment of 4-(4-aminobenzyl)-3-n-butyl-5-[2-(carbomethoxy)benzylthio]-4H-1,2,4-triazole with phthalic anhydride according to the procedure of Example 4, Part C, gave 86% of an off-white solid, mp 106°–108° C., homogeneous by TLC in 90:10:1 $CHCl_3$-MeOH-AcOH; mass spectrum (FAB) m/e 559 (M+1)+.

Analysis ($C_{30}H_{30}N_4O_5S$) Calcd: C, 64.50; H, 5.41; N, 10.03. Found: C, 64.12; H, 5.61; N, 9.82.

300 MHz NMR (DMSO-$d_6$) δ0.84 (t, J=7Hz, 3H ), 1.29 (m, 2H), 1.53 (m, 2H), 2.59 (t, J=8Hz, 2H), 3.82 (s, 3H), 4.64 (s, 2H), 4.92 (s, 2H), 6.89 (d, J=8Hz, 2H), 7.35–7.7 (m, 8H), 7.88 (m, 2H), 10.36 (s, 1H), 13.0 (v br s, 1H).

EXAMPLE 13

Preparation of
3-n-Butyl-4-[4-(2-carboxybenzamido)benzyl]-5-(2-carboxybenzylthio)-4H-1,2,4-triazole A solution of 112 mg (0.2 mmole) of 3-n-butyl-5-[2-(carbomethoxy)benzylthio]-4-[4-(2-carboxybenzamido)benzyl]-4H-1,2,4-triazole in a mixture of 0.5 ml (1.25 mmole) of 2.5 N NaOH and 0.4 ml of $H_2O$ was stirred at room temperature in a stoppered flask for approximately 24 hours. The solution was titrated to pH 1.8 with 2N HCl resulting in heavy precipitation. The solid was collected on a filter and washed well with $H_2O$. After drying, the solid was leached with $CH_2Cl_2$ at room temperature to remove a small amount of starting material. The product was isolated and dried in vacuo over $P_2O_5$ at room temperature to yield 90 mg (76%) of a cream-colored solid, mp 134°–136° C. (preliminary swelling), homogeneous by TLC in 90:10:1 $CH_2Cl_2$—MeOH-AcOH; mass spectrum (FAB) m/e 544 (M+).

Analysis: ($C_{29}H_{28}N_4O_5S.0.1\ H_2O.0.5\ CH_2Cl_2$) Calcd: C, 60.16; H, 5.00; N, 9.52. Found: C, 59.86; H, 5.12; N, 9.48.

300 MHz NMR (DMSO-$d_6$) δ0.84 (t, J=7Hz, 3H), 1.29 (m, 2H), 1.54 (m, 2H), 2.64 (t, J=7.5Hz, 2H), 4.69 (s, 2H), 4.97 (s, 2H), 6.94 (d, J=8 Hz, 2H), 7.35–7.7 (m, 8H), 7.87 (d, J=8 Hz, 1H), 7.94 (d, J=8 Hz, 1H), 10.37 (s, 1H), 13.05 (v br s, 2H); presence of a small amount of $CH_2Cl_2$ also confirmed.

EXAMPLE 14

Preparation of 3-n-Butyl-5-(carbomethoxymethylthio)-4-[(2'-carboxybiphenyl-4-yl)methyl]-4H-1,2,4-triazole

Step A:
N-[[2'-(t-Butoxycarbonyl)biphenyl-4-yl]-methyl]phthalimide

A mixture of 2.99 g (8 mmole, based on 93% purity) of 4-bromomethyl-2'-(t-butoxycarbonyl)biphenyl (EP 253,310), 1.63 g (8.8 mmole) of potassium phthalimide, and 24 ml of dry DMF was stirred at room temperature for seven hours and then partitioned between 200 ml of ether and 250 ml of $H_2O$. The organic phase was washed with 4×250 ml of $H_2O$, then dried (MgSO$_4$), filtered, and concentrated. The residue was leached twice with hot ether (15–20 ml), which was decanted off after cooling. The remaining solid was collected on a filter, washed with petroleum ether, and dried to yield 2.08 g of colorless crystals, mp 108.5°–109°, homogeneous by TLC in 4:1 hexane-EtOAc. The residue from evaporation of the mother liquor was triturated with two portions of ether to give a second crop of colorless crystals: 0.58 g, mp. 122°–123° (preliminary softening). Despite the difference in melting point, the second crop was identical to the first by NMR and TLC.

Analysis: ($C_{26}H_{23}NO_4$) Calcd: C, 75.53; H, 5.61; N, 3.39. Found: C, 75.25; H, 5.75; N, 3.18.

300 MHz NMR (CDCl$_3$) δ1.17 (s, 9H), 4.90 (s, 2H), 7.2–7.9 (m, 12H)

Step B:
4-Aminomethyl-2'-(t-butoxycarbonyl)biphenyl

A mixture of 2.62 g (6.35 mmole) of N-[[2'-(t-butoxycarbonyl)biphenyl-4-yl]methyl]phthalimide, 1.21 ml (1.25 g, 25 mmole) of 100% hydrazine hydrate, and 35 ml of absolute ethanol was stirred at room temperature for 7.5 hours. During this time all of the solid gradually dissolved, followed by precipitation. Glacial acetic acid (3.7 ml) was added, and stirring was continued overnight. The white solid was then removed by filtration, and the filtrate was concentrated at room temperature. The residual oil was taken up in 100 ml of ether and washed with 2×50 ml of saturated aqueous Na$_2$CO$_3$ solution. Next, the product was extracted by shaking the ethereal solution with 50 ml of 0.5 N HCl. The aqueous layer was separated and basified by addition of excess saturated Na$_2$CO$_3$. The product, which oiled out, was extracted with 100 ml of ether. The ether phase was dried (Na$_2$SO$_4$), filtered, and concentrated at 30° C. to give 1.58 g (88%) of a very pale yellow, viscous oil, homogeneous by TLC in 95:5:0.5 $CH_2Cl_2$—MeOH-concd NH40H.

Analysis ($C_{18}H_{21}NO_2.0.25H_2O$) Calcd: C, 75.10; H, 7.53; N, 4.87. Found: C, 75.14; H, 7.39; N, 4.78.

300 MHz NMR (CDCl$_3$) δ1.27 (s, 9H), 1.50 (br s, 2H), 3.92 (s, 2H), 7.2–7.8 (m, 8H)

Step C: Methyl N-[[2'-(t-Butoxycarbonyl)biphenyl-4-yl]methyl]dithiocarbamate A solution of 1.415 g (5 mmol) of 4-aminomethyl-2'-(t-butoxycarbonyl)biphenyl and 751 μl (545 mg, 5.4 mmol) of triethylamine in 5 ml of methanol was stirred under $N_2$ at room temperature as a solution of 342 μl (434 mg, 5.7 mmole) of carbon disulfide in 2 ml of methanol was added dropwise over about 10 minutes. After 2.5 hours, the solution was cooled in an ice-methanol bath, and a solution of 311 μl (710 mg, 5 mmole) of methyl iodide in 2 ml of methanol was added dropwise over about 10 minutes. The cooling bath was removed, and the solution was allowed to warm to room temperature. After two hours, the solution was concentrated at 25° C. The residue was partitioned between 50 ml of ether plus 10 ml of $CH_2Cl_2$ and 50 ml of 0.2 N HCl. The organic phase was washed with 25 ml of saturated NaCl solution (aqueous), dried over MgSO$_4$, filtered, and concentrated. Crystallization of the residual oil from ether yielded 1.57 g (84%) of nearly colorless crystals, mp 127.5°–128.5° C., satisfactory purity by TLC in 4:1 hexane-EtOAc; mass spectrum (FAB) m/e 374 (M+1)+.

Analysis ($C_{20}H_{23}NO_2S_2$) Calcd: C, 64.31; H, 6.21; N, 3.75. Found: C, 64.54; H, 6.46; N, 3.82.

300 MHz NMR (CDCl$_3$) δ1.28 (s, 9H), 2.66 (2, 3H), 4.97 (d, J=5Hz, 2H), 7.13 (br m, 1H), 7.2–7.8 (m, 8H)

Step D: Preparation of 4-[[2'-(t-Butoxycarbonyl)biphenyl-4-yl]methyl]-3-thiosemicarbazide A mixture of 1.53 g (4.1 mmole) of methyl N-[[2'-(t-butoxycarbonyl)biphenyl-4-yl]methyl]-dithiocarbamate, 796 μl (820 mg, 16.4 mmole) of hydrazine hydrate, and 10 ml of absolute ethanol was stirred at reflux under $N_2$. After two hours, the resulting solution was cooled and concentrated. The residual oil was chromatographed on a column of silica gel (elution with 99:1 and then 98:2 $CH_2Cl_2$: MeOH) to give (after concentration and vacuum-drying) 1.15 g (79%) of a stiff, white foam, mp >45° C. (gradual); homogeneous by TLC in 19:1 $CH_2Cl_2$—MeOH; mass spectrum (FAB) m/e 358 (M+1)+.

Analysis ($C_{19}H_{23}N_3O_2S.0.1\ H_2O$) Calcd: C, 63.51; H, 6.51; N, 11.70. Found: C, 63.41; H, 6.50; N, 11.54.

300 MHz NMR (CDCl$_3$) δ 1.28 (s, 9H), 3.76 (br s, 2H), 4.90 (d,J=5Hz, 2H), 7.2–7.8 (m, 9H)

Step E: Preparation of 4-[[2'-(t-Butyoxycarbonyl)biphenyl-4-yl]methyl]-5-n-butyl-2,4-dihydro-3H-1,2,4-triazole-3-thione A solution of 1.11 g (3.1 mmole) of 4-[[2'-(t-butoxycarbonyl)biphenyl-4-yl]methyl]-3-thiosemicarbazide and 792 μl (745 mg, 4.6 mmole) of trimethyl orthovalerate in 10 ml of 2-methoxyethanol was stirred at reflux under N₂ for 15 hours. The cooled solution was concentrated, and the residue was purified by column chromatography on silica gel (gradient elution with 0–1% methanol in CH₂Cl₂) to give a gum which could be crystallized by trituration with petroleum ether. The product (828 mg, 63%, mp 135°–137° C.) was homogeneous by TLC in 19:1 CH₂Cl₂—MeOH; mass spectrum (FAB) m/e 424 (M+1).

Analysis ($C_{24}H_{29}N_3O_2S$) Calcd: C, 68.05; H, 6.90; N, 9.92. Found: C, 67.95; H, 6.65; N, 9.84.

300 MHz NMR (CDCl₃) δ 0.87 (t, J=7Hz, 3H), 1.22 (s, 9H), 1.32 (m, 2H), 1.62 (m, 2H), 2.48 (t, J=7Hz, 2H), 5.27 (s, 2H), 7.2–7.5 (m, 7H), 7.74 (d, J=8Hz, 1H)

Step F: Preparation of 4-[[2'-(t-Butoxycarbonyl)biphenyl-4-yl]methyl]-3-n-butyl-5-(carbomethoxymethythio)-4H-1,2,4-triazole To a stirred solution of 636 mg (1.5 mmole) of 4-[[2'-(t-butoxycarbonyl)biphenyl-4-yl]methyl]-5-n-butyl-2,4-dihydro-3H-1,2,4-triazole-3-thione in 4 ml of dry CH₂Cl₂ was added 435 μl (322 mg, 2.5 mmole) of N,N-diisopropylethylamine followed by 219 μl (271 mg, 2.5 mmole) of methyl chloroacetate. The resulting solution was stirred at room temperature under N₂ for 7.5 hours and then partitioned between 50 ml of ether and 25 ml of saturated aqueous NH₄Cl solution. The organic layer was washed with an additional 25 ml of saturated NH₄Cl and then dried over MgSO₄. The filtered solution was concentrated, and the residual oil was chromatographed on a column of silica gel (elution with a gradient of 0–5% isopropanol in CH₂Cl₂) to give 639 mg (86%) of a colorless gum, homogeneous by TLC in 97:3 CH₂Cl₂—iPrOH; mass spectrum (FAB) m/e 496 (M+1)+.

Analysis ($C_{27}H_{33}N_3O_4S$) Calcd: C, 65.43; H, 6.71; N, 8.48. Found: C, 65.05; H, 6.82; N, 8.41.

300 MHz NMR (CDCl₃) δ0.90 (t, J=7Hz, 3H), 1.24 (s, 9H), 1.40 (m, 2H), 1.72 (m, 2H), 2.67 (t,J=7.5 Hz, 2H), 3.74 (s, 3H), 4.03 (s, 2H), 5.19 (s, 2H), 7.09 (d, J=8Hz, 2H), 7.2–7.5 (m, 5H), 7.79 (d, J=8 Hz, 1H)

Step G: Preparation of 3-n-Butyl-5-(carbomethoxymethylthio)-4-[(2'-carboxybiphenyl-4-yl) methyl]-4H-1,2,4-triazole To 496 mg (1 mmole) of 4-[[2'-(t-butoxycarbonyl)-biphenyl-4-yl]methyl]-3-n-butyl-5-(carbomethoxymethylthio)-4H-1,2,4-triazole was added 3 ml of anhydrous trifluoroacetic acid. The resulting solution was stirred at room temperature under N₂ (bubbler) for 24 hours and then evaporated in a stream of N₂. The clear residual gum was treated with approximately 25 ml of ether and stirred vigorously in a stoppered flask, resulting in crystallization. After about 20 minutes, the solid was collected on a filter, washed with ether, and dried in vacuo to give 426 mg (97%) of white crystals, mp 157.5°–159° C., homogeneous by TLC in 95:5:0.1 CH₂Cl₂—MeOH-AcOH; mass spectrum (FAB) m/e 440 (M+1)+.

Analysis ($C_{23}H_{25}N_3O_4S$) Calcd: C, 62.85; H, 5.73; N, 9.56. Found: C, 62.70; H, 5.86; N, 9.40.

300 MHz NMR (DMSO-d₆) δ 0.82 (t, J=7Hz, 3H), 1.29 (m, 2H), 1.54 (m, 2H), 2.64 (t, J=7Hz, 2H), 3.64 (s, 3H), 4.05 (s, 2H), 5.23 (s, 2H), 7.14 (d, J=8 Hz, 2H), 7.3–7.6 (m, 5H), 7.73 (d, J=8 Hz, 1H), 12.76 (br s, 1H)

EXAMPLE 15

Preparation of 3-n-Butyl-5-(4-chlorobenzylthio)-4-[(2'-(1H-tetrazol-5-yl)biphenyl-4-yl)methyl]-4H-1,2,4-triazole

Step A: 4-Azidomethyl-2'-cyanobiphenyl

A mixture of 1.97 g (7.25 mmole) of 4-bromomethyl-2'-cyanobiphenyl (EP 253,310), 445 mg (9.1 mmole) of lithium azide and 5 ml of dry DMSO was stirred at room temperature under nitrogen for one hour and then partitioned between 100 ml of ether and 100 ml of H₂O. The organic phase was washed with 3×100 ml of H₂O, then dried (MgSO₄), filtered, and concentrated in vacuo to give a residual oil which solidified on standing. This solid was triturated with petroleum ether, collected on a filter, washed with petroleum ether and dried overnight to yield 1.15 g (68%) of the title compound as white crystals, mp 69°–70° C.; mass spectrum (EI) m/e 234 (M+). TLC in 4:1 hexane-EtOAc showed only minor impurities and the material was of sufficient purity to use in the next step.

300 MHz NMR (CDCl₃) δ4.41 (s, 2H), 7.4–7.7 (m, 7H), 7.75 ( d, J=8Hz, 1H )

Step B: 4-[(2'-Cyanobiphenyl-4-yl)methyl]-3-thiosemicarbazide

A mixture of 1.12 g (4.8 mmole) of 4-azidomethyl-2'-cyanobiphenyl, 1.57 g (6.0 mole) of triphenylphoshine, and 8 ml of carbon disulfide was stirred at room temperature under nitrogen for 5.5 hours and then was warmed (water bath) and evaporated to dryness first under a stream of nitrogen and then under reduced pressure. This residue (presumably (2'-cyanobiphenyl-4-yl)methyl isothiocyanate) was dissolved in 12 ml of THF and stirred vigorously at room temperature as 0.699 ml (720 mg, 14.4 mmole) of hydrazine hydrate was added in one bolus. The mixture immediately turned opaque and milky but soon clarified with the separation of a small additional liquid phase. After ten minutes the mixture was partitioned between 40 ml of ether, 25 ml of CH₂Cl₂, and 75 ml of H₂O. Some solid formed and this was filtered off (1.04 g after drying over P₂O₅ in vacuo) and recrystallized from EtOAc to give 661 mg of the title compound as white crystals, mp 163°–163.5°, Additional material was obtained by re-working the mother liquors and the organic layer of the filtrate affording a, total yield (three crops) was 1.01 g (75% from 4-azidomethyl-2'-cyanobiphenyl), satisfactory purity by TLC in 19:1CH₂Ci:MeOH; mass spectrum (FAB) m/e 283 (M+1)+.

Analysis ($C_{15}H_{14}N_4S$) Calcd: C, 63.80; H, 5.00; N, 19.84; S, 11.36. Found: C, 63.59; H, 4.93; N, 19.60: S, 11.42.

300 MHz NMR (DMSO-d₆) δ4.55 (s, 2H), 4.80 (d, J=6Hz, 2H), 7.4–7.8 (m, 7H), 7.94 ( d, J=8Hz, 1H), 8.45 (brm, 1H), 8.80 (s, 1H)

Step C: 5-n-Butyl-4-[(2'-cyanobiphenyl-4-yl)methyl]-2,3-dihydro-3H-1,2,4-triazole-3-thione A mixture of 800 mg (2.84 mmole) of cyanobiphenyl-4-yl)methyl]-3-thiosemicarbazide, 0.611 ml (575 mg, 3.55 mmole) of trimethyl orthovalerate, and 4 ml of 2-methoxyethanol was stirred at reflux under nitrogen for four hours and then was evaporated to dryness under a stream of nitrogen while maintaining the bath temperature at 125°. The residue so obtained was recrystallized from nitromethane (approx. 4 ml) and the white crystalline product was filtered and washed with a small volume of nitromethane and then with a mixture of petroleum ether and ether before being dried overnight. 624 mg (63%) of white crystals having acceptable purity by TLC in 98:2 $CH_2Cl_2$: MeOH; mp 168°–168.5° C.; mass spectrum (FAB) m/e 349 $(M+1)^+$.

Analysis ($C_{20}H_2ON_4S$) Calcd: C, 68.93; H, 5.79; N, 16.08. Found: C, 68.69; H, 5.79; N, 15.93.

300 MHz NMR ($CDCl_3$) δ0.88 (t, J=7Hz, 3H), 1.35 (m, 2H), 1.62 (m, 2H), 2.54 (t, J=7Hz, 2H), 5.33 (s, 2H), 7.35–7.7 (m, 7H), 7.77 (d, J=8Hz, 1H) 11.06 (br s, 1H).

Step D:
3-n-Butyl-S-(4-chlorobenzylthio>-4-[(2'-cyanobiphenyl-4-yl)methyl]-4H-1,2,4-triazole A mixture of 278 mg (0.8 mmole) of 5-n-butyl-4-[(2'-cyanobiphenyl-4-yl)methyl]-2,4-dihydro-5H-1,2,4-triazole-3-thione, 258 mg (1.6 mmole) of 4-chlorobenzyl chloride, 0.278 ml (206 mg, 1.6 mmole), and 2.5 ml of 2-methoxyethanol was stirred at room temperature under nitrogen overnight and then was evaporated to dryness in vacuo. The viscous residual oil so obtained was partitioned between a mixture of 20 ml of ether, 10 ml of $CH_2Cl_2$ and 30 ml of 0.2N HCl. The organic layer was further washed with 30 ml of 0.2N HCl and then with 15 ml of satd. NaCl solution before being dried ($MgSO_4$), filtered, and evaporated to dryness. The residual oil was purified on a silica gel column (gradient elution with 0–1% methanol in $CH_2Cl_2$). Fractions containing the required product were pooled and evaporated to dryness. The residue was redissolved in $CH_2Cl_2$, filtered and evaporated to dryness in vacuo to give 338 mg (71% yield) of the title compound as a slightly cloudy gum, virtually homogeneous by TLC in 98:2 $CH_2Cl_2$—MeOH; mass spectrum (FAB) m/e 473 $(M+1)^+$.

Analysis ($C_{27}H_{25}ClN_4S.0.25H_2O$) Calcd: C, 67.91; H, 5.38; N, 11.73. Found: C, 67.87; H, 5.50; N, 11.68.

300 MHz NMR ($CDCl_3$) δ0.89 (t, J=7Hz, 3H), 1.35 (m, 2H), 1.67 (m, 2H), 2.60 (t, J=8Hz, 2H), 4.33 (s, 2H), 4.92 (s, 2H), 6.97, 7.24 (d, J=9Hz, each 2H), 7.4–7.7 (m, 7H), 7.77 (d, J=8Hz, 1H).

Step E:
3-n-Butyl-5-(4-chlorobenzylthio)-4-[(2'-(1H-tetrazol-5-yl)biphenyl-4-yl)methyl]-4H-1,2,4-triazole A mixture of 150 mg <0.32 mmole) of 3-n-butyl-5-<4-chlorobenzylthio)-4-[(2'-cyanobiphenyl-4-yl)methyl]-4H-1,2,4-triazole, 78 mg <0.38 mmole) of trimethyltin azide and 3 ml of dry toluene were stirred at reflux under nitrogen. Two additional amounts of trimethyltin azide (78 mg, 0.38 mmole each time) were added after four hours and twenty-nine hours respectively and additional toluene was added after 24 hours to facilitate the stirring. After forty-eight hours the mixture was diluted with toluene and filtered. The solid on the filter was washed with toluene and then ether. A solution of this material in 50 ml of MeOH was treated with approximately 2 g of silica gel and stirred at room temperature for 30 minutes. The slurry was evaporated to dryness to give a free flowing powder, which was well dried in vacuo. This material suspended in $CH_2Cl_2$, and the slurry was added to a silica gel column wet-packed in $CH_2Cl_2$. The column was developed with 9:1 $CH_2Cl_2$—MeOH and fractions containing the required product were pooled and evaporated to a white solid residue which was redissolved in $CH_2Cl_2$ and filtered.

Concentration of the filtrate in vacuo yielded 62 mg (37% yield) of the title compound as an off-white solid, mp 92°–93° C.; mass spectrum (FAB) m/e 516 $(M+1)^+$.

Analysis ($C_{27}H_{26}ClN_7S.0.6H_2O$) Calcd: C, 51.54; H, 5.20; N, 18.61. Found: C, 61.51; H, 5.15; N, 18.24.

300 MMz NMR (DMSO-$d_6$) δ0.80 (t, J=7.5Hz, 3H), 1.24 (sext, J=7.5Hz, 2H), 1.48 (quint, J=7.5Hz, 2H), 2.55 (t, J=7.5Hz, 2H), 4.29 (s, 2H), 5.02 (s, 2H), 6.84 (d, J=8Hz, 2H), 7.03 (d, J=8Hz, 2H), 7.3–7.7 (m, 8H).

EXAMPLE 16

Preparation of 3-n-Butyl-5-(4-chlorobenzylsulfinyl)-4-[[2'-(1H-tetrazol-5-yl)biphenyl-4-yl]methyl]-4H-1,2,4-triazole To a stirred solution of 113 mg (0.22 mmole) of 3-n-butyl-5-(4-chlorobenzylthio)-4-[[2'-(1H-tetrazol-5-yl)biphenyl-4-yl]methyl]-4H-1,2,4-triazole (from Example 15) in 1.2 ml of glacial acetic acid was added dropwise 1.2 ml of 30% hydrogen peroxide (aqueous). A small amount of additional acetic acid was then added to give a clear solution, which was stirred at room temperature in a stoppered flask. After 17.5 hours, when NMR indicated complete conversion to product, the solution was partitioned between 15 ml of ethyl acetate and 15 ml of dilute HCl (pH 1.5–2.0). The aqueous phase was extracted with two more portions of ethyl acetate. The combined organic fractions were washed with dilute HCl, then dried over $MgSO_4$, filtered, and concentrated in vacuo.

Trituration of the residue gave a white solid: 77 mg (65%), mp 208°–209° C. dec. (preliminary discoloration); mass spectrum (FAB) m/e 532 $(M+1)^+$.

Analysis ($C_{27}H_{26}ClNOS.0.25 H_2O$) Calcd: C, 60.43; H, 4.98; N, 18.28. Found: C, 60.33, H, 4.98; N, 18.32.

300 MHz NMR (DMSO-$d_6$) δ0.79 (t, J=7.5Hz, 3H), 1.25 (m, 2H), 1.46 (m, 2H), 2.59 (m, 2H), 4.75 (ABq, J=12.5Hz, 2H), 5.33 (ABq, J=16Hz, 2H), 6.89, 7.03 (d, J=7Hz, each 2H), 7.29, 7.40 (d, J=8Hz, each 2H), 7.4–7.75 (m, 4H).

EXAMPLE 17

Preparation of 3-n-Butyl-5-(4-chlorobenzylsulfonyl)-4-[[2'-(1H-tetrazol-5-yl)biphenyl-4-yl]methyl ]-4H-1,2,4triazole Step A: 3-n-Butyl-5-(4-chlorobenzylsulfonyl)-4-[(2'-cyanobiphenyl-4-yl)methyl]-4H-1,2,4-triazole A stirred solution of 47 mg, (0.1 mmole) of 3-n-butyl-5-(4-chlorobenzylthio)-4-[(2'-cyanobiphenyl-4-yl)methyl]-4H-1,2,4-triazole (from Example 15, Step D) in 0.3 ml of dry $CH_2Cl_2$ was treated with 63 mg (0.3 mmole) of 80–85% m-chloroperoxybenzoic acid, and stirring was continued at room temperature. Precipitation began within a few minutes. After 2.5 hours, when TLC (19:1 $CH_2Cl_2$—MeOH) indicated complete reaction, the mixture was taken up in 25 ml of ethyl acetate and washed with 3×25 ml of saturated $Na_2CO_3$(aqueous). The organic phase was dried over $MgSO_4$, filtered, and concentrated in vacuo to give to 48 mg (95%) of the title compound as a gum, homogeneous by TLC in 19:1 $CH_2Cl_2$—MeOH; mass spectrum (FAB) m/e 505 $(M+1)^+$.

300 MHz NMR ($CDCl_3$) δ0.87 (t, J=7Hz, 3H), 1.32 (m, 2H), 1.66 (m, 2H), 2.60 (t, J=8Hz, 2H), 4.78 (s, 2H), 5.25 (s, 2H), 6.94 (d, J=7Hz, 2H), 7.2–7.5 (m, 8H), 7.63 (m, 1H), 7.74 (d, J=8Hz, 1H).

Step A: 3-n-Butyl-5-(4-chlorobenzylsulfonyl)-4-[[2'-(1H-tetrazol-5-yl)biphenyl-4-yl]methyl]-4H-1,2,4-triazole The title compound was prepared from 3-n-butyl-5-(4-chlorobenzylsulfonyl)-4-[(2'-cyanobiphenyl-4-yl)methyl]-4H-1,2,4-triazole (Step A) according to the procedure of Example 15, Step E, except that 3.5 equivalents of trimethyltin azide were added at the start, and the column was eluted with a gradient of 0–10% methanol in $CH_2Cl_2$. The product was obtained in 17% yield as a glass, which was transformed to a powder upon scraping: mp 180°–182° C. dec.; homogeneous by TLC in 4:1 $CH_2Cl_2$—MeOH; mass spectrum (FAB) m/e 548 $(M+1)^+$.

Analysis ($C_{27}H_{26}ClN_7O_2S$.0.5 $H_2O$0.3 $CH_2Cl_2$) Calcd: C, 56.28; H, 4.78; N, 16.83. Found: C, 56.20; H, 4.70; N, 16.51.

300 MHz NMR ($CDCl_3$) δ0.93 (t, J=7Hz, 3H), 1.40 (m, H), 1.75 (m, 2H), 2.73 (t, J=8Hz, 2H), 4.84 (s, H), 5.22 (s, 2H), 6.98 , 7.17 (d, J=7.5Hz, each H), 7.2–7.6 (m, 9H), 8.19 (dd, J=8,1Hz, 1H).

EXAMPLE 18

Preparation of 3-n-Butyl-5-(4-nitrobenzylthio)-4-[[2'-(1H-tetrazol-5-yl)biphenyl-4-yl]methyl]-4H-1,2,4-triazole Step A:
3-n-Butyl-4-[(2'-cyanobiphenyl-4-yl)methyl]-5-(4-nitrobenzylthio)-4H-1,2,4-triazole A mixture of 209 mg (0.6 mmole) of 5-n-butyl-4-[(2'cyanobiphenyl-4-yl)methyl]-2,4-dihydro-3H-1,2,4-triazole-3-thione (from Example 15, Step C), 209 μl (155 mg, 1.2 mmole) of N,N-diisopropylethylamine, 259 mg (1.2 mmole) of 4-nitrobenzyl bromide, and 2 ml of 2-methoxyethanol was stirred under $N_2$ at room temperature for 2 hours. The solution was then concentrated in vacuo at 30° C. to small volume and then partitioned between a mixture of 25 ml of ether, 5 ml of ethyl acetate, and 25 ml of 0.2 N HCl. The organic phase was washed with an additional portion of 0.2 N HCl and then with saturated NaCl solution. The organic solution was dried ($MgSO_4$), filtered, and concentrated. The residue was purified by column chromatography on silica gel (gradient elution with 0–1.6% methanol in $CH_2Cl_2$). Concentration of the combined product fractions yielded 252 mg (84%) of the title compound as a sticky foam, homogeneous by TLC in 19:1 $CH_2Cl_2$—MeOH; mass spectrum (FAB) m/e 484 $(M+1)^+$.

Analysis ($C_{27}H_{25}N_5O_2S$.0.18 $CH_2Cl_2$) Calcd: C, 65.43; H, 5.12; N, 14.04. Found: C, 65.68; H, 5.38; N, 13.82.

300 MHz NMR ($CDCl_3$) δ0.87 (t, J=7Hz, 3H), 1.34 (m, 2H), 1.67 (m, 2H), 2.61 (t, J=7.5Hz, 2H), 4.43 (s, 2H), 4.96 (s, 2H), 6.99 (d, J=8Hz, 2H), 7.4–7.55 (m, 6H), 7.64 (m, 1H), 7.76 (d, J=8Hz, 1H), 8.10 (d, J=8Hz, 2H).

Step B:
3-n-Butyl-5-(4-nitrobenzylthio)-4-[[2'-(1H-tetrazol-5-yl)biphenyl-4-yl]methyl]-4H-1,2,4-triazole A mixture of 232 mg (0.48 mmole) of 3-n-butyl-4-[(2'-cyanobiphenyl-4-yl)methyl]-5-(4-nitrobenzylthio)-4H-1,2,4-triazole (Step A), 346 mg (1.68 mmole) of trimethyltin azide, and 3 ml of dry toluene was stirred at reflux under $N_2$ for 2 days. The precipitate was collected on a filter and washed with a little toluene, then with ether. The solid was dissolved in warm methanol (~20 ml) and treated with approximately 1 g of silica gel. The mixture was stirred at room temperature for about 10 minutes and then concentrated and dried in vacuo. The resulting powder was added as a slurry in $CH_2Cl_2$ to the top of a silica gel column packed in this solvent. The column was eluted with 1% and then 10% methanol in $CH_2Cl_2$. The combined product fractions were concentrated to yield 219 mg (84%) of white solid, mp 88°–90° C., homogeneous by TLC in 9:1 $CH_2Cl_2$—MeOH; mass spectrum (FAB) m/e 527 $(M+1)^+$.

Analysis ($C_{27}H_{26}N_8O_2S$.0.2 $CH_2Cl_2$) Calcd: C, 60.09; H, 4.89; N, 20.62. Found: C, 59.92; H, 4.93; N, 20.46.

300 MHz NMR (DMSO-$d_6$) δ0.80 (t, J=7.5 Hz, 3H), 1.24 (m, 2H), 1.48 (m, 2H), 2.56 (t, J=7.5Hz, 2H), 4.41 (s, 2H), 5.03 (s, 2H), 6.88, 7.04 (d, J=8Hz, each 2H), 7.45–7.6 (m, 6H), 8.14 (d, J=8Hz, 2H).

EXAMPLE 19

Preparation of 3-n-Butyl-5-(4-nitrobenzylsulfinyl)-4-[[2'-(1H-tetrazol-5-yl)biphenyl-4-yl]methyl]-4H-1,2,4-triazole A mixture of 120 mg (0.23 mmole) of 3-n-butyl-5-(4-nitrobenzylthio)-4-[[2'-(1H-tetrazol-5-yl)-biphenyl-4-yl]methyl]-4g-1,2,4-triazole (from Example 18), 1.5 ml of glacial acetic acid, and 1.5 ml of 30% hydrogen peroxide (aqueous) was stirred at room temperature in a stoppered flask. The insoluble, gummy material initially present was gradually replaced by a white precipitate. After approximately 22 hours, the precipitate was collected on a filter and washed with $CH_2Cl_2$ followed by ether. Recrystallization from 2-methoxyethanol (approx. 1 ml) afforded 64 mg (50%) of white crystals, mp 222°–223° C.; mass spectrum (FAB) m/e 543 $(M+1)^+$.

Analysis ($C_{27}H_{26}N_8O_3S$.0.5 $H_2O$) Calcd: C, 58.78; It, 4.93; N, 20.32. Found: C, 58.52; 11, 4.86; N, 20.09.

300 MHz NMR (DMSO-$d_6$) δ0.81 (t, J=7.5Hz, 3H), 1.25 (m, 2H), 1.49 (m, 2H), 2.59 (t, J=7.5Hz, 2H), 4.88 (ABq, J=12Hz, 2H), 5.30 (ABq, J=16Hz, 2H), 7.00 (ABq, J=8Hz, 4H), 7.45–7.7 (m, 6H), 8.20 (d, J=8Hz, 2H).

EXAMPLE 20

Preparation of 3-n-Butyl-5-(cyclohexylmethylthio)-4-[[2'-(1H-tetrazol-5-yl)biphenyl-4-yl]methyl]-4H-1,2,4-triazole Step A:
3-n-Butyl-4-[(2'-cyanobiphenyl-4-yl)methyl]-5-(cyclohexylmethylthio)-4H-1,2,4-triazole A mixture of 147 mg (0.42 mmole) of 5-n-butyl-4-[(2'-cyanobiphenyl-4-yl)methyl]-2,4-dihydro-3H-1,2,4-triazole-3-thione (from Example 15, Step C), 146 μl (108 mg, 0.84 mmole) of N,N-diisopropylethylamine, 117 μl (148 mg, 0.84 mmole) of cyclohexylmethyl bromide, and 1.5 ml of 2-methoxyethanol was stirred under $N_2$ at 70° C. overnight and then at reflux for an additional 4 hours. The solution was concentrated in vacuo, and the residue was partitioned between 25 ml of ethyl acetate and 25 ml of 0.2 N HCl. The ethyl acetate layer was washed with saturated NACl, then dried over anhydrous $MgSO_4$, filtered, and rotary evaporated in vacuo. Column chromatography of the residue on silica gel (elution with a gradient of 0–0.8% methanol in $CH_2Cl_2$) afforded 111 mg (59%) title compound as an oil, homogeneous by TLC in 19:1 $CH_2Cl_2$—MeOH; mass spectrum (FAB) m/e 445 $(M+1)^+$.

Analysis ($C_{27}H_{32}N_4S \cdot 0.1\ H_2O$) Calcd: C, 72.63; H, 7.27; N, 12.55. Found: C, 72.45; H, 7.18; N, 12.46.

300 MHz NMR (CDCl$_3$) δ0.86 (t, J=7.5Hz, 3H), 0.9–1.9 (m, 15H), 2.64 (t, J=7.5Hz, 2H), 3.10 (d, J=7Hz, 2H), 5.11 (s, 2H), 7.15 (d, J=7.5Hz, 2H), 7.4–7.55 (m, 4H), 7.62 (m, 1H), 7.76 (d, J=8Hz, 1H).

Step B:
3-n-Butyl-5-(cyclohexylmethylthio)-4-[[2'-(1H-tetrazol-5-yl)biphenyl-4-yl]methyl]-4H-1,2,4-triazole Reaction of 3-n-butyl-4-[(2'-cyanobiphenyl-4-yl)methyl]-5-(cyclohexylmethylthio)-4H-1,2,4-triazole (Step A) with trimethyltin azide according to the procedure of Example 18, Step B, gave a 60% yield of the title compound as a white solid, mp 89°–91° C., homogeneous by TLC in 4:1 CH$_2$Cl$_2$—MeOH; mass spectrum (FAB) m/e 488 (M+1)$^+$.

Analysis ($C_{27}H_{33}N_7S \cdot 0.2\ H_2O \cdot 0.1\ CH_2Cl_2$) Calcd: C, 65.13; H, 6.78; N, 19.62. Found: C, 65.42; H, 6.94; N, 19.29.

300 MHz NMR (DMSO-d$_6$) δ0.82 (t, J=7.5Hz, 3H), 0.85–1.8 (m, 15H), 2.60 (t, J=7.5 Hz, 2H), 2.95 (d, J=7Hz, 2H), 5.16 (s, 2H), 6.99, 7.10 (d, J=8Hz, each 2H), 7.45–7.75 (m, 4H).

EXAMPLE 21

Preparation of
3-n-Butyl-5-(4-chlorobenzylthio)-4-[4-[2-(1H-tetrazol-5-yl)benzamido]benzyl]-4H-1,2,4-triazole Step A:
3-n-Butyl-5-(4-chlorobenzylthio)-4-(4-nitrobenzyl)-4H-1,2,4-triazole Reaction of 5-n-butyl-2,4-dihydro-4-(4-nitrobenzyl)-3H-1,2,4-triazole-3-thione with 4-chlorobenzyl chloride according to the procedure of Example 4, Step A (with reaction time shortened to 4.5 hours) gave a 90% yield of the title compound as an oil, homogeneous by TLC in 19:1 CH$_2$Cl$_2$—MeOH; mass spectrum (FAB m/e 417 (M+1)$^+$.

Analysis ($C_{20}H_{21}ClN_4O_2S \cdot 0.05\ CH_2Cl_2$) Calcd: C, 57.17; H, 5.05; N, 13.31. Found: C, 57.08; H, 5.01; N, 13.03.

300 MHz NMR (CDCl$_3$) δ0.86 (t, J=7.5Hz, 3H), 1.32 (m, 2H), 1.63 (m,2H), 2.52 (t, J=7.5 Hz, 2H), 4.33 (s, 2H), 4.33 (s, 2H), 4.92 (s, 2H), 6.97 (d, 9Hz, 2H) 7.20 (s, 4H), 8.13 (d, J=9Hz, 2H).

Step B:
4-(4-Aminobenzyl)-3-n-butyl-5-(4-chlorobenzlthio)-4H-1,2,4-triazole

Stannous chloride reduction of 3-n-butyl-5-(4-chlorobenzylthio)-4-(4-nitrobenzyl)-4H-1,2,4-triazole (Step A) using the procedure of Example 4, Step B, gave a 92% yield of the title compound as an oil, homogeneous by TLC in 9:1 CHCl$_3$-MeOH; mass spectrum (FAB) m/e 387 (M+1)$^+$.

Analysis ($C_{20}H_{23}ClN_4S \cdot 0.25\ H_2O$) Calcd: C, 61.36; H, 6.05; N, 14.32. Found: C, 61.74; H, 6.27; N, 13.96.

300 MHz NMR (CDCl$_3$) δ0.86 (t, J=7.5 Hz, 3H), 1.32 (m, 2H), 1.62 (m, 2H) 2.56 (t, J=8 Hz, 2H), 3.68 (br s, 2H), 4.72 (s, 2H), 6.54, 6.66 (d, J=9Hz, each 2H), 7.20 (s, 4H).

Step C:
3-n-Butyl-5-(4-chlorobenzylthio)-4-[4-(2-cyanobenzamido)benzyl]-4H-1,2,4-triazole A solution of 450 mg (1.16 mmole) of 4-(4-aminobenzyl)-3-n-butyl-5-(4-chlorobenzylthio)-4H-1,2,4-triazole (Step B), 438 μl (325 mg, 2.52 mmole) of N,N-diisopropylethylamine and 418 mg (2.53 mmole) of 2-cyanobenzyl chloride [R. Scholl and W. Neuberger, Monatsh. Chem. 33, 507 (1911)] in 10 ml of dry THF was stirred overnight at room temperature under N$_2$. The mixture was filtered, and the filtrate was concentrated in vacuo. The residue was dissolved in 50 ml of ethyl acetate and washed with 2×60 ml of saturated NaHCO$_3$ solution followed by 50 ml of saturated NACl. The organic phase was then dried (MgSO$_4$), filtered, and concentrated. A solution of the residue in CH$_2$Cl$_2$ was treated with approximately 2 g of silica gel, and the mixture was evaporated to give a dry powder, which was added as a slurry in hexane to the top of a silica gel column packed in the same solvent. The column was eluted briefly with hexane and then with a stepwise gradient from 1:1 hexane-EtOAc to 100% EtOAc. Two major products were eluted, the second of which correspond to the desired product. Fractions containing this material were combined and concentrated to give 229 mg (36%) of the title compound as a solid, mp 75°–77° C. dec., homogeneous by TLC in 1:3 hexane-EtOAc; mass spectrum (FAB) m/e 516 (M+1)$^+$.

Analysis [$C_{28}H_{26}ClN_5OS \cdot 0.4\ C_4H_8O_2$(ethyl acetate)]- Calcd: C, 64.48; H, 5.34; N, 12.71. Found: C, 64.29; H, 5.36; N, 12.60.

300 MHz NMR (CDCl$_3$) δ0.88 (t, J=7.5 Hz, 3H), 1.35 (m, 2H), 1.67 (m, 2H) 2.59 (t, J=7.5 Hz, 2H), 4.32 (m, 2H), 4.90 (s, 2H), 6.9–8.1 (m, 12H), 8.73 (s, 1H).

Step D:
3-n-Butyl-5-(4-chlorobenzylthio)-4-[4-[2-(1H-tetrazol-5-yl)benzamido]benzyl-4H-1,2,4-triazole Reaction of 3-n-butyl-5-(4-chlorobenzylthio)-4-[(2-cyanobenzamido)benzyl]-4H-1,2,4-triazole (Step C) with trimethyltin azide according to the method of Example 18, Step B, gave a 10% yield of the title compound as a pale yellow solid, mp 175°–176° C. dec. (preliminary shrinking), homogeneous by TLC in 4:1 CH$_2$Cl$_2$—MeOH; mass spectrum (FAB) m/e 559 (M+1)$^+$ Analysis [$C_{28}H_{27}ClN_8OS \cdot H_2O \cdot 0.03\ CH_2Cl_2$] Calcd; C, 56.40; H, 4.95; N, 18.60. Found: C, 56.38; H, 4.70; N, 18.22.

300 MHz NMR (DMSO-d$_6$) δ0.84 (t, J=7.5 Hz, 3H), 1.29 (m, 2H), 1.54 (m, 2H) 2.61 (t, J=7.5Hz, 2H), 4.31 (s, 2H), 4.99 (s, 2H), 6.92 (d, J=9 Hz, 2H), 7.3–7.7 (m, 9H) 7.86 (d, J=8 Hz, 1H), 10.82 (s, 1H)

EXAMPLE 22

Preparation of
3-n-Butyl-5-(4-chlorobenzylsulfinyl)-4-[4-[2-(1H-tetrazol-5-yl)benzamido]benzyl]-4H-1,2,4-triazole By treatment of 3-n-butyl-5-(4-chlorobenzylthio)-4-[4-[2-(1H-tetrazol-5-yl)benzamido]benzyl]-4H-1,2,4-triazole (from Example 21) with 30% hydrogen peroxide according to the procedure of Example 16, the title compound was obtained in 42% yield as a white solid, mp 150°–152° C.; mass spectrum (FAB) m/e 575 (M+1)+.

Analysis [$C_{28}H_{27}ClN_8O_2S \cdot 0.33\ H_2O$] Calcd: C, 57.88; H, 4.80; N, 19.29. Found: C, 57.90; H, 4.76; N, 19.24.

300 MHz NMR (DMSO-d$_6$) δ0.84 (t, 7.5 Hz, 3H), 1.29 (m, 2H), 1.55 (m, 2H) 2.66 (m, 2H), 4.74 (ABq, J=12.5 Hz, 2H), 5.27 (ABq, J=16 Hz, 2H), 6.97 (d, J

=8.5 Hz, 2H), 7.30, 7.41 ( d, J=8.5 Hz, each 2H), 7.57 (d, J=8.5 Hz, H), 7.65-7.85 (m, 4H), 10.54 (s, 1H).

EXAMPLE 23

Preparation of 3-n-Butyl-5-methylthio-4-[[2'-(1H-tetrazol-5-yl)biphenyl-4-yl]methyl]-4H-1,2,4-triazole

Step A:
3-n-butyl-4-[(2'-cyanobiphenyl-4-yl-methyl]-5-methylthio-4H-1,2,4-triazole A stirred suspension of 500 mg (1.44 mmole) of 5-n-butyl-4-[[2'-cyanobiphenyl-4-yl)methyl]- 2,4-dihydro-3H-1,2,4-triazole-3-thione (from Example 15, Step C) in 4 ml of 2-methoxyethanol was treated with 250 μl (186 mg, 1.44 mmole) of N,N-diisopropylethylamine and then with 90 μl (204 mg, 1.44 mmole) of iodomethane. A clear solution was achieved within 5 minutes. After 5 hours, an additional 25 μl of iodomethane was added. After 5.5 hours, when the reaction appeared complete by TLC, the solution was concentrated in vacuo (oil pump, 30° C.) to half its original volume. The remaining liquid was partitioned between 50 ml of ethyl acetate and 50 μl of 0.2 N HCl. The ethyl acetate phase was washed with an additional portion of 0.2 N HCl and then with saturated NaCl. The organic fraction was dried over MgSO4, filtered, and concentrated to yield 526 mg (100%) of the title compound as an oil, homogeneous by TLC in 19:1 $CH_2Cl_2$—MeOH, suitable for use directly in the next step. In a similar preparation, an analytical sample was obtained by column chromatography on silica gel (gradient elution with 0–2% methanol in $CH_2Cl_2$): yield 85%; mass spectrum (FAB) m/e 363 (M+1)+

Analysis ($C_{21}H_{22}N_4OS.0.5\ H_2O$) Calcd: C, 67.89; H, 6.24; N, 15.09. Found: C, 67.73; H, 6.20; N, 15.02.

300 MHz NMR ($CDCl_3$) δ0.87 (t, J=7.5 Hz, 3H), 1.36 (m, 2H), 1.68 (m, 2H) 2.65 (partially obscured t, J=8 Hz, 2H), 2.67 (s, 3H), 5.08 (s, 2H), 7.16 (d, J=8.5 Hz, 2H), 7.4-7.7 (m, 5H), 7.75 (d, J=8 Hz, 1H).

Step D:
3-n-Butyl-5-methylthio-4-[[2'-(1H-tetrazol-5-yl)biphenyl-4-yl]methyl]-4H-1,2,4-triazole Following the method of Example 18, Step B, the title compound was prepared from 3-n-butyl-4-[(2'-cyanobiphenyl-4-yl)methyl]-5-methylthio-4H-1,2,4-triazole in 56% yield as a stiff foam, mp 100°–102° (preliminary softening), homogeneous by TLC in 9:1$CH_2Cl_2$—MeOH; mass spectrum (FAB) m/e 406 (M+1)+.

Analysis ($C_{21}H_{23}N_7S.0.5\ H_2O.0.3\ CH_2Cl_2$) Calcd: C, 58.62; H, 5.59; N, 22.47. Found: C, 58.38; H, 5.70; N, 22.34.

300 MHz NMR (DMSO-d6) δ0.83 (t, J=7 Hz, 3H), 1.28 (m, 2H), 1.52 (m, 2H) 2.55 (s, 3H), 2.61 (t, J=7.5 Hz, 2H), 5.14 (s, 2H), 7.01, 7.10 (d, J=8 Hz, each 2H), 7.5-7.7 (m, 4H).

EXAMPLE 24

Preparation of 3-n-Butyl-5-methylsulfonyl-4-[[2'-(1H-tetrazol-5-yl)biphenyl-4-yl]methyl]-4H-1,2,4-triazole A solution of 145 mg (0.36 mmole) of 3-n-butyl-5-methylthio-4-[[2'-(1H-tetrazol-5-yl)biphenyl-4-yl]methyl]-4H-1,2,4-triazole (from Example 23) in 0.5 ml of 10% peracetic acid in acetic acid was stirred at room temperature in a stoppered flask for 3 days and then partitioned between 15 ml of ethyl acetate and 15 ml of dilute HCl (pH 2.5). The aqueous phase was further extracted with 2×15 ml of ethyl acetate. The combined organic fractions were dried (MgSO4), filtered, and concentrated in vacuo. Trituration of the residue with ether gave 117 mg (70%) of white solid, mp 98°–100° C. (preliminary softening), homogeneous by TLC in 90:10:1 $CH_2Cl_2$—MeOH-concd. NH4OH (developed 2×); mass spectrum (FAB) m/e 438 (M+1)+.

Analysis [$C_{21}H_{23}N_7O_2S.\frac{1}{4}H_2O.\frac{1}{4}C_4H_{10}O$ (ether)-]Calcd: C, 57.22; H, 5.67; N, 21.23. Found: C, 57.27; H, 5.59; N, 21.22.

300 MHz NMR (DMSO-d6) δ0.81 (t, J=7 Hz, 3H), 1.28 (m, 2H), 1.52 (m, 2H) 2.63 (t, J=8 Hz, 2H), 3.48 (s, 3H), 5.53 (s, 2H), 7.11 (s, 4H), 7.5-7.75 (m, 4H), 11.93 (br s, 1H).

EXAMPLE 25

Preparation of 3-Benzyloxy-5-n-butyl-4-[[2'-(1H-tetrazol-5-yl)biphenyl-4-yl]methyl]-4H-1,2,4triazole A solution of 35 mg (0.08 mmole) of 3-n-butyl-5-methylsulfonyl-4-[[2'-(1H-tetrazol-5-yl)biphenyl-4-yl]methyl]-4M-1,2,4-triazole (from Example 24) in 300 μl (0.21 mmole) of 0.71 M sodium benzyloxide in benzyl alcohol (freshly prepared from sodium and benzyl alcohol) was stirred at 60° C. for 20 hours, by which time TLC (90:10:1$CH_2Cl_2$—MeOH-concd. NH4OH, developed 3×) indicated complete reaction. The mixture was partitioned between 20 ml of ethyl acetate and 15 ml of 0.2 N HCl. The organic phase was washed with 2×10 ml of 0.2 N HCl, then dried over anhydrous MgSO4, filtered and concentrated in vacuo. The residue was purified by column chromatography on silica gel (elution with 19:1 and then 9:1$CH_2Cl_2$—MeOH). Concentration of clean product fractions yielded 4.4 mg (12%) of the title compound as a residual glass, homogeneous by TLC in 90:10:1 $CH_2Cl_2$—MeOH-concd. NH4OH; mass spectrum (FAB) m/e 466 (M+1)+.

300 MHz NMR ($CDCl_3$) δ0.79 (t, J=7.5 Hz, 3H), 1.21 (m, 2H), 1.46 (m, 2H) 2.30 (t, J=7.5 Hz, 2H), 4.82 (s, 2H), 5.22 (s, 2H), 6.86, 7.07 (d, J=8 Hz, each 2H), 7.2-7.6 (m, 8H), 7.91 (d, J=8 Hz, 1H).

EXAMPLE 26

Preparation of 3-(N-Benzyl-N-methylcarbamoyl)-5-n-butyl-4-[[2'-(1H-tetrazol-5-yl)biphenyl-4-yl]methyl]-4H-1,2,4-triazole

Step A: Ethyl N-Benzyl-N-methyloxamate

To a solution of 3.22 ml (3.03 g, 25 mmole) of N-benzylmethylamine and 4.04 ml (3.96 g, 50 mmole) of dry pyridine in 95 ml of dry $CH_2Cl_2$ stirred in an ice bath under N2 was added gradually over 10 minutes 2.94 ml (3.58 g, 26.3 mmole) of ethyl oxalyl chloride. After completion of the addition, the cooling bath was removed, and the mixture was allowed to warm to room temperature. After 5 hours, the solution was partitioned between 300 ml of ether and 250 ml of 0.2 N HCl. The organic layer was washed further with 2×250 ml of 0.2 N HCl followed by 250 ml of saturated NaHCO3. The organic solution was dried to yield 5.36 g (97%) of the title compound as a pale yellow oil, homogeneous by TLC in 4:1 hexane-EtOAc; mass spectrum (FAB) m/e 222 (M+1)+. NMR indicated a nearly 1:1 mixture of rotamers.

300 MMz NMR (CDCl₃) δ1.31, 1.36 (t, J=7Hz, total 3H), 2.85, 2.88 (s, total 3H), 4.32, 4.34 (q, J=7Hz, total 2H), 4.42, 4.58 (s, total 2H), 7.2–7.4 (m, 5H).

Step B: 5-Benzyl-5-methylsemioxamazide

A solution of 3.32 g (15 mmole) of ethyl N-benzyl-N-methyloxamate and 1.46 ml (1.50 g, 30 mmole) of hydrazine hydrate in 30 ml of ethanol was stirred overnight at room temperature. The filtered solution was then concentrated in vacuo at <40° C. The residue was taken up in 50 ml of CH₂Cl₂, filtered, and washed with 50 ml of 0.1 N HCl followed by 50 ml of saturated NaHCO₃. The CH₂Cl₂ phase was dried over MgSO₄, filtered, and concentrated in vacuo to give 1.92 g (61%) of the title compound as a nearly colorless gum, virtually homogeneous by TLC in 19:1 CH₂Cl₂—MeOH; mass spectrum (FAB) m/e 208 (M+1)⁺. NMR indicated a mixture of rotamers in approximately a 1:1 ratio.

Analysis (C₁₀H₁₃N₃O₂.0.2 H₂O) Calcd: C, 56.97; H, 6.41; N, 19.93. Found: C, 57.11; H, 6.34; N, 19.55.

300 MHz NMR (CDCl₃) δ2.90, 3.28 (s, total 3H), 3.92 (br s, 2H), 4.60, 5.03 (s, total 2H), 7.2–7.4 (m, 5H), 8.34 (br s, 1H).

Step C: Ethyl Valerate 5-Benzyl-5-methylsemioxamazone

A solution of 1.06 g (6.38 mmole) of ethyl valerimidate hydrochloride [prepared by method of A. J. Hill and I. Rabinowitz, *J. Am. Chem. Soc.*, 48, 734 (1926)] in 10 ml of dry ethanol was stirred under N₂ at approximately −10° C. (ice-MeOH bath) as a solution of 1.32 g (6.38 mmole) of 5-benzyl-5-methylsemioxamazide in 20 ml of dry ethanol was added dropwise over 15–20 minutes. After being stirred at −10° to −5° C. for an additional 30 minutes, the cloudy soltuion was allowed to stand at approximately 5° C. for 42 hours, during which time a precipitate formed. The mixture was rotary evaporated in vacuo at <35° C., and the residue was partitioned between 30 ml of ethyl acetate and 30 ml of H₂O. The ethyl acetate phase was dried (MgSO₄), filtered, and concentrated in vacuo to yield 2.09 g (100%) of the title compound as a colorless, viscous oil, which showed only trace impurities by TLC (19:1 CH₂Cl₂—MeOH); mass spectrum (FAB) m/e 320 (M+1)⁺. NMR indicated the presence of syn and anti isomers as well as amide rotamers.

Analysis [C₁₇H₂₅N₃O₃.0.1 C₄H₈O₂ (ethyl acetate)]- Calcd: C, 63.67; H, 7.93; N, 12.80.
Found: C, 63.34; H, 7.78; N, 12.89.

300 MHz NMR (CDCl₃) δ0.90 (m, 3H), 1.2–1.4 (m, 5H), 1.5–1.7 (m, 2H), 2.2–2.45 (m, 2H), 2.92, 3.39 (s with small satellite peaks, total 3H), 4.0–4.25 (m, 2H), 4.62, 5.16 (s with small satellite peaks, total 7.2–7.4 (m, 5H), 9.46, 10.20 (apparent br d, total 1H).

Step D: [(2′-Cyanobiphenyl-4-yl)methyl]amine

A solution of 5.85 g (25 mmole) of 4-azidomethyl-2′-cyanobiphenyl (from Example 15, Step A) in 50 ml of dry tetrahydrofuran was treated portionwise with 6.55 g (25 mmole) of triphenylphosphine over 3–4 minutes. The solution was stirred at ambient temperature under N₂, and gas evolution proceeded at a moderate rate. A mild exotherm occurred, and the solution was cooled in a water bath as necessary. After 2 hours, by which time gas evolution had ceased, 675 μl (37.5 mmole ) of H₂O was added, and stirring was continued at room temperature under N₂. After 22 hours, the solution was concentrated in vacuo and the residual oil was chromatographed on a column of silica gel (gradient elution with 2–10% methanol in CH₂Cl₂). The residue from evaporation of the pooled product fractions was partitioned between ether-CH₂Cl₂ and saturated Na₂CO₃ (aqueous). The organic phase was dried (Na₂SO₄), filtered, and concentrated in vacuo to yield 4.64 g (89%) of air-sensitive, nearly white crystals, mp 54°–55° C., homogeneous by TLC in 9:1 CH₂Cl₂—MeOH; mass spectrum (FAB) m/e 209 (M+1)⁺.

Analysis (C₁₄H₁₂N₂) Calcd: C, 80.74; H, 5.81; N, 13.45. Found: C, 80.53; H, 5.89; N, 13.12.

300 MHz NMR (CDCl₃) δ1.50 (br s, 2H), 3.92 (s, 2H), 7.35–7.65 (m, 7H), 7.75 (d, J=8Hz, 1H).

Step E:
3-(N-Benzyl-N-methylcarbamoyl)-5-n-butyl-4-[(2′-cyanobiphenyl-4-yl)methyl]-4H-1,2,4-triazole A mixture of 319 mg (1 mmole) of ethyl valerate 5-benzyl-5-methylsemioxamazone (from Step C), 312 mg (1.5 mmole) of [(2′-cyanobiphenyl-4-yl)methyl]amine (from Step D), and 3 ml of dry ethanol was stirred under N₂ in an oil bath at 50° C. for 2 hours and then at 70° C. for an additional 22 hours. The solution was concentrated in vacuo, and a solution of the residue in 30 ml of ethyl acetate was washed with 2×25 ml of 2 N HCl followed by 25 ml of saturated NaHCO₃. The dried (MgSO₄) ethyl acetate phase was filtered and concentrated. Column chromatography of the residue on silica gel (gradient elution using 0.25–5% isopropanol in CH₂Cl₂ gave 353 mg (76%) of the title compound as a hard glass, mp >40° C. (gradual), homogeneous by TLC in 19:1 CH₂Cl₂—MeOH; mass spectrum (FAB) m/e 464 (M+i)⁺. NMR indicated approximately a 1:1 ratio of amide rotamers.

300 MHz NMR (CDCl₃) δ0.90 (m, 3H), 1.40 (m, 2H), 1.76 (m, 2H), 2.73 (m, 2H), 2.94, 3.18 (s, total 3H), 4.64, 4.95 (s, total 2H), 5.45, 5.47 (s, total 2H), 7.1–7.25 (m, 7H), 7.4–7.5 (m, 4H), 7.64 (m, 1H), 7.75 (m, 1H).

Step F:
3-(N-Benzyl-N-methylcarbamoyl)-5-n-butyl-4-[[2′-(1H-tetrazol-5-yl)biphenyl-4-yl]methyl]-4H-1,2,4-triazole A mixture of 232 mg (0.5 mmole) of 3-(N-benzyl-N-methylcarbamoyl)-5-n-butyl-4[(2′-cyanobiphenyl-4-yl)methyl]-4g-1,2,4-triazole (Step E), 361 mg (1.75 mmole) of trimethyltin azide, and 3 ml of dry toluene was stirred at reflux under N₂ for 34 hours. The mixture was concentrated in vacuo, and the residual solid was partitioned between 20 ml of ethyl acetate and 20 ml of 0.5 N HCl. The ethyl acetate phase was washed with an additional portion of 0.5 HCl, then dried (MgSO₄), filtered, and rotary evaporated. The residue was chromatographed on a silica gel column (elution with gradient of 1–10% methanol in CH₂Cl₂). The product fractions were combined and concentrated, giving 180 mg of a foam which was still contaminated with a minor amount of a trimethyltin derivative [recognized in NMR (CDCl₃) by singlet at δ0.76 ppm]. The material was dissolved in 8 ml of dry methanol and treated with 2.0 g of silica gel. The resulting slurry was stirred at room temperature in a stoppered flask for 1.5 hours and then evaporated to dryness in vacuo. The residual powder was layered on top of a silica gel column packed in CH₂Cl₂. Elution with 99:1 and then 9:1 CH₂Cl₂—MeOH afforded 153 mg (59%) of the title compound as an off-white, stiff foam, mp >95° C. (gradual), homogeneous by TLC in 9:1 CH₂Cl₂—MeOH; mass spectrum (FAB) m/e 507 (M+1)⁺. NMR indicated removal of trimethyltin species and showed a mixture of isomers (amide rotamers) in approximately a 1:1 ratio.

Analysis ($C_{29}H_3ON_8O \cdot 0.75\ H_2O$) Calcd: C, 66.97; H, 6.10; N, 21.55. Found: C, 67.18; H, 6.02; N, 21.24.

300 MHz NMR (CDCl$_3$) δ0.87 (m, 3H), 1.35 (m, 2H), 1.66 (m, 2H), 2.60 (m, 2H), 2.91, 3.05 (s, total 3H), 4.59, 4.86 (s, total 2H), 5.27, 5.33 (s, total 2H), 6.9–7.6 (m, 12H), 7.91 (m, 1H).

EXAMPLES 27–54

The following compounds of formula (I) were prepared following the procedure of Examples 1–13 and Schemes 1–15 and 18.

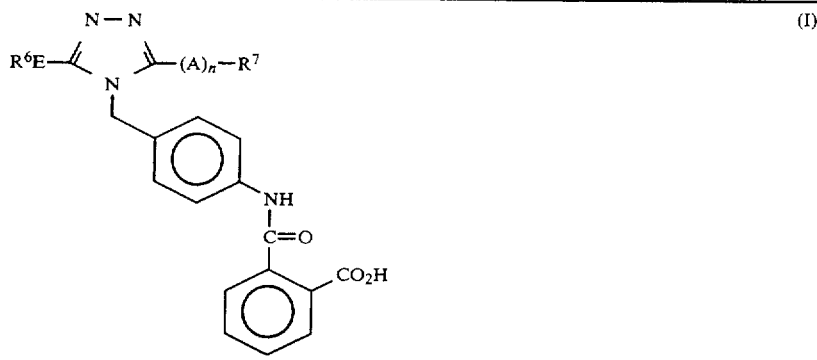

| | R$^6$E | R$^7$—(A)$_n$— | mp | formula | | Analysis C | H | N |
|---|---|---|---|---|---|---|---|---|
| 27 | n-PrS | CF$_3$ | 167–169° C. | C$_{12}$H$_{19}$F$_3$N$_4$O$_3$S·H$_2$O·0.9C$_2$H$_4$O$_2$ (acetic acid) | calcd: found: | 51.03 50.90 | 4.62 4.29 | 10.44 10.29 |
| 28 | n-PrS | phenyl | 166.5–167° C. | C$_{26}$H$_{24}$N$_4$O$_3$S·0.6H$_2$O·0.7C$_4$H$_{10}$O (ether) | calcd: found: | 64.61 64.75 | 5.34 5.34 | 11.47 11.30 |
| 29 | n-Bu | phenyl | 187–188° C. | C$_{27}$H$_{26}$N$_4$O$_3$·1.25H$_2$O | calcd: found: | 67.98 67.81 | 6.02 5.75 | 11.74 11.58 |
| 30 | n-Bu | pyridyl | 108–109° C. | C$_{26}$H$_{25}$N$_5$O$_3$·0.5H$_2$O·CH$_4$O (methanol) | calcd: found: | 65.31 65.31 | 6.09 5.70 | 14.17 13.25 |
| 31 | n-Bu | SCHCO$_2$CH$_3$ \| CH$_2$CH$_3$ | 129–130° C. | C$_{26}$H$_{30}$N$_4$O$_5$S | calcd: found: | 61.16 61.07 | 5.92 5.88 | 10.98 10.87 |
| 32 | n-Bu | SCH$_2$C(=O)-phenyl | 92–93° C. | C$_{29}$H$_{28}$N$_4$O$_4$S·0.75H$_2$O·0.4C$_4$H$_{10}$O (ether) | calcd: found: | 64.27 64.54 | 5.91 5.82 | 9.80 9.44 |
| 33 | n-Pr | SCH$_2$-phenyl | 196–197° C. | C$_{27}$H$_{26}$N$_4$O$_3$S·0.4H$_2$O | calcd: found: | 65.67 65.73 | 5.47 5.54 | 11.35 11.32 |
| 34 | n-Bu | SCH$_2$-(3-methylphenyl) | 164–165° C. | C$_{29}$H$_{30}$N$_4$O$_3$S | calcd: found: | 67.68 67.36 | 5.88 6.05 | 10.89 10.70 |
| 35 | n-Bu | SCH$_2$-(2-methylphenyl) | 166–168° C. | C$_{29}$H$_{30}$N$_4$O$_3$S·0.25H$_2$O | calcd: found: | 67.09 67.21 | 5.92 6.12 | 10.79 10.80 |

-continued

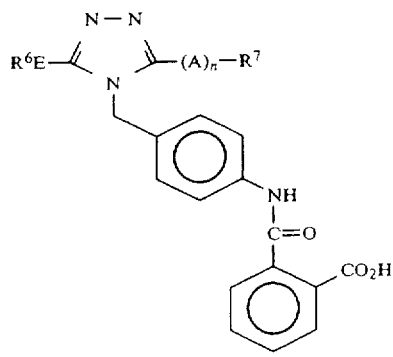

(I)

| | $R^6E$ | $R^7$—$(A)_n$— | mp | formula | Analysis C | H | N |
|---|---|---|---|---|---|---|---|
| 36 | n-Bu | SCH$_2$—C$_6$H$_4$—CH$_3$ | 135–137° C. | $C_{29}H_{30}N_4O_3S \cdot 0.4H_2O$ | calcd: 66.74<br>found: 66.74 | 5.95<br>6.04 | 10.74<br>10.65 |
| 37 | n-Bu | SCH$_2$—C$_6$H$_4$—Cl (2-) | 165–166° C. | $C_{28}H_{27}ClN_4O_3S$ | calcd: 62.85<br>found: 62.84 | 5.09<br>5.09 | 10.47<br>10.47 |
| 38 | n-Bu | SCH$_2$—C$_6$H$_4$—Cl (3-) | 169–170° C. | $C_{28}H_{27}ClN_4O_3S$ | calcd: 62.85<br>found: 62.61 | 5.09<br>5.09 | 10.47<br>10.18 |
| 39 | n-Bu | SCH$_2$—C$_6$H$_4$—Cl (4-) | 115–116° C. | $C_{28}H_{27}ClN_4O_3S \cdot 0.25H_2O$ | calcd: 62.33<br>found: 62.20 | 5.14<br>5.18 | 10.39<br>10.04 |
| 40 | n-Bu | SCH$_2$—C$_6$H$_4$—OCH$_3$ | 94–95° C. | $C_{29}H_{30}N_4O_4S \cdot 0.25H_2O$ | calcd: 65.08<br>found: 65.18 | 5.74<br>5.91 | 10.47<br>10.17 |
| 41 | n-Bu | S(CH$_2$)$_2$—C$_6$H$_5$ | 112–114° C. | $C_{29}H_{30}N_4O_3S \cdot H_2O$ | calcd: 65.39<br>found: 65.19 | 6.06<br>5.95 | 10.52<br>10.17 |
| 42 | EtS | CH$_2$—C$_6$H$_5$ | 179–180° C. | $C_{26}H_{24}N_4O_3S \cdot 0.25H_2O$ | calcd: 65.46<br>found: 65.53 | 5.18<br>5.14 | 11.74<br>11.66 |
| 43 | n-PrS | CH$_2$—C$_6$H$_5$ | >95° C. (grad.) | $C_{27}H_{26}N_4O_3S \cdot 1.5H_2O \cdot 0.5C_4H_6O$(THF) | calcd: 64.96<br>found: 64.71 | 5.92<br>5.62 | 10.45<br>10.35 |
| 44 | n-Bu | SCH(CO$_2$CH$_3$)—C$_6$H$_5$ | 118–119° C. dec | $C_{30}H_{30}N_4O_5S \cdot 0.6H_2O \cdot 0.25C_4H_{10}O$ (ether) | calcd: 63.32<br>found: 63.04 | 5.72<br>5.64 | 9.53<br>9.42 |

-continued

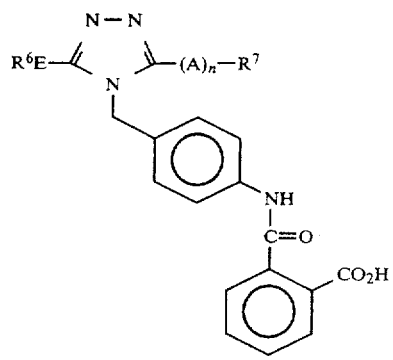

(I)

| | R⁶E | R⁷—(A)ₙ— | mp | formula | | Analysis C | H | N |
|---|---|---|---|---|---|---|---|---|
| 45 | n-Bu | SCH(C₆H₅)CO₂H | 143–145° C. dec | $C_{29}H_{28}N_4O_5S \cdot 2H_2O$ | calcd:<br>found: | 59.98<br>59.79 | 5.55<br>5.23 | 9.65<br>9.45 |
| 46 | n-Bu | SCH₂-C₆H₄-CN | 140–142° C. | $C_{29}H_{27}N_5O_3S \cdot 0.85H_2O \cdot 0.2C_4H_{10}O$ (ether) | calcd:<br>found: | 64.40<br>64.29 | 5.57<br>5.36 | 12.60<br>12.26 |
| 47 | n-Bu | SCH₂-C₆H₄-CF₃ | 118–120° C. | $C_{29}H_{27}F_3N_4O_3S \cdot 0.3H_2O \cdot 0.1C_4H_{10}O$ (ether) | calcd:<br>found: | 60.73<br>60.45 | 4.96<br>5.01 | 9.64<br>9.58 |
| 48 | n-PrS | (CH₂)₂-C₆H₅ | 147–147.5° C. | $C_{28}H_{28}N_6O_3S$ | calcd:<br>found: | 67.18<br>66.98 | 5.64<br>5.78 | 11.19<br>10.98 |
| 49 | n-PrS | (CH₂)₃-C₆H₅ | 152–153° C. | $C_{29}H_{30}N_4O_3S$ | calcd:<br>found: | 67.68<br>67.50 | 5.88<br>5.99 | 10.89<br>10.62 |
| 50 | n-PrS | CH₂S-C₆H₅ | 159–160° C. | $C_{27}H_{26}N_4O_3S_2 \cdot 0.4H_2O$ | calcd:<br>found: | 61.67<br>61.96 | 5.14<br>5.01 | 10.65<br>10.38 |
| 51 | n-Bu | SCH₂-C₆H₄-OCH₃ | 180–182° C. | $C_{29}H_{30}N_4O_4S \cdot 1.1H_2O$ | calcd:<br>found: | 63.27<br>63.06 | 5.90<br>5.65 | 10.18<br>9.97 |
| 52 | n-Bu | SCH₂-naphthyl | 146–147° C. | $C_{32}H_{30}N_4O_3S \cdot 0.5H_2O \cdot 0.2C_4H_{10}O$ (ether) | calcd:<br>found: | 68.57<br>68.53 | 5.79<br>5.91 | 9.75<br>9.52 |
| 53 | n-Bu | SCH₂-C₆H₄-CO₂CH₃ | 115–116° C. dec | $C_{30}H_{30}N_4O_5S \cdot 0.75H_2O \cdot 0.25C_4H_{10}O$ (ether) | calcd:<br>found: | 63.03<br>62.97 | 5.80<br>5.65 | 9.49<br>9.40 |

-continued (I)

[Structure: R⁶E-C(=N-N=)-N(-(A)ₙ-R⁷) attached via CH₂ to phenyl-NH-C(=O)-phenyl-CO₂H]

| | R⁶E | R⁷—(A)ₙ— | mp | formula | Analysis | | |
|---|---|---|---|---|---|---|---|
| | | | | | C | H | N |
| 54 | n-Bu | -SCH₂-phenyl-3-CO₂H | 130–132° C. dec | C₂₉H₂₈N₄O₅S·2.5H₂O·0.1C₄H₁₀O (ether) | calcd: 59.14  found: 59.29 | 5.74  5.44 | 9.39  9.19 |

EXAMPLES 55–76

The following compounds of formula (I) are prepared following the procedures of Example 14 and Schemes 1–14, 16 and 18.

(I)

[Structure: R⁶E-C(=N-N=)-N(-(A)ₙ-R⁷) attached via CH₂ to biphenyl-2'-CO₂H]

| | R⁶E | R⁷—(A)ₙ— |
|---|---|---|
| 55 | n-Bu | —SCH₂—phenyl |
| 56 | n-Bu | —SCH₂—phenyl—NO₂ |
| 57 | n-Bu | —SCH₂—phenyl—OCH₃ |
| 58 | n-Bu | —SCH₂—phenyl—Cl |

-continued (I)

[Structure: R⁶E-C(=N-N=)-N(-(A)ₙ-R⁷) attached via CH₂ to biphenyl-2'-CO₂H]

| | R⁶E | R⁷—(A)ₙ— |
|---|---|---|
| 59 | n-Bu | —SCH₂—phenyl(2-CH₃) |
| 60 | n-Bu | —SCH₂—phenyl(3-CH₃) |
| 61 | n-Bu | —SCH₂—phenyl(4-CH₃) |
| 62 | n-Bu | —SCH₂—phenyl(2-CO₂CH₃) |

-continued $$\underset{\underset{\underset{CO_2H}{\bigodot}}{\underset{\bigodot}{\overset{\mid}{N}}}}{R^6E} \underset{N}{\overset{N-N}{\diagdown}} (A)_n - R^7 \quad (I)$$

|  | R⁶E | R⁷—(A)ₙ— |
|---|---|---|
| 63 | n-Bu | —SCH₂—C₆H₄—CO₂CH₃ (ortho) |
| 64 | n-Bu | —SCH₂—C₆H₄—CO₂CH₃ (para) |
| 65 | n-Bu | —S—CH(CO₂CH₃)—C₆H₅ |
| 66 | n-Bu | —SCH₂—C₆H₄—CO₂H (ortho) |
| 67 | n-Bu | —SCH₂—C₆H₄—CO₂H (meta) |
| 68 | n-Bu | —SCH₂—C₆H₄—CO₂H (para) |
| 69 | n-Bu | —SCH(CO₂H)—C₆H₅ |
| 70 | n-Bu | —SCH₂—C₆H₄—CH₂OH (ortho) |

-continued $$\underset{\underset{\underset{CO_2H}{\bigodot}}{\underset{\bigodot}{\overset{\mid}{N}}}}{R^6E} \underset{N}{\overset{N-N}{\diagdown}} (A)_n - R^7 \quad (I)$$

|  | R⁶E | R⁷—(A)ₙ— |
|---|---|---|
| 71 | n-Bu | —S—CH₂—C₆H₄—CH₂OH (meta) |
| 72 | n-Bu | —SCH₂—C₆H₄—CH₂OH (para) |
| 73 | n-Bu | —S—CH(CH₂OH)—C₆H₅ |
| 74 | n-Bu | —SCH₂—(2-thienyl) |
| 75 | n-Bu | —S(=O)CH₂—C₆H₄—NO₂ |
| 76 | n-Bu | —S(=O)CH₂—C₆H₄—Cl |

Analogous compounds wherein $R^7$—$(A)_n$— is phenylthio or substituted phenylthio in place of benzylthio as shown in place of benzylthio as shown above, can be prepared following Schemes 5, 16 and 18 and Examples 5 and 14.

EXAMPLES 77–92

The following compounds of formula (I) were prepared following the procedures of Examples 15–20 and 23–26 and Schemes 1–14, 17 and 18.

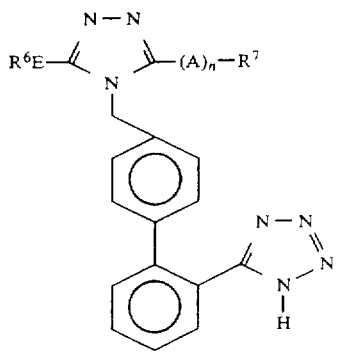

(I)

| | R⁶E | R⁷—(A)ₙ— | mp | formula | | Analysis C | H | N |
|---|---|---|---|---|---|---|---|---|
| 77 | n-Bu | SCH₂—Ph | 107° C. dec | $C_{27}H_{27}N_7S \cdot 0.5H_2O \cdot 0.05CH_2Cl_2$ | calcd: found: | 65.65 65.64 | 5.72 5.64 | 19.82 19.54 |
| 78 | n-Bu | S—Ph | 84–85° C. dec | $C_{26}H_{25}N_7S \cdot 0.75H_2O \cdot 0.15CH_2Cl_2$ | calcd: found: | 64.02 64.30 | 5.50 5.50 | 20.03 19.72 |
| 79 | n-Bu | S(CH₂)₂—Ph | 79–80° C. | $C_{28}H_{29}N_7S \cdot 0.75H_2O$ | calcd: found: | 66.05 66.32 | 6.04 5.92 | 19.26 19.16 |
| 80 | n-Pr | SCH₂—Ph—Cl | 90–92° C. | $C_{26}H_{24}ClN_7S \cdot 0.02H_2O \cdot 0.8CH_4O$ (methanol) | calcd: found: | 60.58 60.65 | 5.24 5.15 | 18.46 18.10 |
| 81 | n-Pentyl | SCH₂—Ph—Cl | 97–99° C. | $C_{28}H_{28}ClN_7S \cdot 0.75H_2O$ | calcd: found: | 61.86 61.85 | 5.45 5.41 | 18.04 18.12 |
| 82 | n-Bu | SCH₂—Ph—Cl | 79–80° C. | $C_{27}H_{26}ClN_7S \cdot 0.1CH_2Cl_2$ | calcd: found: | 62.06 62.34 | 5.03 5.24 | 18.70 18.58 |
| 83 | n-Bu | SCH₂—Ph—O₂N | >115° C. | $C_{27}H_{26}N_8O_2S \cdot 0.75H_2O$ | calcd: found: | 60.03 59.93 | 5.13 5.13 | 20.75 20.47 |
| 84 | n-Bu | SCH₂—Ph—OCH₃ | 78–80° C. | $C_{28}H_{29}N_7OS$ | | | | |
| 85 | n-Bu | SCH₂—Ph—OCH₃ | 95–97° C. | $C_{28}H_{29}N_7OS$ | | | | |

-continued

EXAMPLES 93–108

The following compounds of formula (I) were or can be prepared following the procedure of Examples 21 and 22 and Schemes 1–15, 18 and 19.

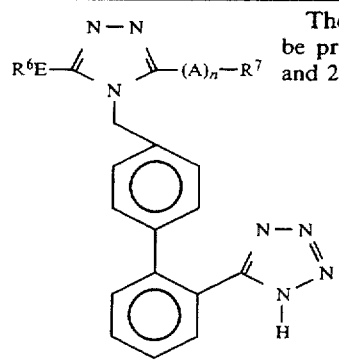

| | R⁶E | R⁷—(A)ₙ— | mp | formula | | Analysis C | H | N |
|---|---|---|---|---|---|---|---|---|
| 86 | n-Bu | SCH₂—[phenyl]—CH₃O₂C | 120–122° C. dec | $C_{29}H_{29}N_7O_2S \cdot 1.5H_2O \cdot 0.2CH_2Cl_2$ | calcd: found: | 59.62 59.77 | 5.55 5.44 | 16.67 16.44 |
| 87 | n-Bu | SCH₂—[phenyl]—HO₂C | 203–204° C. dec | $C_{28}H_{27}N_7O_2S$ | | | | |
| 88 | n-Bu | SCH₂—[phenyl]—HOCH₂ | 93–95° C. | $C_{28}H_{29}N_7OS \cdot 0.3H_2O \cdot 0.25CH_2Cl_2$ | calcd: found: | 63.03 63.29 | 5.64 5.92 | 18.22 17.89 |
| 89 | n-Bu | SCH₂CH(CH₃)₂ | 90–91° C. | $C_{24}H_{29}N_7S \cdot 0.15CH_2Cl_2$ | calcd: found: | 63.00 63.07 | 6.42 6.50 | 21.30 21.00 |
| 90 | n-Bu | $\overset{O}{\underset{\|}{\|}}$SCH₂—[phenyl]—OCH₃ | 125–126° C. | $C_{28}H_{29}N_7O_2S$ | | | | |
| 91 | n-Bu | $\overset{O}{\underset{\|}{\|}}$SCH₃ | 106–107° C. | $C_{21}H_{23}N_7OS$ | | | | |
| 92 | n-Bu | $\overset{O}{\underset{\|}{\|}}$CN(CH₃)—[phenyl] | >100° C. | $C_{28}H_{28}N_8O \cdot 0.15CH_2Cl_2$ | calcd: found: | 66.91 67.27 | 5.65 5.90 | 22.18 21.82 |

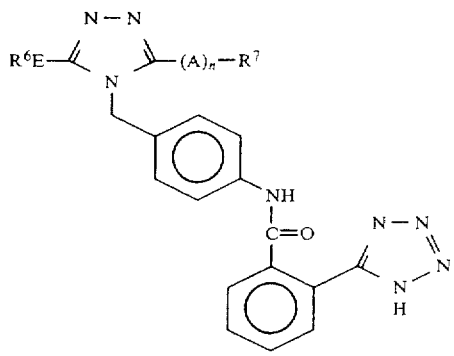
|  | R⁶E | R⁷(A)ₙ— | mp | formula | | Analysis C | H | N |
|---|---|---|---|---|---|---|---|---|
| 93 | n-Bu | SCH₂-⟨⟩-OCH₃ | 130–132° C. dec. | C₂₉H₃₀N₈O₂S·0.5H₂O | calcd: found: | 61.79 61.50 | 5.54 5.52 | 19.88 19.78 |
| 94 | n-Bu | O↑SCH₂-⟨⟩-OCH₃ | 135–137° C. | C₂₉H₃₀N₈O₃S·0.25H₂O·0.15C₄H₈O₂ (ethyl acetate) | calcd: found: | 60.42 60.25 | 5.43 5.60 | 19.05 18.88 |
| 95 | n-Bu | SCH₂-⟨⟩-CH₃ | | | | | | |
| 96 | n-Bu | SCH₂-⟨⟩ | | | | | | |
| 97 | n-Bu | SCH₂-⟨⟩ (CH₃O₂C) | | | | | | |
| 98 | n-Bu | SCH₂-⟨⟩ (HO₂C) | | | | | | |
| 99 | n-Bu | SCH₂-⟨⟩ (HOCH₂) | | | | | | |
| 100 | n-Bu | SCH₂-⟨⟩ (CO₂CH₃) | | | | | | |

-continued
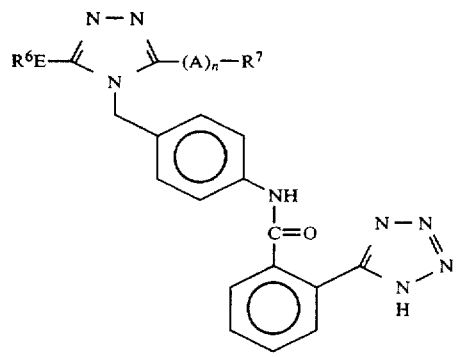
(I)
| | R⁶E | R⁷(A)ₙ— | mp | formula | Analysis C H N |
|---|---|---|---|---|---|
| 101 | n-Bu | SCH₂—C₆H₄—CO₂H (meta) | | | |
| 102 | n-Bu | SCH₂—C₆H₄—CH₂OH (meta) | | | |
| 103 | n-Bu | SCH₂—C₆H₄—CO₂CH₃ (para) | | | |
| 104 | n-Bu | SCH₂—C₆H₄—CO₂H (para) | | | |
| 105 | n-Bu | SCH₂—C₆H₄—CH₂OH (para) | | | |
| 106 | n-Bu | SCH(CO₂CH₃)—C₆H₅ | | | |
| 107 | n-Bu | SCH(CO₂H)—C₆H₅ | | | |
| 108 | n-Bu | SCH(CH₂OH)—C₆H₅ | | | |
EXAMPLES 109–115
The following compounds of formula (I) can be prepared according to Schemes 20–22 (and earlier Schemes referred to therein).

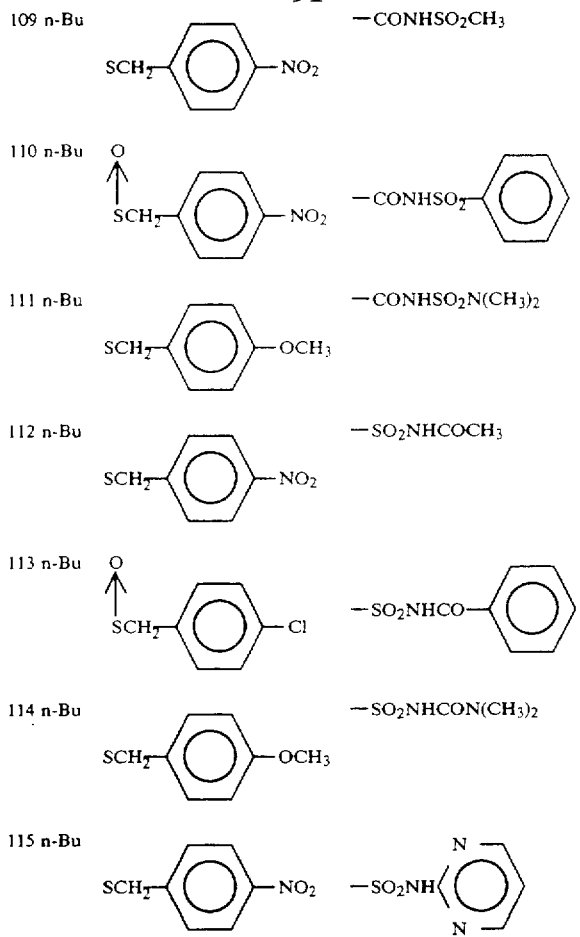

EXAMPLE 116

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| 3-Benzylthio-5-n-butyl-4-[4-(2-carboxybenzamido)-benzyl]-4H-1,2,4-triazole | 50 |
| Lactose | 149 |
| Magnesium stearate | 1 |
| Capsule (size No. 1) | 200 |

3-Benzylthio-5-n-butyl-4-[4-(2-carboxybenzamido)-benzyl]-4H-1,2,4-triazole can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 3-benzyl thio-5-n-butyl-4-[4-(2-carboxybenzamido)benzyl]-4H-1,2,4-triazole (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of 3-benzylthio-5-n-butyl-4-[4-(2carboxybenzamido)benzyl]-4H-1,2,4-triazole (25 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 3-benzylthio-5-n-butyl-4-[4-(2-carboxybenzamido)benzyl]-4H-1,2,4-triazole (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 3-benzylthio-5-n-butyl-4-[4-(2-carboxybenzamido)benzyl]-4H-1,2,4-triazole (25 mg) sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of the formula (I):

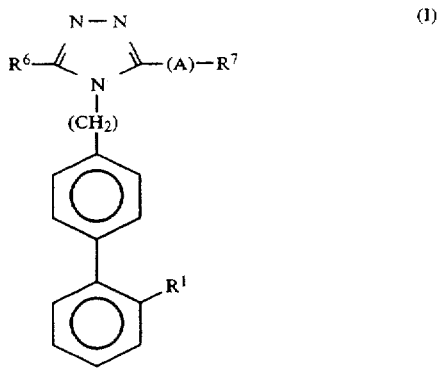

wherein
$R^1$ is
(a) —$CO_2R^4$,

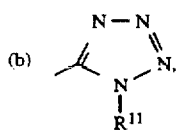

wherein $R^4$ is H, $R_6$ is straight chain or branched $C_1$–$C_6$alkyl, which can be optionally substituted with a substituent selected from the group consisting of aryl, wherein aryl is phenyl or naphthyl, optionally substituted with a substituent selected from the group consisting of (Cl, Br, I, F), $C_{1-4}$-alkyl, $C_{1-4}$-alkoxy, $NO_2$, $CF_3$, $C_{1-4}$-alkylthio, OH or $NH_2$; and —O—$C_{1-4}$-alkyl, $C_3$–$C_7$-cycloalkyl, halo (Cl, Br, I, F), —OH, —$NH_2$, —$NH(C_1$–$C_4$-alkyl), —$N(C_1$–$C_4$-alkyl)$_2$, —NH—$SO_2R^4$, —$COOR^4$, —$SO_2NHR^9$;

A is $S(O)p$, wherein p is 0 to 2;

$R^7$ is
  (a) $C_1$–$C_{10}$-alkyl;
  (b) substituted $C_1$–$C_{10}$ alkyl in which one or two substituent(s) are selected from
    (1) halogen,
    (2) hydroxy,
    (3) $C_1$–$C_{10}$-alkoxy,
    (4) $C_1$–$C_5$-alkoxycarbonyl,
    (5) $C_1$–$C_4$-alkylcarbonyloxy,
    (6) $C_3$–$C_8$-cycloalkyl,
    (7) aryl, as defined above,
    (8) di-substituted aryl, as defined above, in which the substituents are V and W, defined below
    (9) $C_1$–$C_{10}$-alkyl-$S(O)p$,
    (10) $C_3$–$C_8$-cycloalkyl-$S(O)p$,
    (11) phenyl-$S(O)p$,
    (12) di-substituted phenyl-$S(O)p$ in which the substituents are V and W,
    (13) oxo,
    (14) carboxy,
    (15) $NR^9R^{10}$,
    (16) $C_1$–$C_5$-alkylaminocarbonyl,
    (17) di($C_1$–$C_5$-alkyl)aminocarbonyl,
    (18) cyano;
  (c) perfluoro-$C_1$–$C_4$-alkyl, selected from $CF_3$, $CF_3CF_2$, $CF_3CF_2CF_2$, $CF_3CF_2CF_2CF_2$;
  (d) $C_2$–$C_{10}$-alkenyl,
  (e) $C_2$–$C_{10}$-alkynyl,
  (f) $C_3$–$C_8$-cycloalkyl,
  (g) substituted $C_3$–$C_8$-cycloalkyl in which one or two substituent(s) are selected from:
    (1) halogen,
    (2) hydroxy,
    (3) $C_1$–$C_{10}$-alkoxy,
    (4) $C_1$–$C_5$-alkoxycarbonyl,
    (5) $C_1$–$C_5$-alkylcarbonyloxy,
    (6) $C_3$–$C_8$-cycloalkyl,
    (7) aryl, as defined above,
    (8) di-substituted aryl, as defined above, in which the substituents are V and W,
    (9) $C_1$–$C_{10}$-alkyl-$S(O)p$ in which p is 0 to 2,
    (10) $C_3$–$C_8$-cycloalkyl-$S(O)p$,
    (11) phenyl-$S(O)p$,
    (12) di-substituted phenyl-$S(O)p$ in which the substituents are V and W,
    (13) oxo,
    (14) carboxy,
    (15) $NR^9R^{10}$,
    (16) $C_1$–$C_5$-alkylaminocarbonyl,
    (17) di($C_1$–$C_5$-alkyl)aminocarbonyl,
    (18) cyano,
    (19) $C_1$–$C_4$-alkylcarbonyl;
  (h) aryl, as defined above,
  (i) di-substituted aryl in which the substituents are V and W,
  (j) aryl-$(CH_2)_r$-$(B)_b$-$(CH_2)_t$—, wherein aryl is defined above,
  (k) substituted aryl-$(CH_2)_r$-$(B)_b$-$(CH_2)_t$— in which the aryl group is defined above and di-substituted with V and W; wherein
    B is —C(O)—S—, —O—, —$NR^4$, —$NR^4C(O)$—, or —$C(O)NR^4$;
    b is 0 or 1;
    r and t are 0 to 2;
    $R^4$ is defined above;

V and W are each independently selected from;
  (a) H,
  (b) $C_1$–$C_5$-alkoxy,
  (c) $C_1$–$C_5$-alkyl,
  (d) hydroxy,
  (e) $C_1$–$C_5$-alkyl-$S(O)p$,
  (f) —CN,
  (g) —$NO_2$,
  (h) —$NR^9R^{10}$,
  (i) $C_1$–$C_4$-alkyl-$CONR^9R^{10}$,
  (j) —$CO_2R^9$,
  (k) $C^1$–$C^5$-alkyl-carbonyl,
  (l) trifluoromethyl,
  (m) halogen,
  (n) hydroxy-$C^1$–$C^4$-alkyl,
  (o) $C^1$–$C^4$-alkyl-$CO_2R^9$,
  (p) -1H-tetrazol-5-yl,
  (q) —$NHSO_2CF_3$,
  (r) aryl as defined above,
  (s) —$OCONR^9R^{10}$,
  (t) —$NR^4CO_2R^9$,
  (u) —$NR^4CONR^9R^{10}$,
  (v) —$NR^4CON(CH_2CH_2)_2Q$ where Q is O, $S(O)p$ or $NR^9$,
  (w) —$OCON(CH_2CH_2)_2Q$ where Q is as defined above;
  (x) —$CONR^9R^{10}$;

$R^9$ is H, $C_1$–$C_5$alkyl, phenyl or benzyl;
$R^{10}$ is H, $C_1$–$C_4$-alkyl; or
$R^{11}$ is H, $C_{1-6}$-alkyl, $C_2$–$C_4$-alkenyl, $C_1$–$C_4$-alkoxy-$C_1$–$C_4$-alkyl, or —$CH_2$–$C_6H_4R^{20}$;
$R^{20}$ is H, —$NO_2$, —$NH_2$, —OH or —$OCH_3$;
$R^9$ and $R^{19}$ together may be —$(CH_2)_m$— where m is 3–6;

or a pharmaceutically acceptable salt thereof.

2. A compound of claim 1 wherein:
$R^1$ is 1H-tetrazol-5-yl;
$R^6$ is $C_1$–$C_6$ alkyl optionally substituted with a substituent selected from the group consisting of Cl, $CF_3$, OH, —O—$CH_3$, —$OC_2H_5$, or phenyl;
$R^7$ is
  (a) $C_1$–$C_{10}$-alkyl,
  (b) substituted $C_1$–$C_{10}$ alkyl in which one or two substituents are selected from;
    (1) hydroxy,
    (2) $C_1$–$C_5$-alkoxy,
    (3) $C_1$–$C_5$-alkoxycarbonyl,
    (4) $C_1$–$C_4$-alkylcarbonyloxy,
    (5) $C_3$–$C_8$-cycloalkyl,
    (6) phenyl,
    (7) di-substituted phenyl in which the substituents are V and W,
    (8) $C_1$–$C_5$-alkyl-$S(O)p$,
    (9) phenyl-$S(O)p$,
    (10) di-substituted phenyl $S(O)p$ in which the substituents are V and W,
    (11) oxo,
    (12) carboxy,
    (13) $C_1$–$C_5$-alkylaminocarbonyl,
    (14) di($C_1$–$C_5$-alkyl)aminocarbonyl;

A is —S—, or —S(O)—

V and W are independently selected from
(a) hydrogen,
(b) $C_1$-$C_5$-alkoxy,
(c) $C_1$-$C_5$-alkyl,
(d) hydroxy,
(e) $NR^9R^{10}$,
(f) $CO_2R^9$,
(g) trifluoromethyl,
(h) halogen,
(i) hydroxy-$C_1$-$C_4$-alkyl-,
(j) -1H-tetrazol-5-yl,
(k) —$NHSO_2CF_3$,
(l) $C_1$-$C_5$-alkyl-S(O)p-,
(m) —CN,
(n) —$NO_2$,
(o) $C_1$-$C_4$-alkyl-$CONR^9R^{10}$m
(p) $C_1$-$C_5$-alkylcarbonyl,
(q) —$CONR^9R^{10}$,
(r) —COOH.

3. A compound of claim 1 wherein $R^6$ is $C_1$-$C_6$-alkyl.

4. A compound of claim 1 wherein
$R^6$ is n-butyl;
$R^7$ is substituted $C_1$-$C_{10}$-alkyl in which one or two substituents are selected from:
(1) hydroxy,
(2) $C_1$-$C_5$-alkoxy,
(3) $C_1$-$C_5$-alkoxycarbonyl,
(4) phenyl, which can be substituted by V or W,
(5) carboxy,
(6) $C_1$-$C_5$-alkylaminocarbonyl;

V and W are selected from:
(a) hydrogen,
(b) $C_1$-$C_5$-alkyl,
(c) $C_1$-$C_5$-alkoxy,
(d) $CO_2R^9$,
(e) halogen,
(f) hydroxy-$C^1$-$C^4$-alkyl-,
(g) -1H-tetrazol-5-yl-,
(h) —$NHSO_2CH_3$,
(i) —CN,
(j) —$NO_2$.

5. A compound of claim 1 selected from the group consisting of:
(1) 3-Benzylthio-5-n-butyl-4-[(2'-carboxybiphenyl-4-yl)methyl]-4H-1,2,4-triazole;
(2) 3-n-Butyl-4-[(2'-carboxybiphenyl-4-yl)methyl]-5-(4-nitrobenzylthio)-4H-1,2,4-triazole;
(3) 3-n-Butyl-4-[(2'-carboxybiphenyl-4-yl)methyl]-5-(4-methoxybenzylthio)-4H-1,2,4-triazole;
(4) 3-n-Butyl-4-[(2'-carboxybiphenyl-4-yl)methyl]-5-(4-chlorobenzylthio)-4H-1,2,4-triazole;
(5) 3-n-Butyl-4-[(2'-carboxybiphenyl-4-yl)methyl]-5-(4-methylbenzylthio)-4H-1,2,4-triazole;
(6) 3-n-Butyl-5-[2-(carbomethoxy)benzylthio]-4-[(2'-carboxybiphenyl-4-yl)methyl]-4H-1,2,4-triazole;
(7) 3-n-Butyl-5-[α-(carbomethoxy)benzylthio]-4-[(2'-carboxybiphenyl-4-yl)methyl]-4H-1,2,4-triazole;
(8) 3-n-Butyl-5-(2-carboxybenzylthio)-4-[(2'-carboxybiphenyl-4-yl)methyl]-4H-1,2,4-triazole;
(9) 3-n-Butyl-5-(α-carboxybenzylthio)-4-[(2'-carboxybiphenyl-4-yl)methyl]-4H-1,2,4-triazole;
(10) 3-n-Butyl-4-[(2'-carboxybiphenyl-4-yl)methyl]-5-[2-(hydroxymethyl)benzylthio]-4H-1,2,4-triazole;
(11) 3-n-Butyl-4-[(2'-carboxybiphenyl-4-yl)methyl]-5-(cyclohexylmethylthio)-4H-1,2,4-triazole;
(12) 3-n-Butyl-4-[(2'-carboxybiphenyl-4-yl)methyl]-5-(4-nitrobenzylsulfinyl)-4H-1,2,4-triazole; and,
(13) 3-n-Butyl-4-[(2'-carboxybiphenyl-4-yl)methyl]-5-(4-chlorobenzylsulfinyl)-4H-1,2,4-triazole, 6. A compound of claim 1 selected from the group consisting of:
(1) 3-n-Butyl-5-(4-chlorobenzylthio)-4-[(2'-(1H-tetrazol-5-yl)biphenyl-4-yl)methyl]-4H-1,2,4-triazole;
(2) 3-n-Butyl-5-(4-chlorobenzylsulfinyl)-4-[[2'-(1H-tetrazol-5-yl)biphenyl-4-yl]methyl]-4H-1,2,4-triazole;
(3) 3-n-Butyl-5-(4-nitrobenzylthio)-4-[[2'-(1H-tetrazol-5-yl)biphenyl-4-yl]methyl]-4H-1,2,4-triazole;
(4) 3-n-Butyl-5-(4-nitrobenzylsulfinyl)-4-[[2-(1H-tetrazol-5-yl)biphenyl-4-yl]methyl]-4H-1,2,4-triazole;
(5) 3-n-Butyl-5-(cyclohexylmethylthio)-4-[[2'-(1H-tetrazol-5-yl)biphenyl-4-yl]methyl]-4H-1,2,4-triazole;
(6) 3-(N-Benzyl-N-methylcarbamoyl)-5-n-butyl-4-[[2'-(1H-tetrazol-5-yl)biphenyl-4-yl]-methyl]-4H-1,2,4-triazole;
(7) 3-Benzylthio-5-n-butyl-4-[[2'-(1H-tetrazol-5-yl)biphenyl-4-yl]methyl]-4H-1,2,4-triazole;
(8) 3-n-Butyl-5-phenethylthio-4-[[2'-(1H-tetrazol-5-yl)biphenyl-4-yl]methyl]-4H-1,2,4-triazole;
(9) 3-n-Butyl-5-(4-methoxybenzylthio)-4-[[2'-(1H-tetrazol-5-yl)biphenyl-4-yl]methyl]-4H-1,2,4-triazole;
(10) 3-n-Butyl-5-[2-(carbomethoxy)benzylthio]-4-[[2'-(1H-tetrazol-5-yl)biphenyl-4-yl]methyl]-4H-1,2,4-triazole;
(11) 3-n-Butyl-5-(2-carboxybenzylthio)-4-[[2'-(1H-tetrazol-5-yl)biphenyl-4-yl]methyl]-4H-1,2,4-triazole;
(12) 3-n-Butyl-5-[2-(hydroxymethyl)benzylthio]-4-[[2'-(1H-tetrazol-5-yl)biphenyl-4-yl]methyl]-4H-1,2,4-triazole; and,
(13) 3-n-Butyl-5-(4-methoxybenzylsulfinyl)-4-[[2'-(1H-tetrazol-5-yl)biphenyl-4-yl]methyl]-4H-1,2,4-triazole.

* * * * *